(12) United States Patent
Wallace et al.

(10) Patent No.: US 12,357,460 B2
(45) Date of Patent: Jul. 15, 2025

(54) SYSTEM AND METHOD FOR CARDIAC VALVE REPAIR

(71) Applicant: Versa Vascular Inc., Oakland, CA (US)

(72) Inventors: Daniel T. Wallace, Santa Cruz, CA (US); Juan Granada, Upper Saddle River, NJ (US); Jeremy J. Boyette, Woodside, CA (US); Peter W. Gregg, Santa Cruz, CA (US); Spencer C. Noe, San Miguel, CA (US); Evelyn N. Haynes, Los Gatos, CA (US)

(73) Assignee: Versa Vascular Inc.

( * ) Notice: Subject to any disclaimer, the term of this patent is extended or adjusted under 35 U.S.C. 154(b) by 883 days.

(21) Appl. No.: 17/550,660

(22) Filed: Dec. 14, 2021

(65) Prior Publication Data

US 2022/0183840 A1  Jun. 16, 2022

Related U.S. Application Data

(63) Continuation-in-part of application No. 17/227,847, filed on Apr. 12, 2021, now Pat. No. 11,266,502.
(Continued)

(51) Int. Cl.
*A61F 2/24* (2006.01)

(52) U.S. Cl.
CPC .......... *A61F 2/2442* (2013.01); *A61F 2/2433* (2013.01); *A61F 2/2445* (2013.01); *A61F 2/246* (2013.01); *A61F 2/2466* (2013.01)

(58) Field of Classification Search
CPC ...... A61F 2/2442; A61F 2/2445; A61F 2/246; A61F 2/2463; A61F 2/2466
See application file for complete search history.

(56) References Cited

U.S. PATENT DOCUMENTS 6,540,782 B1 * 4/2003 Snyders ................ A61F 2/2436
                                                    623/2.14
8,409,273 B2    4/2013 Thornton et al.
(Continued)

FOREIGN PATENT DOCUMENTS

| CN | 102512271 A | 6/2012 |
| EP | 1251803 B1 | 6/2005 |
| WO | WO 2022/132788 A1 | 6/2022 |

OTHER PUBLICATIONS

International Search Report and Written Opinion, PCT/US2023/024623, dated Oct. 4, 2023, 12 pgs.
(Continued)

*Primary Examiner* — William H Matthews
(74) *Attorney, Agent, or Firm* — Polsinelli PC

(57) ABSTRACT

A valve implant includes an occlusive assembly and a frame coupled to the occlusive assembly. The frame transitions from a collapsed state to an expanded state about a central longitudinal axis and transitioning from the collapsed state to the expanded state causes a proximal end of the frame to expand radially outward from the central longitudinal axis. The valve implant further includes an outer sheet supported on a proximal portion of the frame. The occlusive assembly is supported on a distal portion of the frame such that the inner sheet extends about the central longitudinal axis and an annular opening is defined between the outer sheet and the inner sheet when the frame is in the expanded state.

20 Claims, 38 Drawing Sheets

Related U.S. Application Data

(60) Provisional application No. 63/125,035, filed on Dec. 14, 2020.

(56) References Cited

U.S. PATENT DOCUMENTS

| | | |
|---|---|---|
| 9,795,480 B2 | 10/2017 | Bolling et al. |
| 10,070,858 B2 | 9/2018 | Shelton |
| 10,136,993 B1 | 11/2018 | Metchik |
| 10,898,325 B2 | 1/2021 | Calomeni |
| 11,058,411 B2 | 7/2021 | Bar |
| 11,207,180 B2 | 12/2021 | Ganesan et al. |
| 11,510,780 B2 | 11/2022 | Granada et al. |
| 2005/0038508 A1 | 2/2005 | Gabbay |
| 2011/0137335 A1 | 6/2011 | Hallisey |
| 2012/0109181 A1 | 5/2012 | Hallisey |
| 2012/0323174 A1 | 12/2012 | Shih |
| 2012/0323317 A1 | 12/2012 | Karapetian et al. |
| 2014/0067048 A1 | 3/2014 | Chau et al. |
| 2015/0148896 A1 | 5/2015 | Karapetian |
| 2016/0113766 A1 | 4/2016 | Ganesan |
| 2017/0319333 A1 | 11/2017 | Tegels et al. |
| 2018/0021044 A1 | 1/2018 | Miller |
| 2018/0193138 A1 | 7/2018 | Vidlund |
| 2019/0029818 A1 | 1/2019 | Siegel |
| 2019/0029827 A1 | 1/2019 | Bar |
| 2019/0029854 A1 | 1/2019 | Calomeni et al. |
| 2019/0142580 A1 | 5/2019 | Delgado |
| 2019/0254824 A1 | 8/2019 | Bar |
| 2020/0383783 A1 | 12/2020 | Anderson et al. |
| 2021/0361428 A1 | 11/2021 | Dixon |
| 2022/0313433 A1 | 10/2022 | Ma |

OTHER PUBLICATIONS

International Search Report and Written Opinion, PCT/US2021/063333, dated Jan. 13, 2022.
EPO Extended EP Search Report, EP21907641.1, dated Oct. 11, 2024, 7 pgs.
Chinese Office Action, CN202180092926.6, dated Jan. 12, 2024, 10 pgs.

* cited by examiner

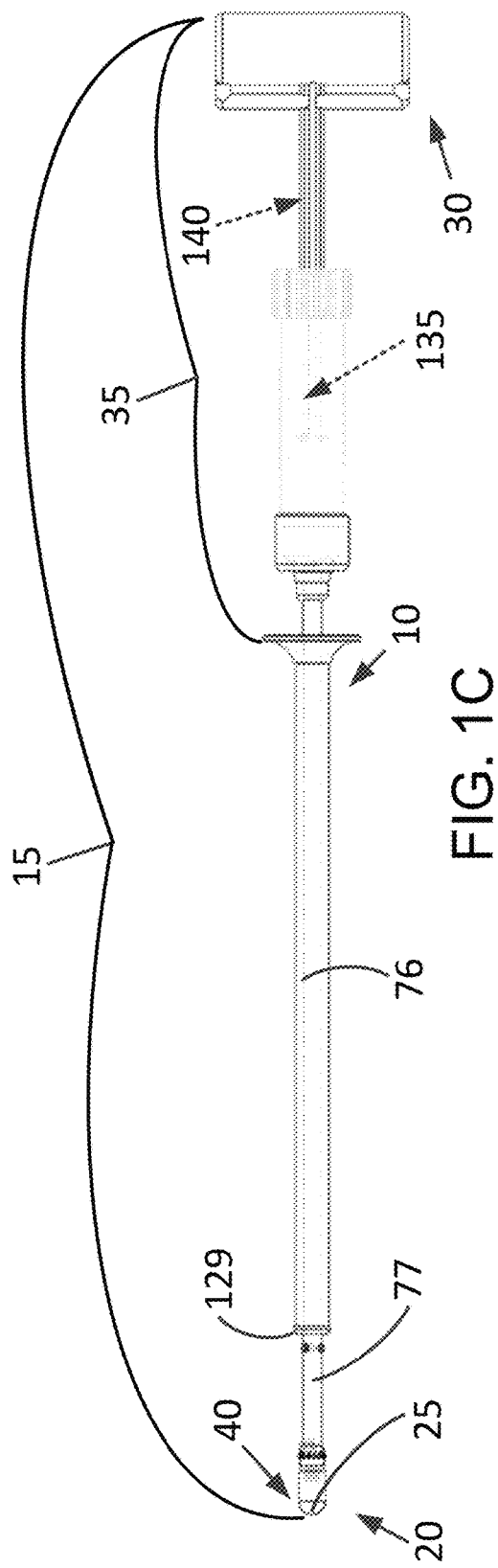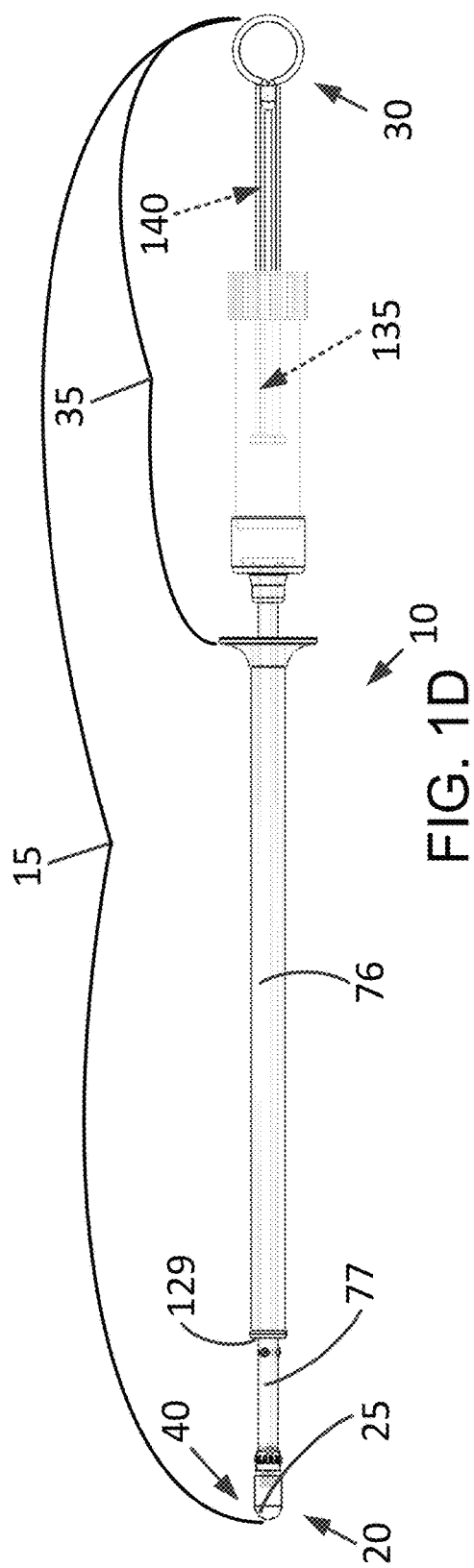

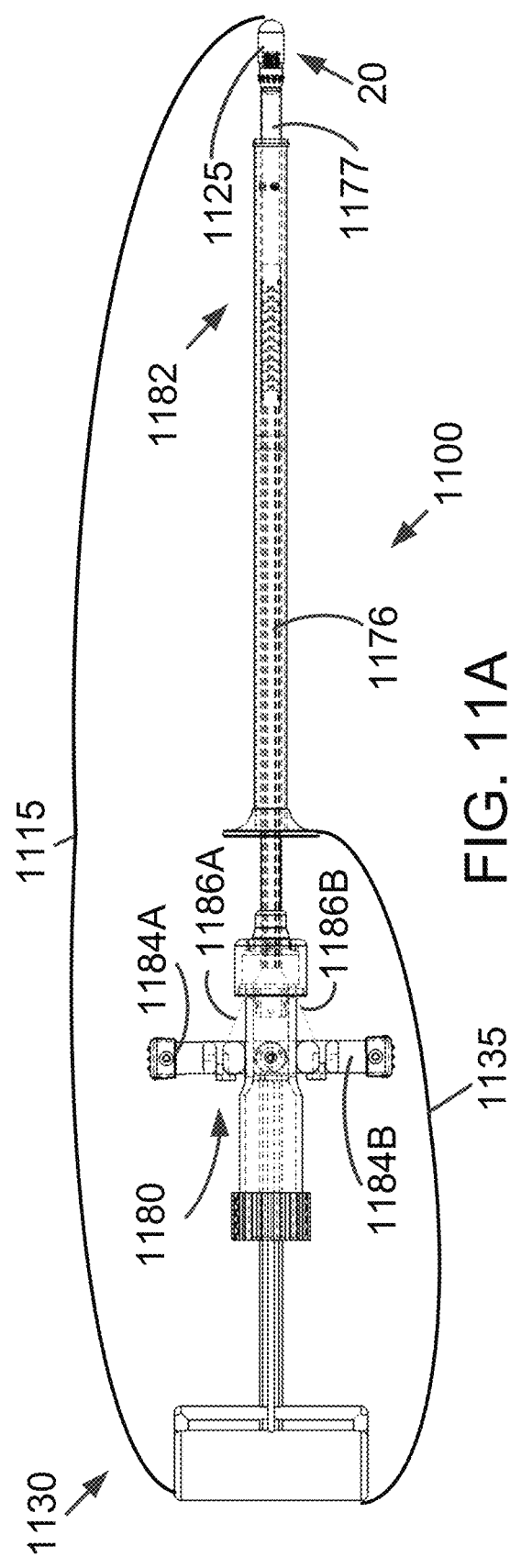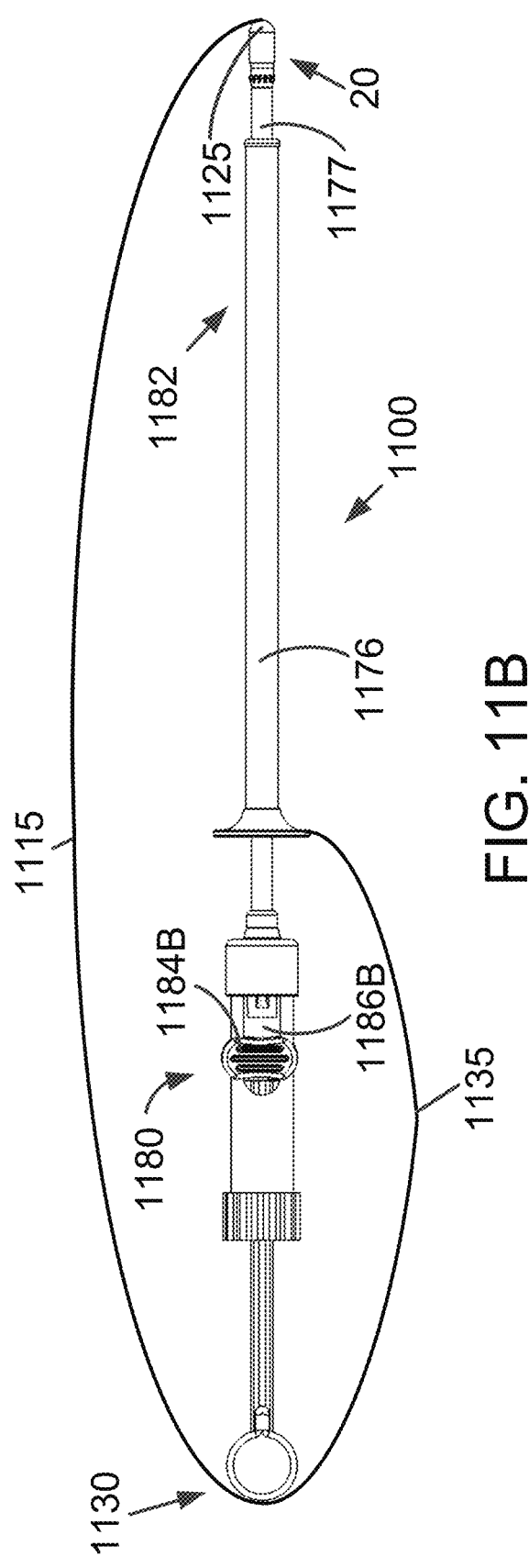

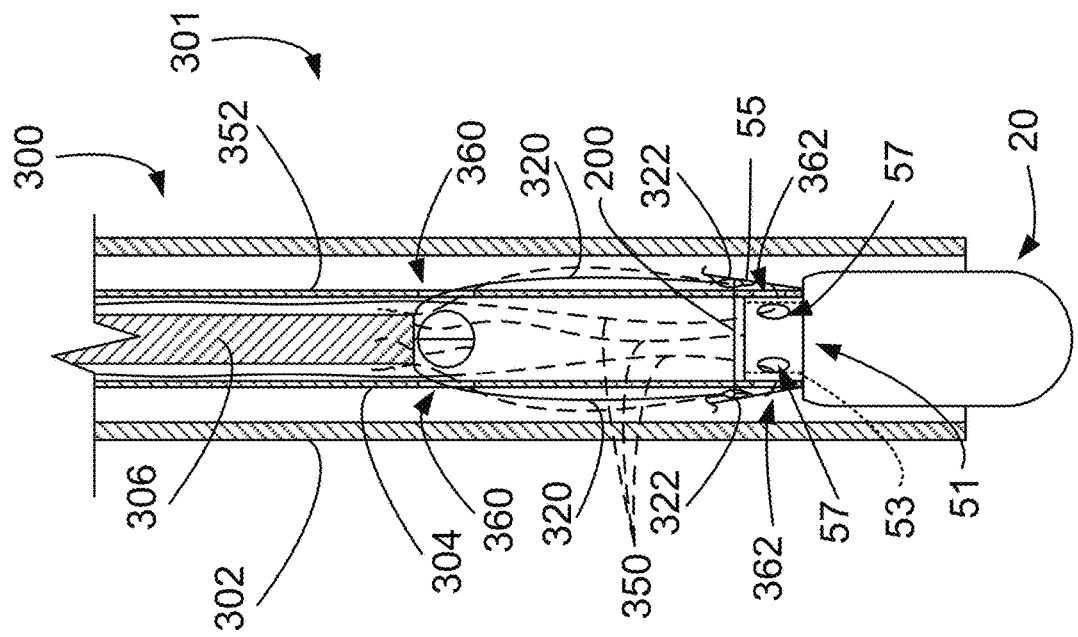
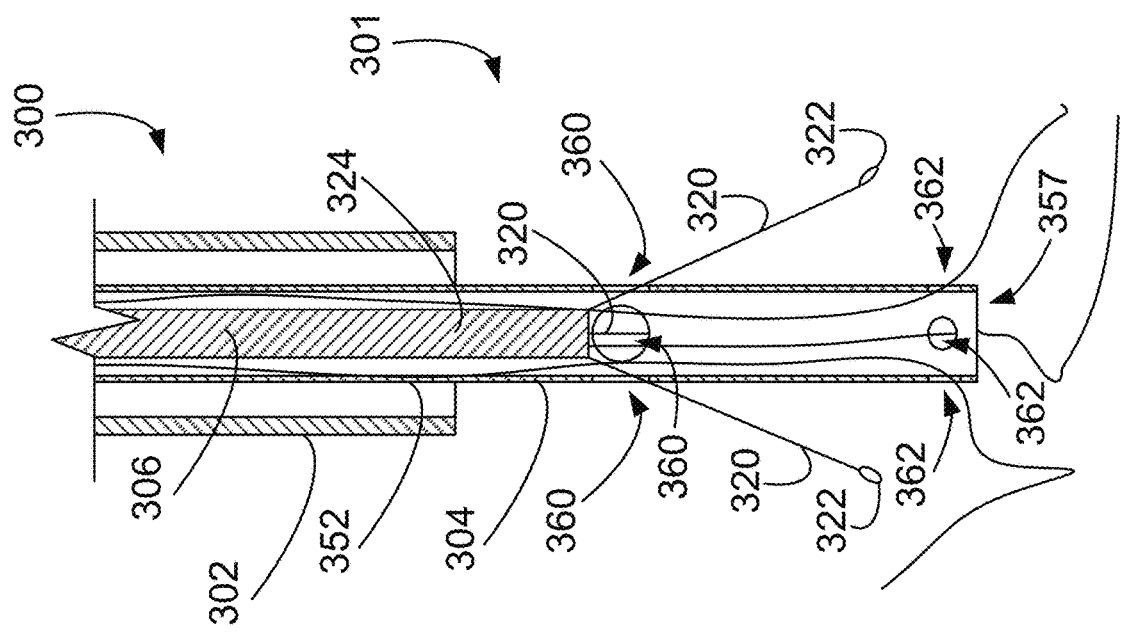
FIG. 15
FIG. 14

SYSTEM AND METHOD FOR CARDIAC VALVE REPAIR

CROSS-REFERENCE TO RELATED APPLICATIONS

This application is a continuation-in-part of application Ser. No. 17/227,847, filed Apr. 12, 2021, and titled "System and Method for Cardiac Valve Repair", which is related to and claims priority under 35 U.S.C. § 119(e) from U.S. Patent Application No. 63/125,035, filed Dec. 14, 2020, and titled "System and Method for Cardiac Valve Repair". The entire contents of each of the foregoing applications are incorporated herein by reference for all purposes.

TECHNICAL FIELD

The present disclosure relates to medical systems and methods for repairing a cardiac valve. More specifically, the present disclosure pertains to a cardiac valve repair implant that is minimally invasively deliverable and implantable via an associated minimally invasive delivery tool.

BACKGROUND

Cardiac valve regurgitation occurs when a cardiac valve does not close completely, causing blood to leak back through the valve. The causes of regurgitation may vary. Functional regurgitation is caused by changes to the heart geometry near the valve, where, for example, the heart enlarges, inducing both geometrical distortion around the valve annulus and insufficient leaflet coaptation during valve closure.

Degenerative regurgitation is caused by a disease of the valve itself, where, for example, the leaflets may thicken and be unable to seal completely. In both cases, the patient suffers because high-pressure blood in the ventricle regurgitates through the valve into the low-pressure venous system.

Surgical repair and replacement may successfully treat tricuspid and mitral regurgitation, but surgery is costly and traumatic. Specifically, the surgical treatments require general anesthesia, a stopped heart with extracorporeal bypass, and either valve replacement or repair. The surgical treatments require painful recovery over a period of approximately three weeks. As a result, surgical treatment is often not performed because cost, recovery time, pain, and, for older patients, mortality risk may be prohibitive.

Cardiac valves may also be repaired via percutaneous systems and methods. For example, a percutaneous treatment may navigate a Nitinol clip between the valve leaflets to permanently clip the leaflets together. The percutaneous clip procedure results in a relatively pain-free recovery within days, and this procedure has successfully treated hundreds of thousands mitral regurgitation patients. Unfortunately, the percutaneous clip procedure is costly and difficult to perform, particularly by inexperienced operators. Further, the feasibility of the percutaneous clip procedure for the tricuspid valve is unproven and may be less effective in a three-leaflet valve. In addition, the mechanisms of valvular regurgitation are multiple and fixing a single mechanism of disease (e.g., leaflet grasping) may temporarily reduce the severity of regurgitation but not improve the natural history of the disease (e.g., deterioration over time).

Accordingly, there is a need for a system for repairing a cardiac valve that is simple to deliver, targets several disease components simultaneously, and improves overall results as compared to conventional treatments. There is also a need for a method of making such a repair.

BRIEF SUMMARY

Aspects of the present disclosure may include a cardiac valve repair implant. The cardiac valve repair implant includes an occlusive assembly including an inner sheet. The implant further includes a frame coupled to the occlusive assembly and configured to transition from a collapsed state to an expanded state about the central longitudinal axis. Transitioning from the collapsed state to the expanded state causes a proximal end of the frame to expand radially outward from the central longitudinal axis. The implant also includes an outer sheet supported on a proximal portion of the frame. The occlusive assembly is supported on a distal portion of the frame such that the inner sheet extends about the central longitudinal axis and an annular opening is defined between the outer sheet and the inner sheet when the frame is in the expanded state.

In another aspect of the present disclosure, a cardiac valve repair implant is provided that includes a central occluder and a frame extending from the central occluder and supporting the central occluder on a distal portion of the frame. The frame is configured to transition from a collapsed state to an expanded state about a central longitudinal axis. A proximal end of the frame projects proximally when the frame is in the collapsed state, and the proximal end of the frame projects radially outward away from a central longitudinal axis when the frame is in the expanded state. The implant further includes an outer sheet supported on a proximal portion of the frame and an inner sheet about the central occluder. When the frame is in the expanded state, the central occluder is disposed along the longitudinal axis and an annular opening centered about the central longitudinal axis is defined between the outer sheet and the inner sheet.

In yet another aspect of the present disclosure, a method of repairing target cardiac valves is provided. The method includes delivering an implant in a collapsed state into an atrium adjacent a target cardiac valve. The implant includes an occlusive assembly with an inner sheet, a frame coupled to the occlusive assembly and an outer sheet supported on a proximal portion of the frame.

The inner sheet of the occlusive assembly is supported on a distal portion of the frame such that when the implant is in the collapsed state, the frame and the inner sheet are folded inward about a central longitudinal axis of the frame. The method further includes approaching the target cardiac valve with the implant in an expanded state, wherein when the implant is in the expanded state, the frame, the outer sheet, and the inner sheet are unfolded such that the inner sheet and the outer sheet form an annular structure defining a annular opening between the inner sheet and the outer sheet, the annular opening centered about the central longitudinal axis. The method also includes positioning the occlusive assembly in an orifice of the target cardiac valve and a distal side of the annular structure against an annular region of cardiac tissue surrounding the target cardiac valve such that the annular opening opens over the orifice of the target cardiac valve.

BRIEF DESCRIPTION OF THE DRAWINGS

FIGS. 1A-1D are illustrations of a system for repairing a cardiac valve, the system including a minimally invasive delivery tool and an implantable cardiac valve repair implant supported on a distal end of the delivery tool and that is deliverable and implantable via the delivery tool.

FIGS. 11A-11C are illustrations of a system for repairing a cardiac valve and, more specifically, a plan view, side elevation view, and a plan view illustrating a range of motion of a delivery tool of the system, respectively.

FIG. 14 is a side cross-sectional elevation view of a distal portion of the delivery tool of FIG. 13.

FIG. 15 is a side cross-sectional elevation view of a distal portion of the delivery tool of FIG. 13 coupled to the implant.

DETAILED DESCRIPTION

Figure 1A:
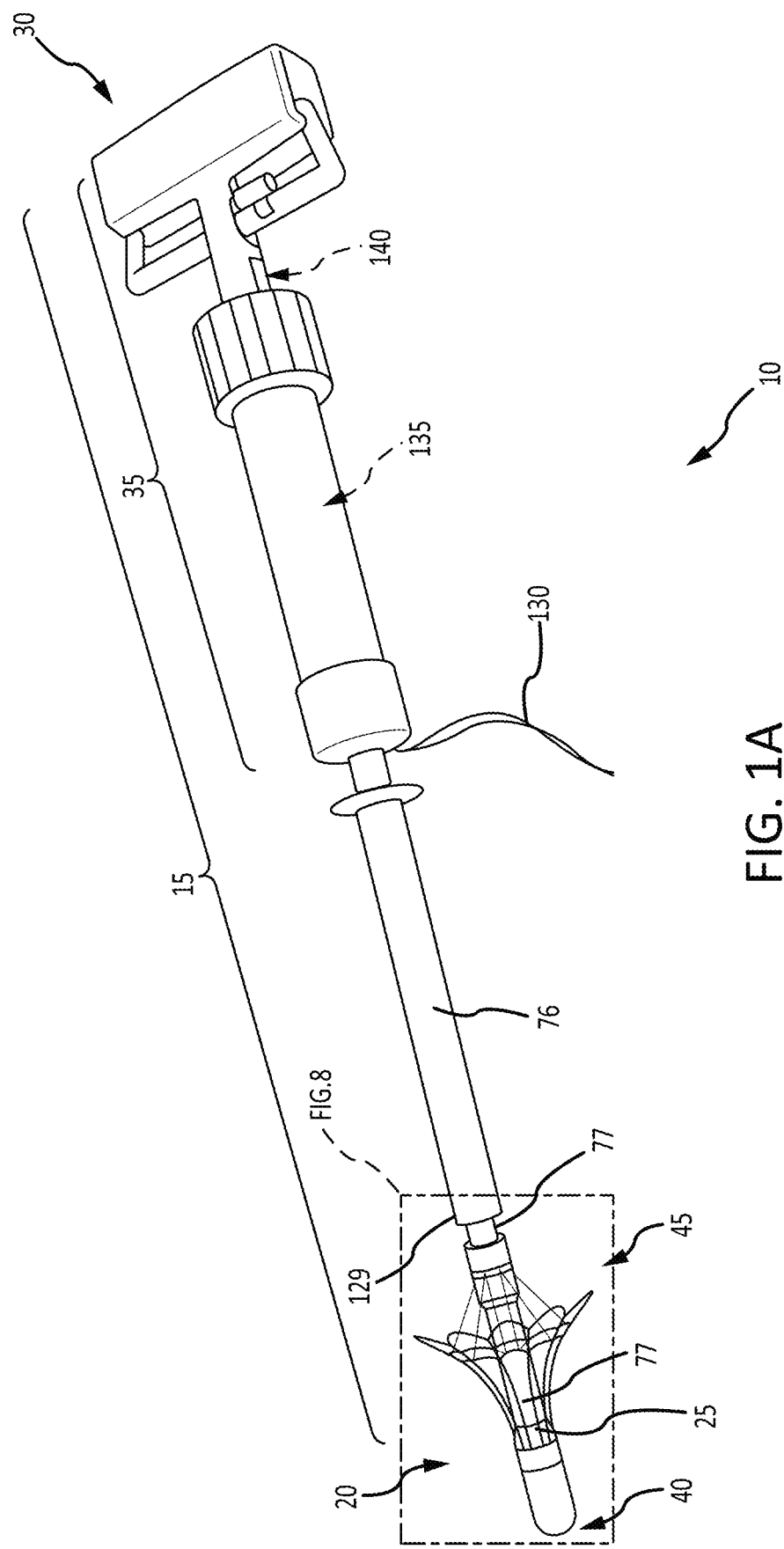
Figure 1B:
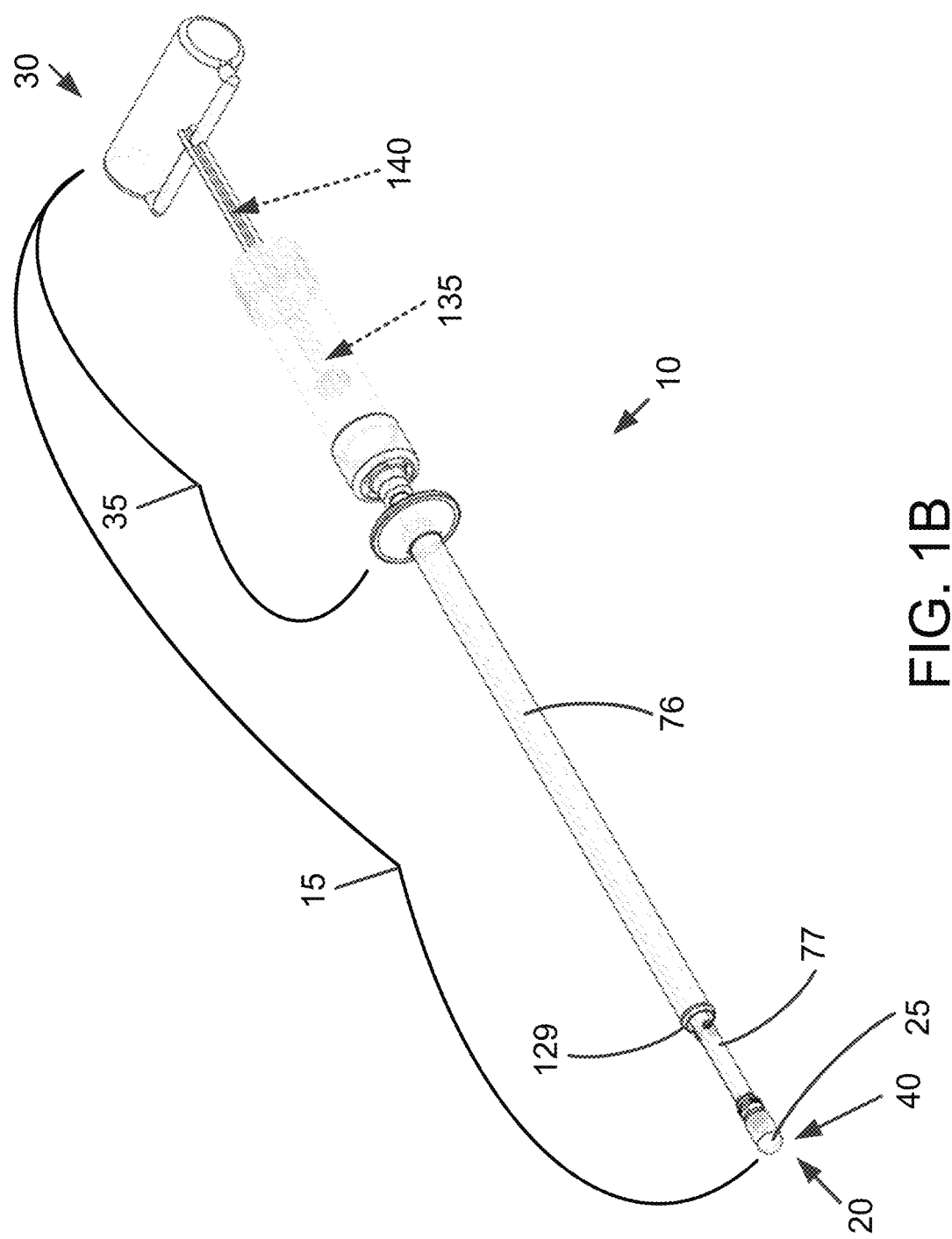

For a brief overview of the cardiac valve repair system 10 disclosed herein, reference is made to FIGS. 1A-1D. In particular, FIG. 1A is an illustration of the cardiac valve repair system 10 while FIGS. 1B-1D are isometric, plan, and side elevation views, respectively of the valve repair system 10. As can be understood from FIG. 1A, the system 10 includes a delivery and deployment tool 15 and an implantable cardiac valve repair device or implant 20 supported on a distal end 25 of the tool 15. The tool 15 includes a proximal end 30 opposite the tool distal end 25. The tool proximal end 30 includes a control handle 35 used by a physician to manipulate the tool 15 in positioning the implant 20 at the target site and deploying the implant 20 within the target site, which is a cardiac valve in need of repair, as discussed in detail later in this Detailed Description. In one embodiment, the tool 15 is used for minimally invasive delivery and deployment of the implant 20 in the cardiac valve in need of repair.

The system and its implant are advantageous in that the implant may be delivered and deployed at the target site via an antegrade percutaneous route (e.g., a trans-femoral or trans-jugular route) with the patient consciously sedated during the procedure. It is anticipated the implantation stage may take less than 60 minutes, and the implant and delivery system will have a cost substantially less expensive than prior cardiac valve repair systems. Finally, the regurgitation grade afforded by a cardiac valve repair completed via the implant 20 disclosed herein will be 2+ or lower. Accordingly, the cardiac repair system 10 is a significant improvement over prior art systems as it is atraumatic, materially less expensive and less time intensive, all while providing a significant improvement in the reduction of regurgitation.

I. Cardiac Valve Repair Implant

To begin a detailed discussion of the cardiac valve repair implant 20, reference is made to FIGS. 2-6, which are various views of an embodiment of the implant 20 when the implant is in an expanded state that exists when the implant is implanted in the cardiac valve to be repaired. As illustrated in these figures, the implant includes distal end 40 and a proximal end 45. The distal end 40 serves as the leading end of the implant 20 during implantation, as can be understood from FIG. 1A-1D.

As illustrated in FIGS. 2-6, the implant 20 further includes a central occluder 50, a frame 55 and a thin sheet 60 (also referred to herein as a thin layer 60) supported on the frame. The frame 55 extends proximally from a proximal end 65 of the central occluder 50. When in the expanded state, the frame 55 radiates laterally outwardly relative to a central longitudinal axis 70 (see FIG. 5) of the implant 20, and the thin sheet 60 forms an annular surface 62 supported on the expanded frame 55. The annular surface 62 has a distal radially inward edge 63 and a proximal radially outward edge 64. The distal radially inward edge 63 defines a central opening 66 in the thin sheet 60 and the implant 20. The proximal radially outward edge 64 forms the extreme proximal radially outward boundary of this embodiment of the implant when in the expanded state. The central longitudinal axis 70 passes through the extreme distal tip 75 of the central occluder 50 and a center point 80 (see FIG. 4) of the proximal end 65 of the central occluder. In light of the foregoing and in at least certain embodiments, the frame 55 is generally designed to sit on the floor of the atrium, to induce annular reduction, and to produce a neo-annulus.

Figure 10:
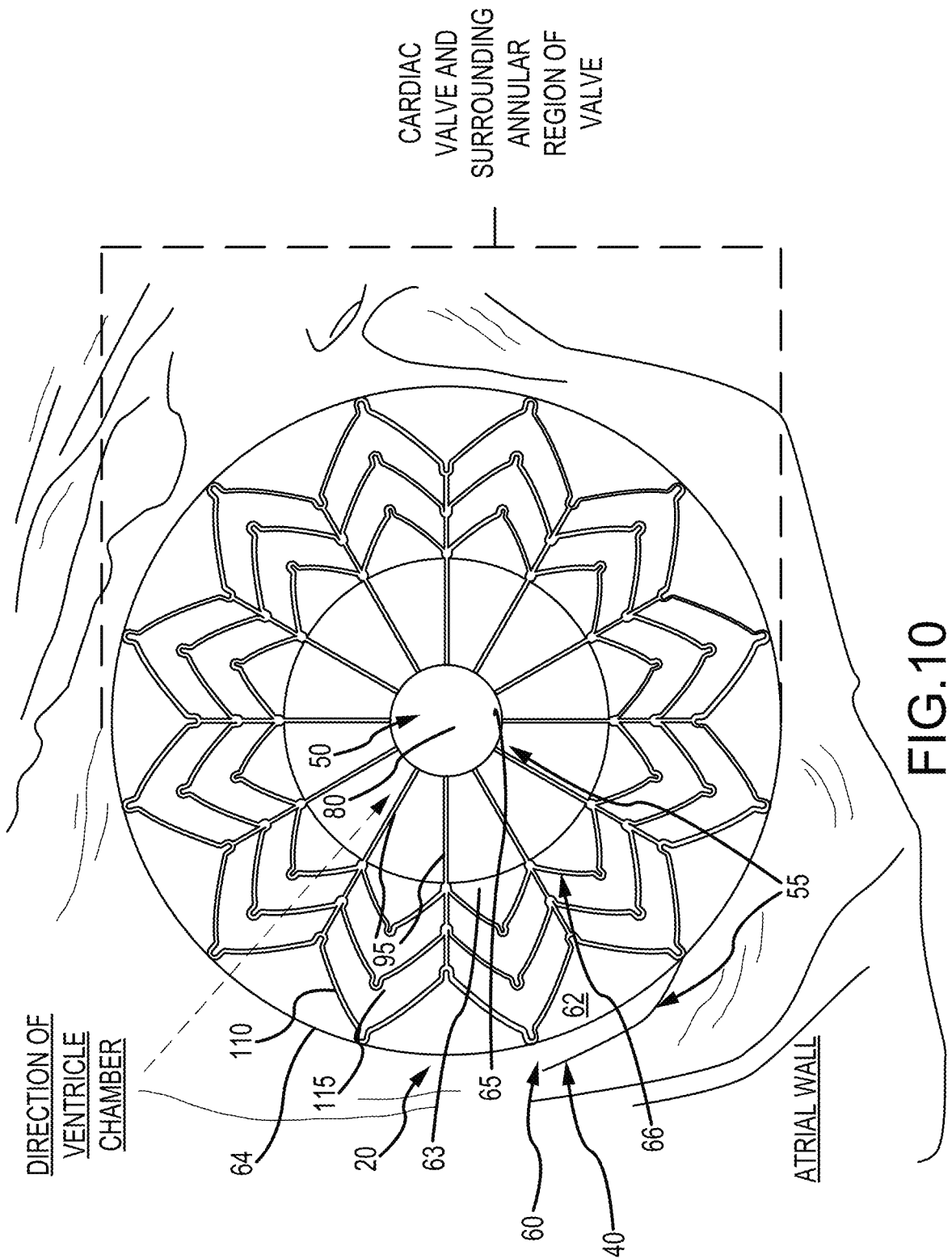
FIG. 10 is a view of the implantable cardiac valve repair implant implanted in a target cardiac valve, as viewed from an atrial position looking towards the valve and the ventricle chamber below.

As can be understood from FIGS. 2-6, in addition to being annular, the annular surface 62 may also be conical, or relatively so (e.g., parabolic), such that its proximal side, which faces the atrial chamber when the implant 20 is implanted in the target cardiac valve as depicted in FIG. 10, serves as a funnel arrangement distally leading from the atrial chamber towards the central opening 66 of the implant 20 and the valve opening distal the central opening 66. Similarly, the distal side of the annular surface 62 may also be conical to generally make mating surface contact with the semi-conical regions of the atrial wall surface and surrounding annular region of the target cardiac valve, as can be understood from FIG. 10.

Figure 6:
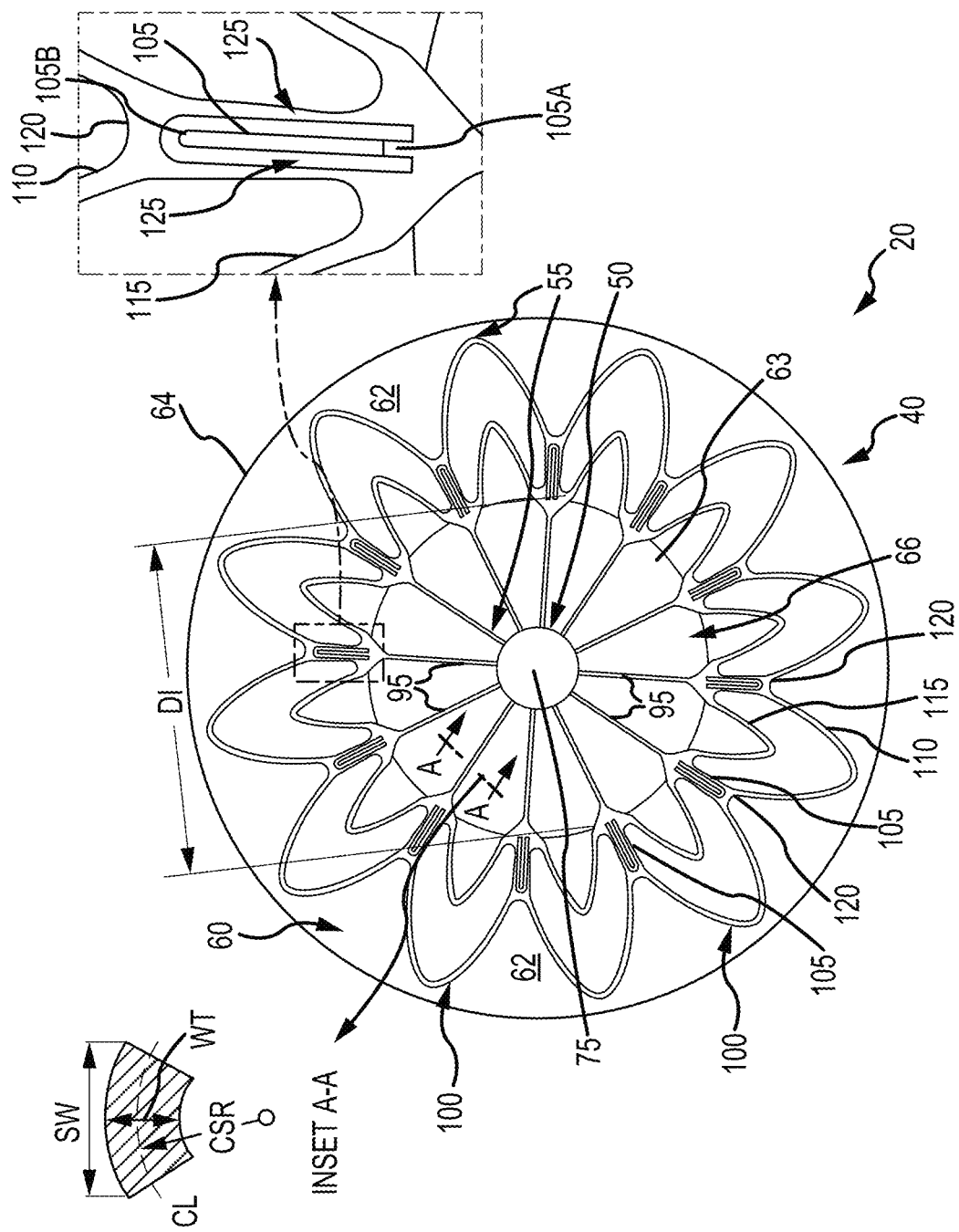
FIG. 6 is a distal plan view of the implantable cardiac valve repair implant in the expanded state.
Figure 7:
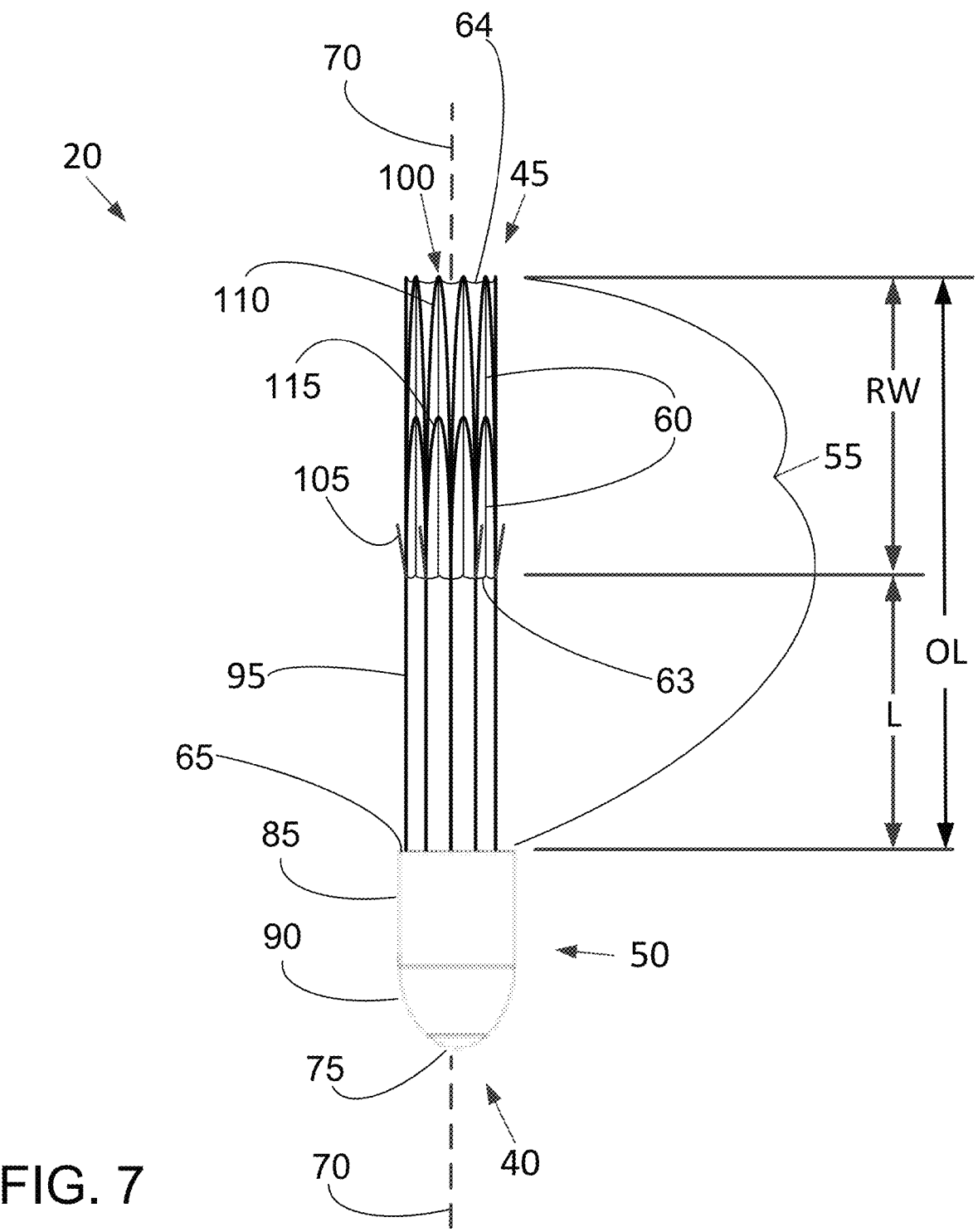
FIG. 7 is a side elevation view of the implantable cardiac valve repair implant in a collapsed state.

When in the collapsed state, as depicted in FIG. 7, which is a side view of the implant collapsed to allow its delivery to the target site via the tool 15, the frame 55 and thin sheet 60 collapse symmetrically about the central longitudinal axis 70. Thus, a comparison of the implant 20 in FIGS. 2-6 when in the expanded state to the implant 20 in FIG. 7 in the collapsed state indicates that the implant can transition from the collapsed state to the expanded state similar to an umbrella.

As can be understood from FIG. 9 and discussed in greater detail later in this Detailed Disclosure, during delivery, the implant 20 is maintained in the collapsed state of FIG. 7 by the tool 15 so as to allow the implant to be negotiated through the patient vascular system and into an atrial chamber of the heart for implantation of the implant within a target cardiac valve. For example, with the implant 20 maintained in the collapsed state by virtue of being confined within a tubular sheath 76 of the delivery tool 15, the implant may be delivered and deployed at the target site via an antegrade percutaneous route (e.g., an antegrade trans-femoral or trans-jugular route) with the patient consciously sedated during the procedure.

Upon being properly positioned in the target cardiac valve for repair, the physician actuates the tool 15 such that the tool no longer maintains the implant 20 in the collapsed state, as can be understood from FIG. 1A. Since the frame 55 of the implant 20 is biased to self-expand into the expanded state of FIGS. 2-6, the implant self-expands into the expanded state to anchor itself within the target cardiac valve and reduce regurgitation, as shown in FIG. 10.

Returning to FIGS. 2-6, it can be understood that the central occluder 50 may take the form of a bullet or conical shape. In doing so, the central occluder may have a cylindrical side 85 extending distally from the central occluder proximal end 65 and then transitioning to a bullnose 90 that distally extends to the central occluder extreme distal tip 75. Such a bullet or conical shape results in the central occluder 50 being atraumatic for delivery and implantation purposes. Further, such a shape facilitates the cylindrical side 85 of the central occluder substantially sealing against the cardiac valve leaflets, thereby materially reducing, if not eliminating, central regurgitation past the cardiac valve leaflets.

Without limitation and depending on the embodiment, the central occluder 50 may be formed from polytetrafluoroethylene (PTFE), polyether ether ketone (PEEK), acetal, silicone, nylon, polyethylene, polypropylene, polyethylene terephthalate (PET), polyurethane, or other thermoplastic elastomers. In certain embodiments, the material of the central occluder 50 may be angio- and/or echolucent.

In certain embodiments, the central occluder 50 may be filled with saline, a combination of saline with a radiopaque contrast agent, or other fluid. In such embodiments, the central occluder 50 may be delivered in a first configuration having a reduced diameter and then expanded into a second configuration having an increased diameter by introducing fluid into the central occluder 50 following delivery. The amount of saline delivered during implantation may be determined in real-time, for example, by monitoring a size of the central occluder 50, e.g., using an X-ray image, and/or by monitoring a reduction of regurgitation, e.g., using ultrasound imaging.

Figure 5:
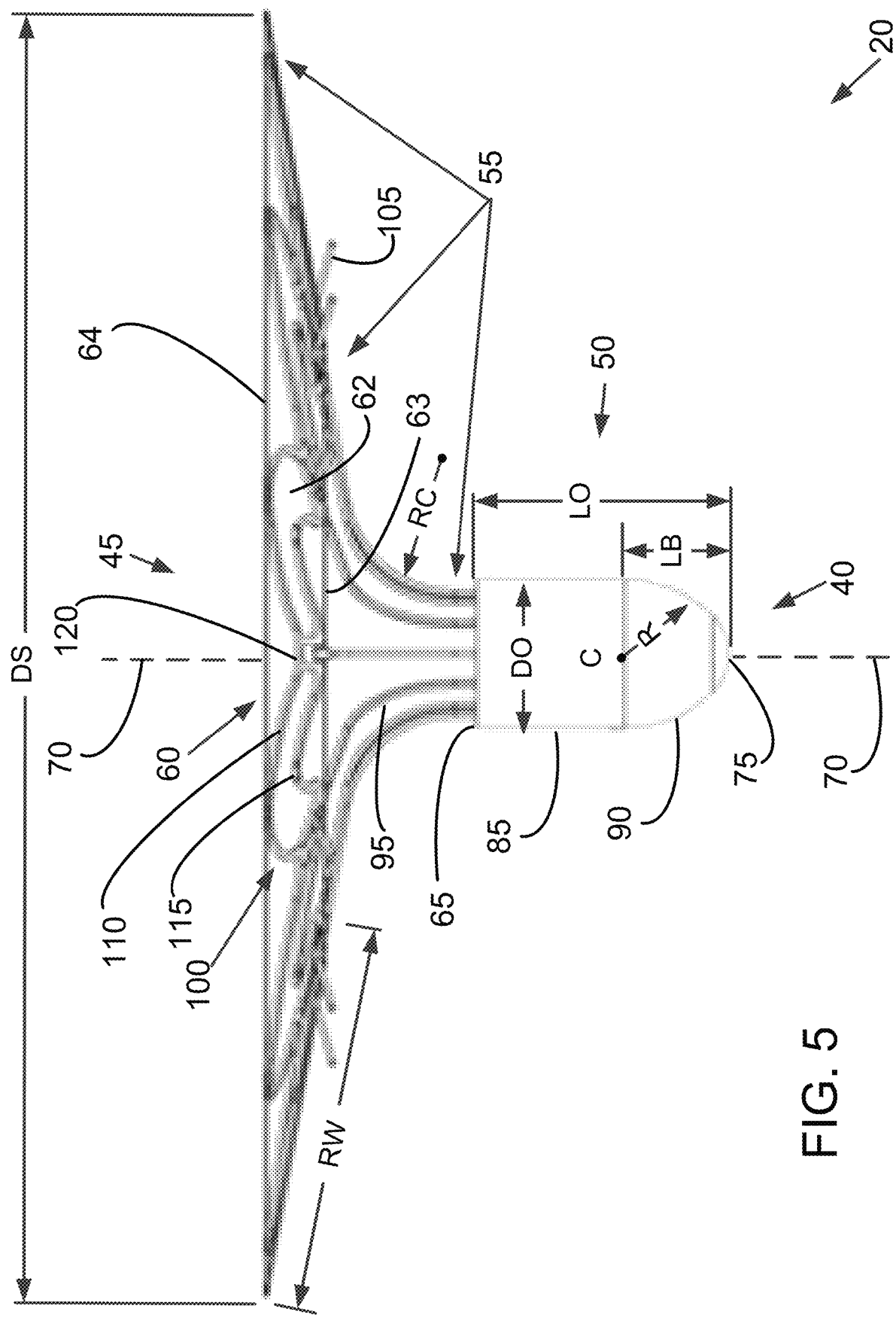
FIG. 5 is a side elevation view of the implantable cardiac valve repair implant in the expanded state.

In certain embodiments and without limitation, the central occluder 50 may be formed from a material having a durometer from and including 10 A to and including 100 D, from and including 10 D to and including 100 D, or from and including 40D to and including 80 D. In one specific embodiment, the material of the central occluder 50 has a durometer of 80 D. As indicated in FIG. 5, the central occluder may have an overall diameter DO that, in certain embodiments and without limitation, may be between approximately 5 millimeters (mm) and approximately 25 mm, between approximately 5 mm and approximately 15 mm, or between approximately 8 mm and approximately 12 mm. The central occluder 50 further has an overall length LO from its proximal end 65 to its extreme distal tip 75 that, in certain embodiments and without limitation, may be between approximately 5 mm and approximately 40 mm or between approximately 10 mm and approximately 20 mm. The bullnose 90 may have a length LB that, in certain embodiments and without limitation, may be between approximately 2.5 mm and approximately 12.5 mm, between approximately 2.5 mm and approximately 7.5 mm, or between approximately 4 mm and approximately 6 mm. In certain embodiments and without limitation, the radius of curvature R of the bullnose 90 may be between approximately 2.5 mm and approximately 12.5 mm, between approximately 2.5 mm and approximately 7.5 mm, or between approximately 4 mm and approximately 6 mm. The general shape of the bullnose 90 may also vary across embodiments. For example, the bullnose 90 may have any of a parabolic profile, a conical profile, a spherical profile, or any other atraumatic profile. In other example embodiments, the bullnose 90 may have a trihedral, frustoconical shape, or other non-rounded shape. In certain example embodiments, the central occluder 50 may have a triangular or tri-lobe shape that provides surfaces for sealing against respective leaflets. In yet another example, the central occluder 50 may have a rounded double-concave shape. In still other embodiments, the central occluder 50 may be configured to allow distention of a distal portion of the frame 55, thereby facilitating reintervention (e.g., valve implantation). In yet other embodiments, the central occluder 50 may include a frame (e.g., inner struts) covered in a flexible material, such as, but not limited to expanded polytetrafluoroethylene (ePTFE), polyester fabric, or a similar material. In such embodiments, the flexible covering may allow the central occluder 50 to be compressed for delivery but to expand once positioned in the native valve to occlude and reduce regurgitation.

As can be understood from FIG. 5, in one embodiment, the central occluder 50 may have an overall diameter DO of approximately 10 mm, and its overall length LO may be approximately 16 mm. Additionally, the bullnose 90 may have an overall length LB of approximately 5 mm, and the radius of curvature of the bullnose 90 may or may not gradually transition over its length LB from proximal to distal. For example, the radius of curvature R may have a maximum value from approximately 2.5 mm to approximately 15 mm as measured from a center of curvature C to the distal tip 75 of the central occluder 50 but may transition to a radius of curvature R that is between approximately 2.5 mm and approximately 10 mm, but less than or equal to the maximum, at a location proximal the distal tip 75. In one embodiment, however, the bullnose 90 may have a constant radius of curvature of approximately 5 mm.

As can be understood from FIGS. 2-6, the thin sheet 60 is supported on the frame 55 and secured thereto. For example and without limitation, in certain embodiments the thin sheet 60 may be secured to the frame 55 by suturing the skirt against an inner surface and/or an outer surface of the frame 55. In other implementations, the thin sheet 60 may include a cuff or similar folded structure that is folded over an end of the frame 55. In still other implementations, the thin sheet 60 may be secured to the frame by sewing, welding, gluing/adhering, stapling, or any other suitable securement method or combination of securement methods. Depending on the embodiment, the thin sheet 60 may be on the distal side of the frame 55, the proximal side, or both such that the frame extends through and along the thin sheet. In one embodiment, the frame 55 is covered with a thin sheet 60 on the distal side of the frame where the frame contacts atrial tissue when the implant 20 is implanted in the target cardiac valve.

Depending on the embodiment, the thin sheet 60 may be formed of or include a woven or knit material or fabric that encourages tissue ingrowth. The porosity of the fabric of the thin sheet 60 assists in reducing commissural tricuspid regurgitation. Further reduction of commissural tricuspid regurgitation is provided by the angulation of the frame 55, which provides close contact with the commissures in a circumferential manner. For example, with the implant 20 implanted in the target cardiac valve, tissue in-growth into the fabric of the thin sheet 60 buttresses the myocardium, helping to keep the tissue from expanding further and reducing the potential of future regurgitation.

The fabric can be made from various methods, i.e. knitting, weaving, single or multiple layers. These fabrics can be laminated together with a polymer to make a composite structure, i.e. two pieces of knit (high porosity) with a polymer coating like silicone or urethane. Example materials for the woven or knit materials may include, without limitation, polyester, polypropylene, polyethylene, etc. The thin layer 60 may have a material thickness of between approximately 0.03 mm and approximately 1 mm, between approximately 0.05 mm and approximately 0.2 mm, or between approximately 0.07 mm and approximately 0.12 mm. In one example embodiment, the thickness of the thin layer 60 is approximately 0.2 mm. In another example embodiment, the thickness of the thin layer 60 is approximately 0.55 mm. In one embodiment, an additional textile layer may be added on the proximal side of the thin sheet 60 to create a smooth surface to minimize clot formation in an atrial chamber immediately adjacent the cardiac valve in which the implant 20 is implanted.

As indicated in FIGS. 5, 6 and 7, the thin sheet 60 has an outer diameter DS. In certain embodiments, the outer diameter DS may be between approximately 40 mm and approximately 80 mm, between approximately 50 mm and approximately 70 mm, or between approximately 55 mm and approximately 65 mm. The thin sheet 60 has a radial width RW. In certain embodiments, the radial width RW may be between approximately 10 mm and approximately 30 mm, between approximately 13 mm and approximately 23 mm, or between approximately 17 mm and approximately 19 mm. The thin sheet 60 has a central opening 66 with an inner diameter DI. In certain embodiments, the inner diameter DI may be between approximately 20 mm and approximately 60 mm, between approximately 25 mm and approximately 45 mm, or between approximately 28 mm and approximately 32 mm. For example, In one embodiment, the thin sheet 60 has an outer diameter DS of approximately 60 mm, a radial width RW of approximately 18.2 mm, and a central opening 66 with an inner diameter DI of approximately 30 mm. Due to its configuration, when the implant 20 is implanted in the target cardiac valve, the circumferential fabric of the thin sheet 60 covers a portion of the outer leaflet commissures to block leaks at the edges of the commissures.

As shown in FIGS. 2-6, the frame 55 includes spokes 95, arcuate petal portions 100 and protruding anchor members 105. The frame 55 may be made from a variety of super-elastic and/or shape memory materials, including, for example, nickel-titanium alloys (e.g., Nitinol), which may be laser cut from a tube or in the form of drawn wire. The features defined in the shape memory materials may be defined therein via various cutting methods known in the art, include laser, water jet, electrical discharge machining (EDM), stamping, etching, milling, etc.

In one embodiment, the frame 55 is made of super-elastic, shape memory nickel titanium alloy (e.g., Nitinol). Regardless of which shape memory material is employed, the shape memory aspects of the frame 55 allow the frame and, as a result, the implant 20 to self-bias from the collapsed state (see FIG. 7) to the expanded state (see FIGS. 2-6) when not physically maintained in the collapsed state by the delivery tool 15.

In various embodiments, the frame 55, central occluder 50 and the rest of the implant 20 remain implanted as a unit in the target cardiac valve. In other words, the implant 20 is implanted and remains so as configured in FIGS. 2-6.

There may be situations where it is desirable to remove the central occluder and then implant a replacement valve in the target cardiac valve. Accordingly, in alternate embodiments, the central occluder 50 and frame spokes or struts 95 may be removable after implantation, leaving the surrounding annular surface 62 of the implant in place, the annular surface 62 being formed by and including the frame arcuate petal portions 100 and the thin sheet 60 supported thereon. In such embodiments, a circumferential suture connection may exist between the spokes 95 and the rest of the frame 55 radially outward of the spokes 95. Thus, this circumferential suture connection may be cut and the central occluder 50 and its spokes 95 may be removed through a catheter, leaving the annular portion of the implant, which then acts as an "annuloplasty" frame.

As indicated in FIG. 7, when the implant 20 is in the collapsed state, the spokes 95 proximally extend from the proximal end 65 of the central occluder 50 to the arcuate petal portions 100. In doing so, the spokes 95 are substantially parallel with, and extend along and near to, the central longitudinal axis 70 of the implant 20. As can be understood from FIG. 7, when the implant is in the collapsed state, each spoke 95 has a length L from the central occluder proximal end 65 to a distal boundary of an arcuate petal portion 100. In certain embodiments, the length L may be between approximately 10 mm and approximately 40 mm or between approximately 15 mm and approximately 22 mm, with one embodiment having a length L of approximately 19 mm. As indicated in FIG. 7, the frame 55 in the collapsed state thus has an overall length OL that is the sum of the length L (shown in FIG. 7) and the radial width RW (shown in FIGS. 5 and 7), the candidate dimensions for the radial width RW being as discussed above with respect to FIG. 5.

As shown in FIGS. 2-6, when the implant 20 is in the expanded state, the spokes 95 proximally extend from the central occluder proximal end 65 and laterally radiate away from the central longitudinal axis 70 of the implant 20 to the arcuate petal portions 100. In doing so, the spokes 95 have a radius of curvature RC of between approximately 5 mm and approximately 20 mm, between approximately 10 mm and approximately 18 mm, or between approximately 15 mm and approximately 16 mm with one embodiment having a radius of curvature RC of approximately 15 mm, as can be understood from FIG. 5.

Depending on the embodiment, the frame 55 may include between approximately 3 and approximately 15 spokes 95. In certain embodiments, the number of spokes 95 and gaps therebetween may be selected to facilitate passage of other tools and devices past the frame 55. Embodiments may include spokes 95 with various cross-sectional shapes; however, in at least certain embodiments, spokes 95 have an annular sector cross-sectional shape, such as illustrated in Inset A-A of FIG. 6. In such embodiments, the cross-sectional shape of the spokes 95 may be defined by each of a strut width SW (defined as the maximum width of the spoke) and a wall thickness WT of the spokes 95. The spokes 95 may be further defined by a cross-sectional radius of curvature CSR as measured to a centerline CL of each spoke. In certain implementations, the wall thickness WT may be between approximately 0.2 mm and 0.8 mm, between approximately 0.3 mm and approximately 0.7 mm, or between approximately 0.4 mm and approximately 0.6 mm. In addition, in certain implementations, the spokes 95 may conform to certain spoke aspect ratios, which, in the context of the spokes 95 refers to the ratio of the wall thickness WT to the strut width SW. For example, and without limitation, embodiments may have a spoke aspect between 4:0.5 and 1:2, between 3:1 and 1:1.2, or between 2:1 and 1:1. In embodiments, the cross-sectional radios of curvature CSR may be between approximately 2 mm and approximately 6 mm, between approximately 3 mm and approximately 5 mm, or between approximately 3.5 mm and approximately 5 mm. In one particular embodiment, the frame 55 is made of Nitinol and the frame 55 has 12 spokes 95, with each spoke 95 having a wall thickness WT of approximately 0.46 mm, an aspect ratio of approximately 2:1 (resulting in a strut width SW of approximately 0.23 mm), and a cross-sectional radius of curvature CSR of approximately 5 mm. In certain embodiments, the spokes 95 may be arranged such that they extend distally from the frame 55 at an angle such that the thin sheet 60 occludes coaptation gaps. In certain embodiments of the present disclosure, each of the spokes 95 may be dimensionally identical; however, in other embodiments, one or more of the spokes 95 may differ in any of the various characteristics noted above.

As illustrated in FIGS. 2-6, each arcuate petal portion 100 is located between a pair of spokes 95 and forms a section of the circumference of a radially outward half of the expanded frame 55. As can be understood from FIG. 5, unlike the spokes 95, which are curved in the expanded state, the arcuate petal portions 100 in the expanded state are generally straight in a laterally radiating direction and have approximately the same radial width RW as that of the thin sheet 60. Each petal portion 100 has an outer arcuate member 110 and an inner arcuate member 115, both of which point radially outward. These arcuate members 110, 115 intersect at a junction portion 120 that extends from a respective spoke 95 and surrounds a protruding anchor member 105 that distally projects from a distal side of its junction portion 120.

Depending on the embodiment, the frame 55 may include different numbers of petal portions 100. For example, in certain example embodiments, the frame 55 may include between 3 and 18 petal portions 100, between 6 and 15 petal portions 100, or between 10 and 14 petal portions 100. In one embodiment, the frame 55 has 12 petal portions 100. Similarly, the frame 55 may include different numbers of protruding anchor members 105. For example, in certain example embodiments, the frame 55 may include between 6 and 60 protruding anchor members 105, between 12 and 36 protruding anchor members 105, or between 18 and 30 protruding anchor members 105. In one embodiment, the frame 55 has 24 protruding anchor members 105.

The frame 55 engages the atrial tissue via the protruding anchor members 105, which may be in the form of small barbs. The protruding anchor members 105 are designed to securely engage the atrial tissue without penetrating through the tissue or to the coronary vessels. Depending on the embodiment, the protruding anchor members or barbs 105 may be curved to slide before engaging tissue. There may be one row or multiple rows of retention barbs 105.

As indicated in the enlarged view of a junction portion 120 of FIG. 6, each protruding anchor member 105 is defined in the surrounding junction portion 120 via a slot 125 that extends around the protruding anchor member 105 such that the anchor member 105 is peninsular in the surrounding junction portion 120. A radially inward end 105A extends uninterrupted to the rest of the surrounding junction portion 120 and is opposite a radially outward free end 105B of the anchor member 105, the radially outward free end 105B forming a tip of the protruding anchor member 105. As can be understood from FIGS. 2, 3 and 5, the radially outward free end of the anchor member projects distally from the rest of the frame 55.

Depending on the embodiment, each protruding anchor member 105 may have a length of between approximately 0.5 mm and approximately 6 mm, between approximately 1 mm and 4 mm, or between approximately 1 mm and approximately 3 mm. Similar to the spokes 95, the protruding anchor members 105 may have various cross-sectional shapes. In at least certain embodiments, the protruding anchor members 105 have an annular sector cross-sectional shape, similar to that discussed above in the context of the spokes 95 and as illustrated in Inset A-A of FIG. 6 and which is referenced for purposes of the following discussion. Like the spokes 95, the cross-sectional shape of the protruding anchor members 105 may be defined by each of a strut width SW (defined as the maximum width of the spoke) and a wall thickness WT. The protruding anchor members 105 may be further defined by a cross-sectional radius of curvature CSR as measured to a centerline CL of each anchor member. In certain implementations, the wall thickness WT may be between approximately 0.2 mm and 0.8 mm, between approximately 0.3 mm and approximately 0.7 mm, or between approximately 0.4 mm and approximately 0.6 mm. In addition, in certain implementations, the protruding anchor members 105 may conform to certain aspect ratios between the wall thickness WT to the strut width SW. For example, and without limitation, protruding anchor members 105 according to certain embodiments may have an aspect between 4:0.5 and 1:2, between 3:1 and 1:1.2, or between 2:1 and 1:1. In certain embodiments, the cross-sectional radios of curvature CSR may be between approximately 2 mm and approximately 6 mm, between approximately 3 mm and approximately 5 mm, or between approximately 3.5 mm and approximately 5 mm. Each protruding anchor member 105 has a wall thickness WT of approximately 0.46 mm, an aspect ratio of approximately 2:1 (resulting in a strut width SW of approximately 0.23 mm), a cross-sectional radius of curvature CSR of approximately 5 mm, and a length of approximately 1.5 mm. In certain embodiments of the present disclosure, each of the protruding anchor members 105 may be dimensionally identical; however, in other embodiments, one or more of the protruding anchor members 105 may differ in any of the various characteristics noted above.

Figure 2:
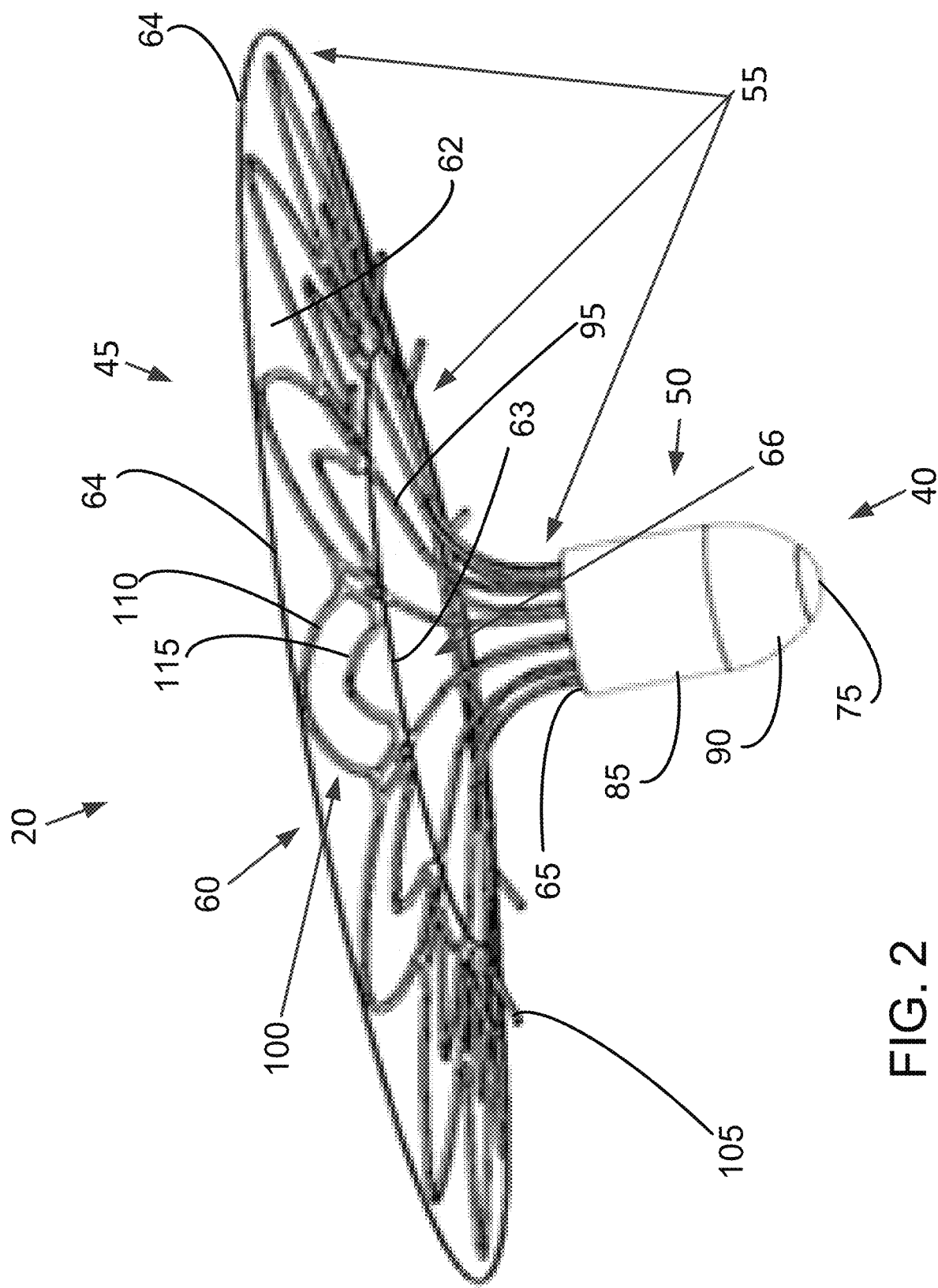
FIG. 2 is a perspective distal-side view of the implantable cardiac valve repair in an expanded state that is used when the implant is implanted in the cardiac valve.
Figure 3:
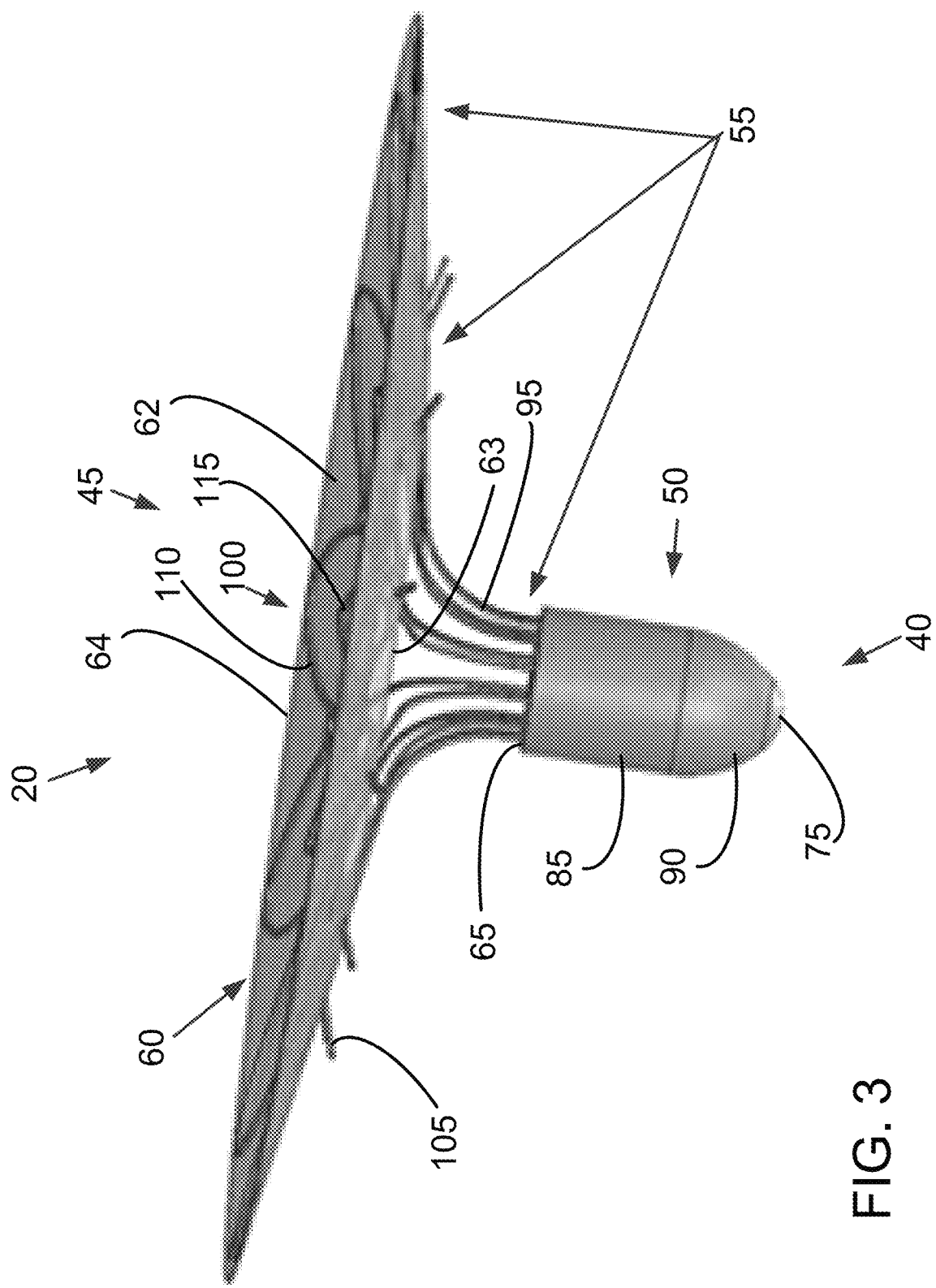
FIG. 3 is a perspective proximal-side view of the implantable cardiac valve repair implant in the expanded state.
Figure 4:
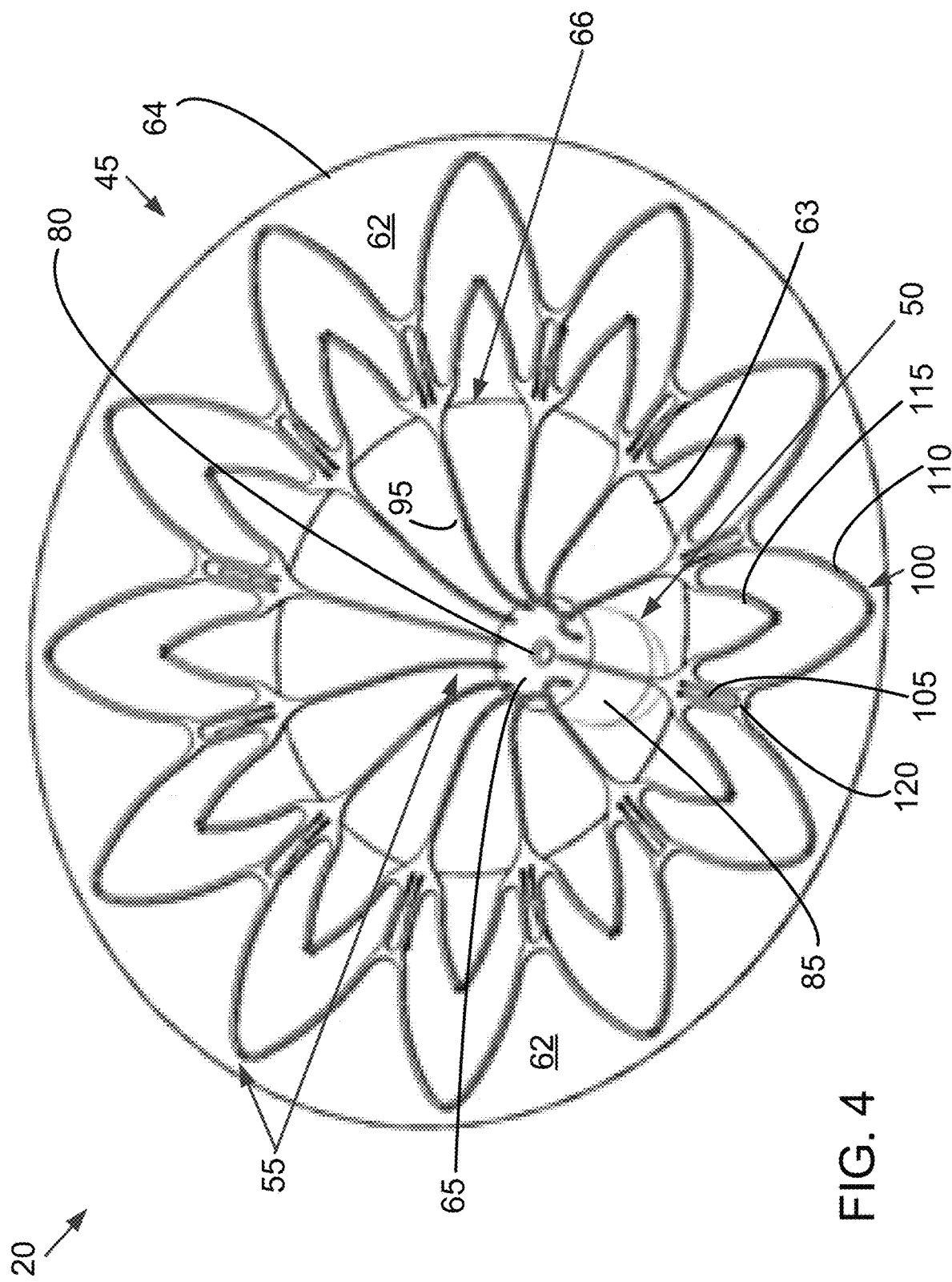
FIG. 4 is a perspective proximal-end view of the implantable cardiac valve repair implant in the expanded state.

In one embodiment, as can be understood from FIGS. 2, 3 and 5, the protruding anchor members or barbs 105 are oriented distally and radially outward. As a result, as the frame 55 is pushed towards the ventricle, the anchor members 105 slide along the atrial tissue. Ventricular pressure pushes the implant 20 towards the atrium, embedding the anchors or barbs 105 into the atrial tissue.

In an alternate embodiment, the anchors or barbs 105 are directionally reversed such that they project distally and radially inward. In this alternative embodiment, the delivery system over-expands the frame 55 during delivery and when the frame is released from the delivery system with the frame 55 in contact with tissue, the anchors or barbs 105 engage the atrial tissue as the frame 55 contracts to its relaxed state.

II. Delivery Tool and Method of Implantation

As illustrated in FIGS. 1A-1D, the delivery tool 15 includes a proximal end 30, a distal end 25 opposite the proximal end, a control handle 35, a tubular sheath 76, and a catheter 77. The control handle 35 extends distally from the proximal end 30 and is used by a physician to manipulate the tool 15 in positioning the implant 20 at the target site and deploying the implant 20 within the target cardiac valve in need of repair. The sheath 76 and catheter 77 extend distally away from the control handle 35 towards the distal end 25 of the tool 15. The catheter 77 extends longitudinally through the sheath 76, the distal end 25 of the catheter 77 forming the distal end 25 of the tool 15. The sheath 76 is used to minimize tissue trauma while the catheter 77 and implant 20 are advanced to the implantation site. Thus, the delivery tool 15 is designed to deliver the implant 20 to the implantation site, position the implant in the target cardiac valve, and control the opening of the frame 55 of the implant 20, all in an atraumatic manner.

Figure 8:
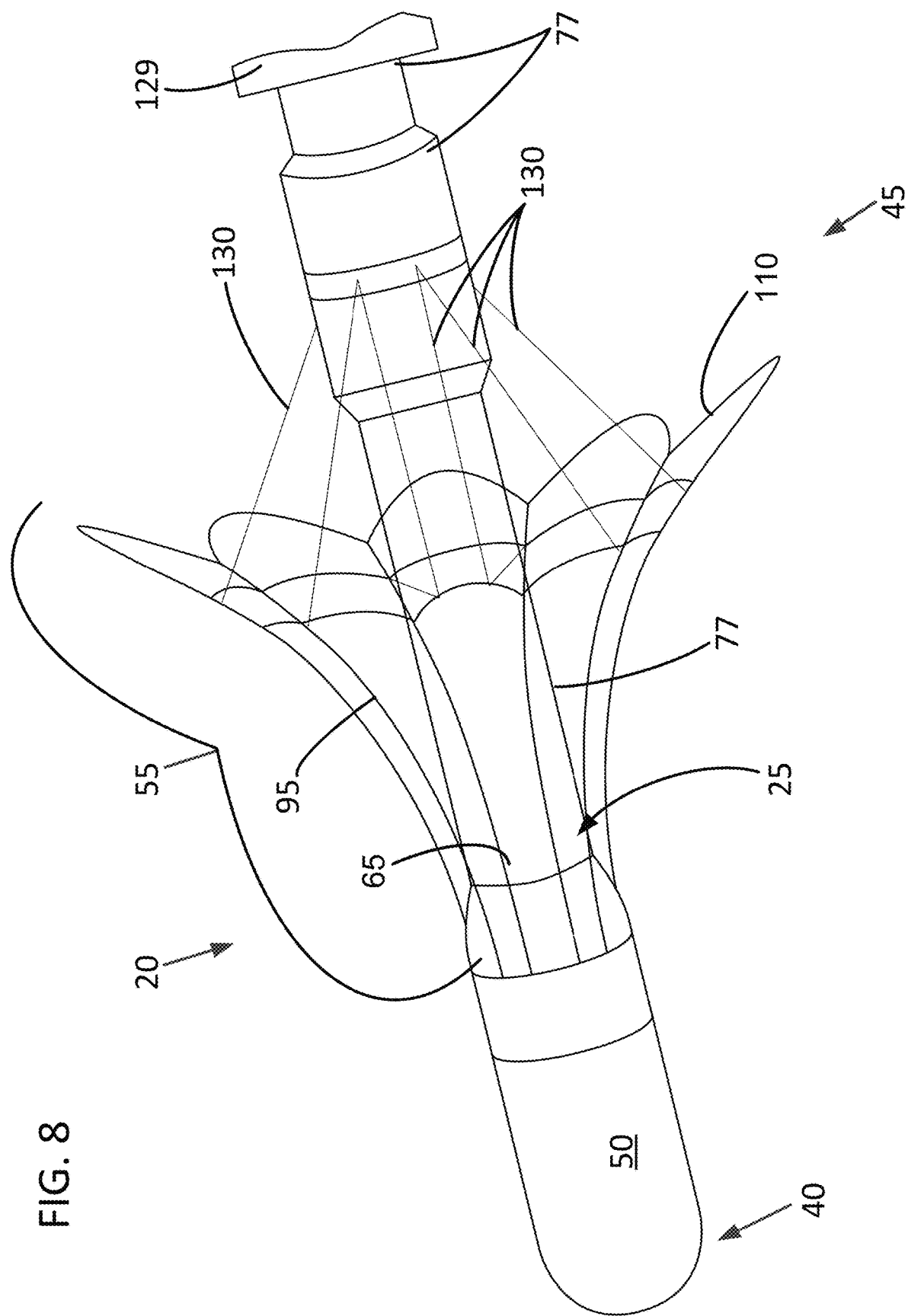
FIG. 8 is an enlarged view of the distal region of the cardiac repair system of FIG. 1A.

As depicted in FIG. 8, which is an enlarged view of the distal region of the cardiac repair system 10 of FIG. 1A, sutures 130 extend between a distal region of the catheter 77 and points of connection on the frame 55 of the implant 20. The sutures 130 further extend from the distal region of the catheter up into the handle 35 and, in one embodiment, may even extend out of the handle, as shown in FIG. 1A. Depending on the embodiment, the control sutures 130 could be replaced by cables or wire.

As can be understood from FIGS. 1A and 8, before the implant 20 is completely freed of the delivery tool 15, the sutures 130 can be manipulated via the handle 35 of the tool 15 to control the opening of the implant frame 55. Suture actuation may have one or two speeds, which may be in the form of a slow speed and/or a fast speed. The slower speed may be controlled by a spooling mechanism or a lead screw mechanism 135 within the handle. The fast speed may be controlled by a plunger style linear actuator 140 within the handle. The sutures 130 may be routed within the handle 35 to provide a 2-to-1 mechanical advantage to facilitate increased precision of control when deploying the implant 20.

The catheter 77 may employ steering via selective actuation (e.g., tension increase/decrease) of certain sutures to better control the position of the implant during deployment. This steering feature may be controlled at the handle 35.

Figure 9:
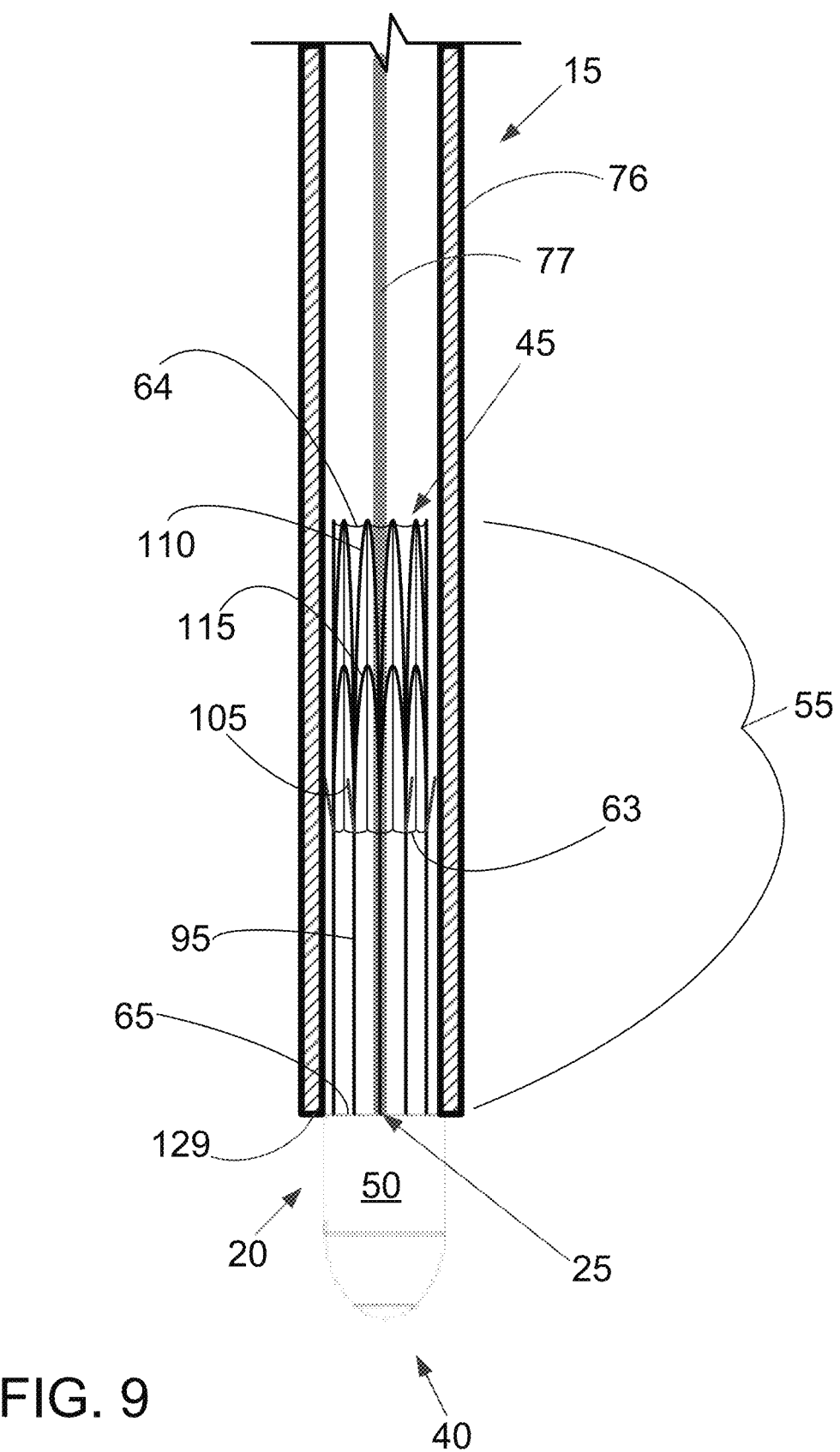
FIG. 9 is a side cross-sectional elevation view of a sheath of the delivery tool with the implantable cardiac valve repair implant maintained in the collapsed state by being confined within the sheath, the implant being coupled to a distal end of a catheter that extends through the sheath.

FIG. 9 is a side cross-sectional elevation view of the sheath 76 of the delivery tool 15 with the implantable cardiac valve repair implant 20 and distal region of the catheter 77 located therein. As can be understood from FIG. 9, during delivery the implant 20 is maintained in the collapsed state by being confined within the sheath 76, and the implant 20 is coupled to a distal end of a catheter 77 that extends through the sheath 76. The control sutures 130, while not shown in FIG. 9 for clarity purposes, would extend through the catheter 77 and/or the sheath 76, as can be understood from FIGS. 1A and 8.

With the implant 20 maintained in the collapsed state by virtue of being confined within the sheath 76 of the delivery tool 15, the implant may be delivered and deployed at the target site via an antegrade percutaneous route (e.g., a trans-femoral or trans-jugular route) with the patient consciously sedated during the procedure. A distal end 25 of the catheter 77 is coupled with the proximal end 65 of the central occluder 50 to maintain the implant 20 within the sheath 76 in the collapsed state until the physician decides to deploy the implant within the target cardiac valve.

Upon the implant being properly positioned in the atrium and beginning to approach the target cardiac valve for repair, the physician actuates the tool 15 to cause the catheter 77 to act as a plunger and/or stopper, thereby driving the collapsed implant 20 distally from the confines of the sheath 76 and/or allowing the sheath 76 to be withdrawn proximally from about the implant 20. Upon the collapsed implant 20 becoming exposed by action of exiting the distal end 129 of the sheath, the implant 20 self-biases into its expanded state, as depicted in FIGS. 2-6. However, as indicated in FIG. 8, despite having exited the sheath distal end 129 and assuming the expanded state, the proximal end 65 of the central occluder 50 of the implant 20 remains coupled to the catheter distal end 25 and the implant frame 55 is coupled to the sutures 130, thereby allowing the physician to use the delivery tool 15 to drive the implant into the target valve and manipulate the implant therein for implantation.

The configuration of the implant 20 facilitates delivery and implantation that is very easy and fast. The implant's ease of delivery is facilitated by it generally only requiring the user to approximately center the frame and push it into the valve.

Upon arrival of the implant 20 within the atrium and at the target cardiac valve, the physician simply uses the tool 15 to actuate the sutures 130 to allow the frame 55 to self-bias open over the atrial side of the target cardiac valve in a controlled manner. The catheter 77 of the tool 15 is then used to push the implant 20 towards the ventricle to engage the frame barbs 105 into the atrial tissue surrounding the target cardiac valve. The control sutures 130 can be used to collapse the frame 55 of the implant 20 to facilitate repositioning of the implant if necessary. Once the implant is fully implanted as desired by the physician, the exposed ends of the control sutures 130 are cut near their points of securement to the implant frame 55, and the catheter distal end 25 is released (e.g., unscrewed or otherwise decoupled) from the proximal end 65 of the central occluder 50. With the tool 15 so decoupled from the implanted implant, the tool can be withdrawn from the patient.

FIG. 10 is a view of the implant 20 implanted in a target cardiac valve, as viewed from an atrial position looking towards the valve and the ventricle chamber below. As depicted in FIG. 10, upon being implanted in the target cardiac valve, the implant anchors itself within the target cardiac valve and is configured to reduce regurgitation in the target cardiac valve. When implanted, the implant 20 is located on the atrial side of the target cardiac valve. The frame engages the atrial tissue via the small barbs 105. The thin sheet 60, which is supported on the frame 55, forms an annular surface 62 supported on the expanded frame 55. This annular surface 62 extends across the atrial tissue circumferentially around the circumference of the target cardiac valve. The central occluder 50 is suspended off the frame 55 and located in the middle of the valve orifice or opening. So positioned, the implant provides the following advantages and reduces regurgitation through multiple mechanisms-of-action.

First, the metal frame 55 supports a central occluder 50 that is positioned to block a central leak in the target cardiac valve, the central occluder thereby reducing central regurgitation through the target cardiac valve. Specifically, the central occluder may block part or all of the central regurgitation in the valve.

Second, the thin sheet 60 covering the frame 55 encourages ingrowth with the atrial and annular tissue surrounding the target cardiac valve. With such tissue ingrowth, the thin sheet and its supporting frame 55 can act as an annuloplasty ring to buttress the native tissue and reduce myocardial stretching that could increase regurgitation.

Third, the thin sheet 60 covering the frame 55 may overlap the edges of the leaflet commissures, reducing the possibility of commissural leak.

Finally, the frame 55 may be over-expanded before engaging the retention barbs 105 in the tissue. When the frame is allowed to relax, the frame 55 may reduce the valve orifice of the target cardiac valve and improve apposition of the valve leaflets, thereby reducing or eliminating regurgitation.

III. Steerable Delivery Tool

FIGS. 11A and 11B are plan and side elevation views, respectively, of an alternative valve repair system 1100 according to the present disclosure. Similar to valve repair systems previously discussed herein, the valve repair system 1100 is generally configured to deliver and deploy an implant 20 at a target site, which is generally in a cardiac valve requiring repair. Embodiments of the valve repair system 1100 may be used with, but are not limited to being used with, any implants discussed herein or that are otherwise consistent with this disclosure.

As shown in FIGS. 11A and 11B, the valve repair system 1100 includes a delivery tool 1115. The tool 1115 includes a proximal end 1130 opposite a tool distal end 1125. The delivery tool 1115 further includes a tubular sheath 1176, and a catheter 1177. A control handle 1135 extends distally from the proximal end 1130 and is used by a physician to manipulate the tool 1115 in positioning the implant 20 at the target site and deploying the implant 20 within the target cardiac valve in need of repair. The sheath 1176 and catheter 1177 extend distally away from the control handle 1135 towards the distal end 1125 of the tool 1115. The catheter 1177 extends longitudinally through the sheath 1176, the distal end 1125 of the catheter 1177 forming the distal end 1125 of the tool 1115. The sheath 1176 is used to minimize tissue trauma while the catheter 1177 and implant 20 are advanced to the implantation site. Thus, the delivery tool 1115 is designed to deliver the implant 20 to the implantation site, position the implant in the target cardiac valve, and control opening of the implant 20, all in an atraumatic manner.

Figure 11C:
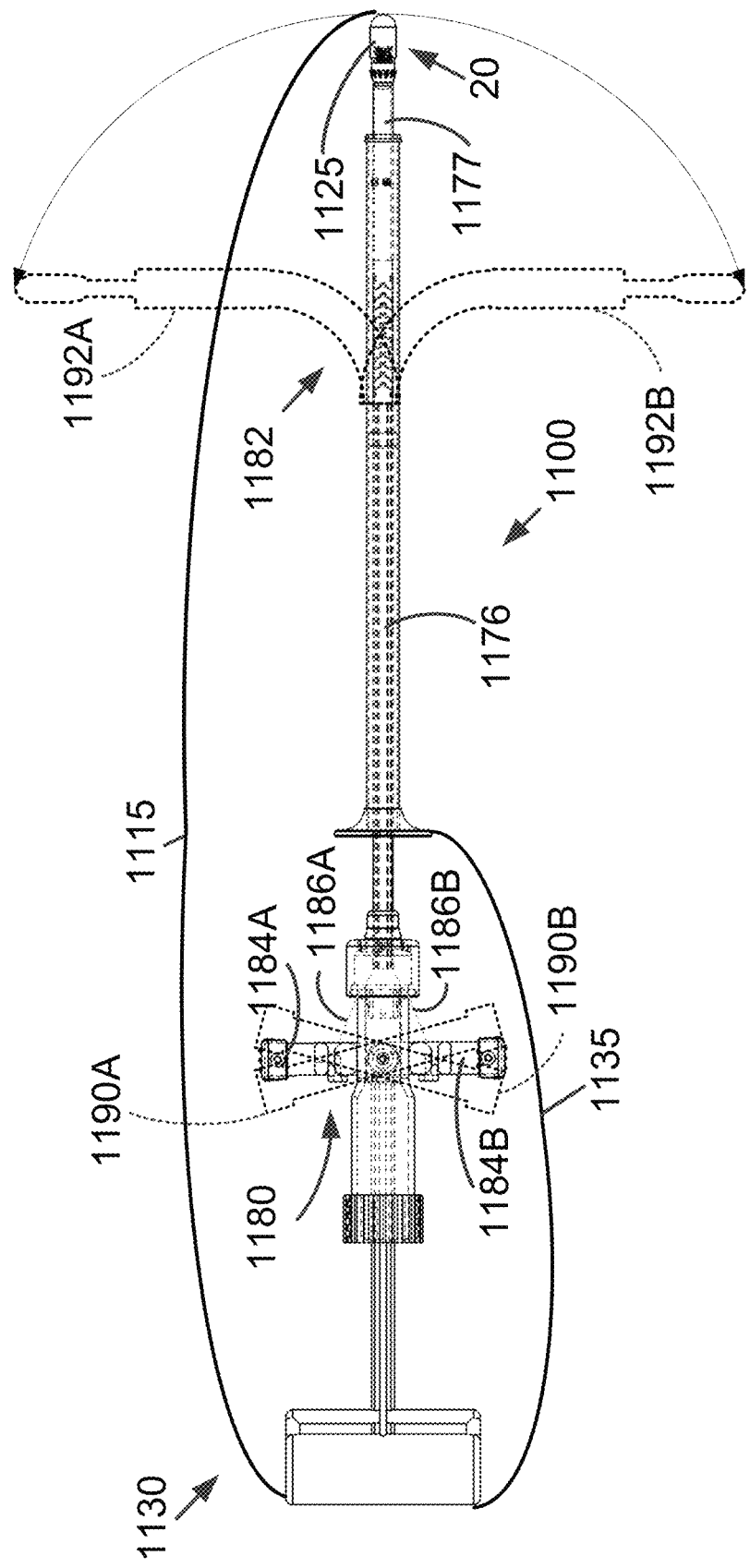

To facilitate delivery of the implant 20 to the implantation site, the catheter 1177 of the tool 1115 may be steerable. In the specific implementation illustrated in FIGS. 11A and 11B, for example, the control handle 1135 of the tool 1115 includes a bidirectional steering control 1180 that may be rotated to steer the distal end 1125 of the tool 1115. As illustrated in FIG. 11C, the steering control 1180 may be rotatable between two extents, illustrated by dashed outlines 1190A, 1190B, to steer the distal end 1125 between corresponding extents, illustrated by dashed outlines 1192A, 1192B. In the specific example illustrated, the steering control 1180 facilitates steering of the distal end 1125 across a range of motion of approximately 180 degrees. Stated differently, the steering control 1180 may rotate the distal end 1125 between a first position in which the distal end 1125 points in a first lateral direction and a second position in which the distal end points in a second lateral direction that is opposite the first lateral direction.

In certain embodiments, steering of the distal end 1125 is achieved by coupling the steering control 1180 to a steering segment 1182 disposed along the catheter 1177, distal the steering control 1180. More specifically, the steering control 1180 may include lateral members 1184A, 1184B, each of which is coupled to a respective side of a distal end of the steering segment 1182 by respective pull wires 1186A, 1186B. Accordingly, when the steering control 1180 is rotated, the corresponding pull wire is pulled and the steering segment 1182 is made to bend in the same direction. For example, referring to FIG. 11C, when the steering control 1180 is rotated counterclockwise with respect to the view of FIG. 11C, as illustrated by dashed outline 1190A, the lateral member 1184A pulls the pull wire 1186A, resulting in the distal end 1125 curling in a counterclockwise direction, as illustrated by dashed outline 1192A. Similarly, when the steering control 1180 is rotated clockwise with respect to the view of FIG. 11C, as illustrated by dashed outline 1190B, the lateral member 1184B pulls the pull wire 1186B, resulting in the distal end 1125 curling in a clockwise direction, as illustrated by dashed outline 1192B.

The steering segment 1182 may take various forms; but, in general, is a flexible and manipulable segment of the catheter 1177 or a separate sleeve or sheath coupled to the catheter 1177. In certain embodiments, for example, the steering segment 1182 may be a sleeve or a portion of the catheter 1177 that is formed from a flexible material. In other embodiments, the steering segment 1182 may be segmented or otherwise include slits, cutouts, or similar voids along its length to provide flexibility. In one specific implementation, the steering segment 1182 may have a helical shape. In still other embodiments, the steering segment 1182 may be have a segment of the catheter 1177 having a reduced wall thickness. The foregoing are merely examples and other techniques for forming the steering segment 1182 that may be used are contemplated.

In certain embodiments, the pull wires 1186A, 1186B are run within an annular space defined between the sheath 1176 and the catheter 1177. Alternatively, the pull wires 1186A, 1186B may be run through a lumen defined within a wall of the catheter 1177, a wall of the sheath 1176, or a third annular body disposed along the distal length of the tool 1115. For example, the catheter 1177 or an additional tubular sheath disposed between the catheter 1177 and the sheath 1176 may be formed as a triple lumen extrusion including a central lumen and a pair of smaller lumens disposed on opposite sides of the central lumen and through which the pull wires 1186A, 1186B extend.

Although illustrated in FIG. 11C as having a 180-degree range of motion, embodiments of the present disclosure may be configured to have other ranges of motions. For example, certain embodiments may be configured to rotate the distal end 1125 through 360 degrees of rotation, e.g., from a first position in which the distal end 1125 points proximally on a first side of the tool 1115 to a second position in which the distal end 1125 also points proximally on a second side of the tool 1115 opposite the first side. In other embodiments, the distal end 1125 may have a reduced range of motion such as but not limited to 135 degrees, 90 degrees, 45 degrees, or 15 degrees. In addition, while the range of motion illustrated in FIG. 11C is illustrated as being substantially even in both directions, embodiments of the present disclosure may have ranges of motion that are uneven in different directions. For example, a tool with a 135-degree range of motion may travel 90 degrees in a first direction but only 45 degrees in a second direction opposite the first direction. Moreover, while the tool 1115 has a neutral position in which the catheter 1177 is substantially straight, the catheter 1177 may alternatively be configured to have a bias in a particular direction.

IV. Implant with Tension Control Line

Figure 12:
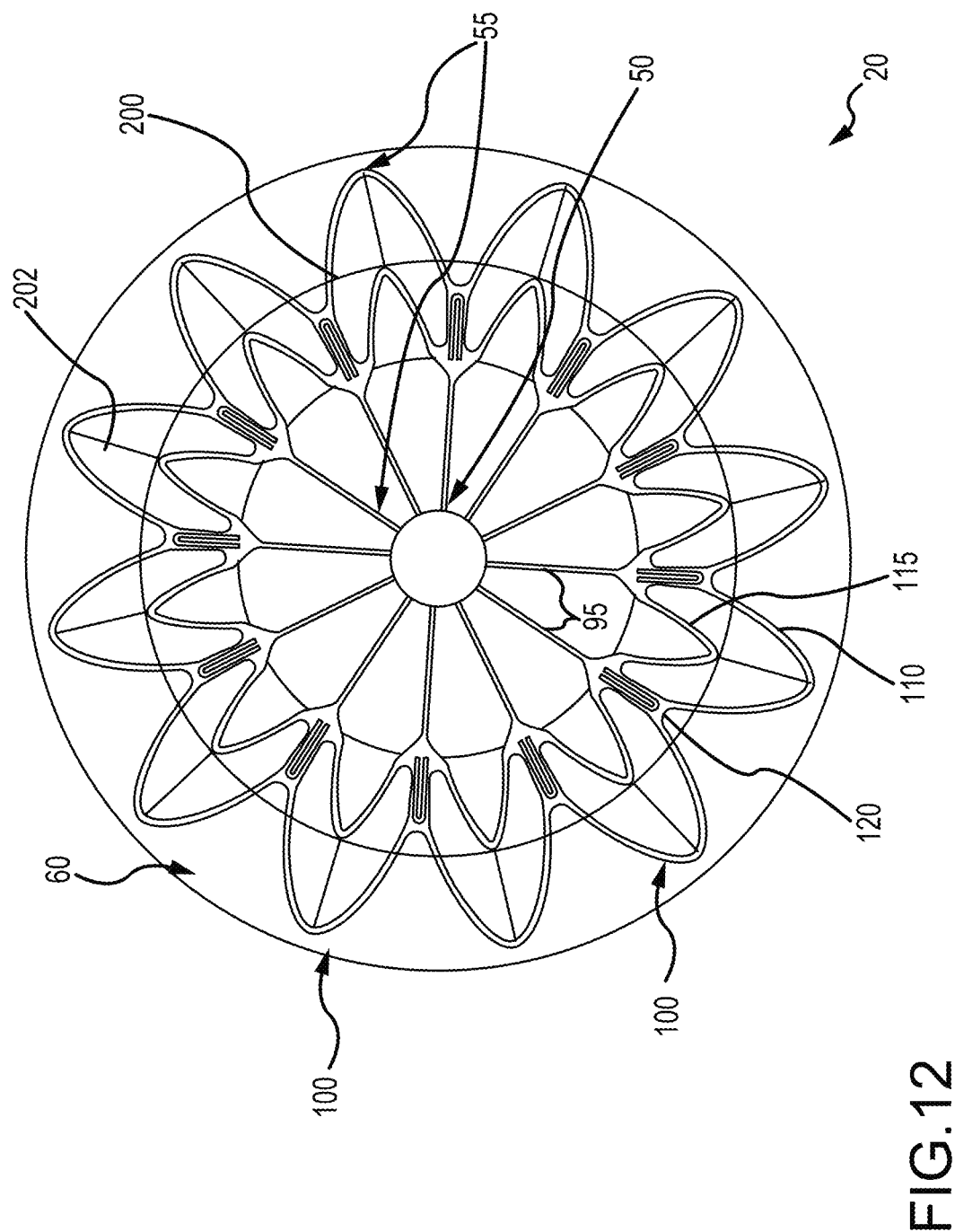
FIG. 12 is a distal plan view of an implantable cardiac valve repair implant in the expanded state and including a tension control line.

FIG. 12 is a distal plan view of the implant 20 in an expanded state and incorporating a tension control line 200. As previously discussed in the context of FIGS. 2-6, the implant 20 generally includes a central occluder 50, a frame 55 and a thin sheet 60 supported on the frame 55. Further details regarding the components and construction of the implant 20 and the frame 55 are provided above in the context of FIGS. 2-6.

As illustrated in FIG. 12, the tension control line 200 may be in the form of a wire, suture, cord, or similar elongate body coupled to the frame 55 and radially inward of the thin sheet 60 relative to the longitudinal axis 70 (shown in FIG. 5) of the implant 20. The tension control line 200 may form a loop extending around the frame 55 and may be formed from a single length of wire, suture, etc. In other implementations, the tension control line 200 may instead be formed from multiple discrete segments of wire, suture, etc., with each discrete segment coupled to the frame 55 and optionally coupled to adjacent segments of the control line 200.

During operation and, more specifically, during deployment of the implant 20, the tension control line 200 is releasably coupled to tension control members (e.g., tension control members 320 illustrated in FIGS. 13-22 and discussed below in further detail) of a delivery tool (e.g., delivery tool 300, similarly illustrated in FIGS. 13-22 and discussed below). The tension control members may be coupled to a handle or similar actuatable component of the delivery tool (such as the handle 35 of the tool 15 previously discussed), to vary tension applied to the tension control line 200 by the tension control members. For example, rotating the handle 35 in a first direction may cause the tension control members to translate proximally/retract, thereby increasing tension on the tension control line 200, while rotating the handle 35 in an opposite direction may cause the tension control members to translate distally/extend, thereby reducing tension on the tension control line 200. Stated differently, manipulating the handle 35 in a first direction generally stops expansion of and/or collapses the frame 55 of the implant 20 (e.g., to allow repositioning of the implant 20) while manipulating the handle 35 in a second direction generally stops collapse of the frame and/or expands the frame 55, whether by action of the handle 35 or as a result of a bias of the frame 55 to into the expanded configuration.

In general, the tension control line 200 is releasably retained by the tension control members at discrete locations along the length of the tension control line 200. The tension control line 200, however, extends across the frame 55 and is coupled to the frame 55 at multiple locations. As a result, even though tension modifications may be applied at the connection point between the tension control members and the tension control line 200, tension is distributed relatively evenly across the tension control line 200 and the frame 55, thereby providing even expansion and collapse of the frame 55 and improved control during deployment and placement of the implant 20.

In the implementation of FIG. 12, the tension control line 200 is coupled to (e.g., tied or adhered to) the inner arcuate members 115 of the frame 55. More generally, the tension control line 200 may be coupled to any suitable portion of the frame 55 such that the tension control line 200 substantially extends about the frame 55. For example, and without limitation, in other implementations of the present disclosure, the tension control line 200 may instead be fixed to spokes 95, outer arcuate members 110, or any other suitable portion of the petal portions 100 of the frame 55.

In certain implementations, the tension control line 200 may be additionally coupled to other locations of the frame 55 by additional control segments or linking structures. For example, FIG. 12 illustrates the tension control line 200 coupled to the inner arcuate members 115 of the frame 55. The tension control line 200 is further coupled to each of the outer arcuate members 110 by corresponding links, such as the link 202. Similar to the control line 200, the link 202 may be formed of wire, suture, or similar material and, in certain cases, may be formed of the same material as the control line 200. In operation, the link 202 helps to further distribute tension to the outer arcuate members 110 and, as a result, further improves control of expansion and collapse of the frame during deployment of the implant 20.

Although illustrated in FIG. 12 as coupling the tension control line 200 to the outer arcuate members 110, in other implementations, links may be used to couple the tension control line 200 to other elements of the frame 55 depending on how the tension control line 200 is configured. For example, in implementations in which the tension control line 200 is coupled to the outer arcuate members 110, links may be used to couple the tension control line 200 to the inner arcuate members 115.

V. Deployment of Implants with Tension Control Lines

As previously discussed, implants according to the present disclosure may include tension control lines for enhanced control during deployment and implantation. Such delivery and implantation may be further facilitated by corresponding delivery tools configured to modify and control tension applied to the tension control lines and to selectively release the implant when properly positioned.

Figure 13:
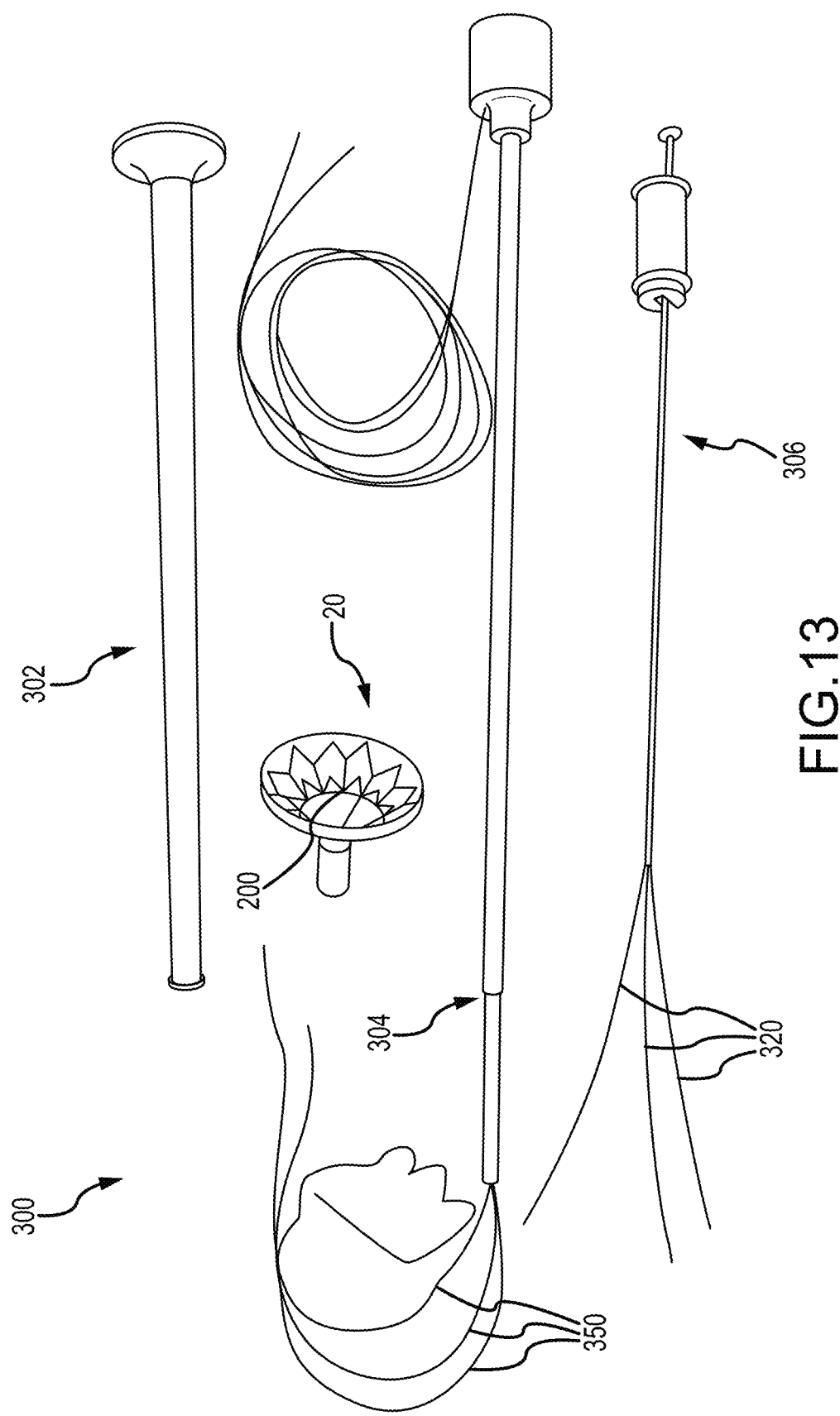
FIG. 13 is an illustration—of an example implantable cardiac valve repair system in a disassembled configuration and including each of an implant and a delivery tool.

FIG. 13 is an illustration including a delivery tool 300 in accordance with the present disclosure in a disassembled state. As illustrated, the delivery tool 300 generally includes a sheath 302, a release catheter 304, and a tension control assembly 306. An implant 20 including a tension control line 200 is also pictured. The sheath 302 generally forms an exterior of the delivery tool 300 and houses the other components during insertion into the patient. More specifically, the release catheter 304 is generally disposed within the sheath 302 and the tension control assembly 306 is, in turn, disposed within the release catheter 304.

As described below in further detail, the tension control line 200 of the implant 20 is releasably coupled to the tension control assembly 306 by the release catheter 304 and is maintained in a collapsed state within the sheath 302 during initial insertion into the patient. During deployment, the release catheter 304 is distally extended from the sheath 302, thereby allowing the implant 20 to expand. Subsequent control of expansion and collapse of the implant 20 is facilitate by tension control members 320 extending from the tension control assembly 306, which are coupled to the control tension control line 200 of the implant 20 by release lines 350 of the release catheter 304. Following location of the implant 20 within the patient, the release lines 350 are retracted to decouple the tension control members 320 from the tension control line 200, thereby releasing the implant 20.

FIG. 14 is a cross-sectional view of a distal portion 301 of the delivery tool 300 in an assembled state and with each of the release catheter 304 and the tension control assembly 306 in an extended configuration for purposes of illustrating various elements of the delivery tool 300. FIG. 15 is also a cross-sectional view of the distal portion 301 of the delivery tool 300 but further includes an implant 20 and illustrates the delivery tool 300 in a retracted state, such as would be the case during initial insertion of the delivery tool 300 into the patient. For purpose of illustrating coupling of the implant to the release catheter 304, the frame 55 and associated components of the implant 20 are only partially illustrated in FIG. 15.

Figure 19:
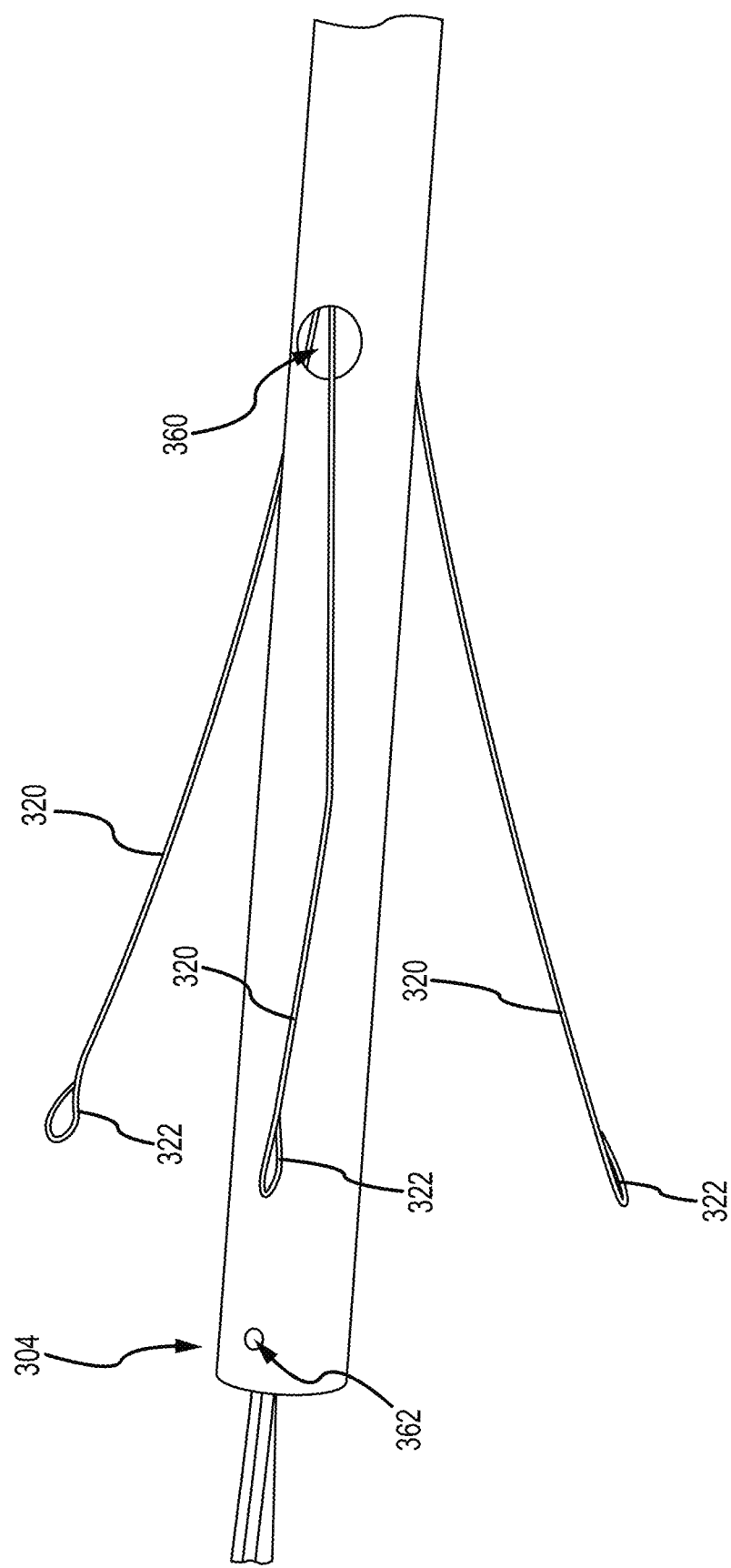
FIG. 19 is an illustration of a plan view of the delivery tool illustrating protrusion of tension control members through a release catheter of the delivery tool.

As previously discussed, tension control assembly 306 generally includes tension control members 320 that are releasably coupled to the control line 200 of the implant 20. As illustrated in FIGS. 14 and 15, the tension control members 320 may be in the form of cables, control sutures, wires, or similar elongate structures that extend distally from a distal end of a tension control shaft 324. In at least certain implementations, the tension control members 320 may terminate in a loop (e.g., loop 322) or similar structure to facilitate coupling to the tension control members 320 to the tension control line 200 of the implant 20. FIG. 19 is an illustration of the tension control assembly 306 disposed within the release catheter 304 with the tension control members 320 extending distally out of a catheter body 352 of the release catheter 304.

The release catheter 304 includes release lines 350 disposed within and extending through the catheter body 352. The catheter body 352 further defines two sets of lateral holes for facilitating tensioning and release functionality of the delivery tool 300. More specifically, the catheter body 352 defines a set of proximal holes 360 and a set of distal holes 362. The catheter body 352 further defines a distal opening 357. As illustrated in FIGS. 14 and 19, the tension control assembly 306 is generally assembled with the release catheter 304 such that the tension control members 320 extend distally through the proximal holes 360.

Figure 16:
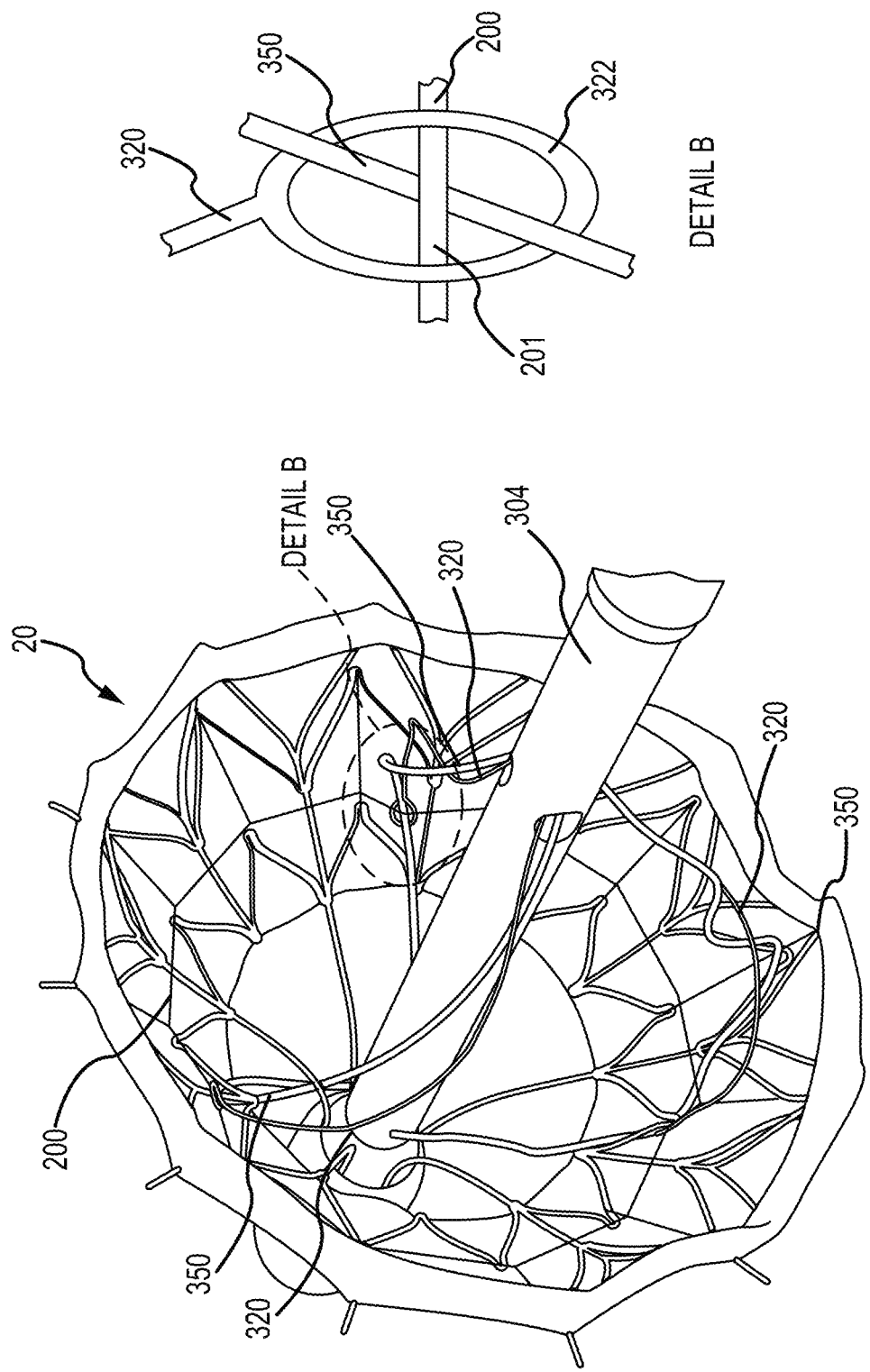
FIG. 16 is an illustration of a distal perspective view of the implant coupled to the delivery tool and in an expanded state.
Figure 17:
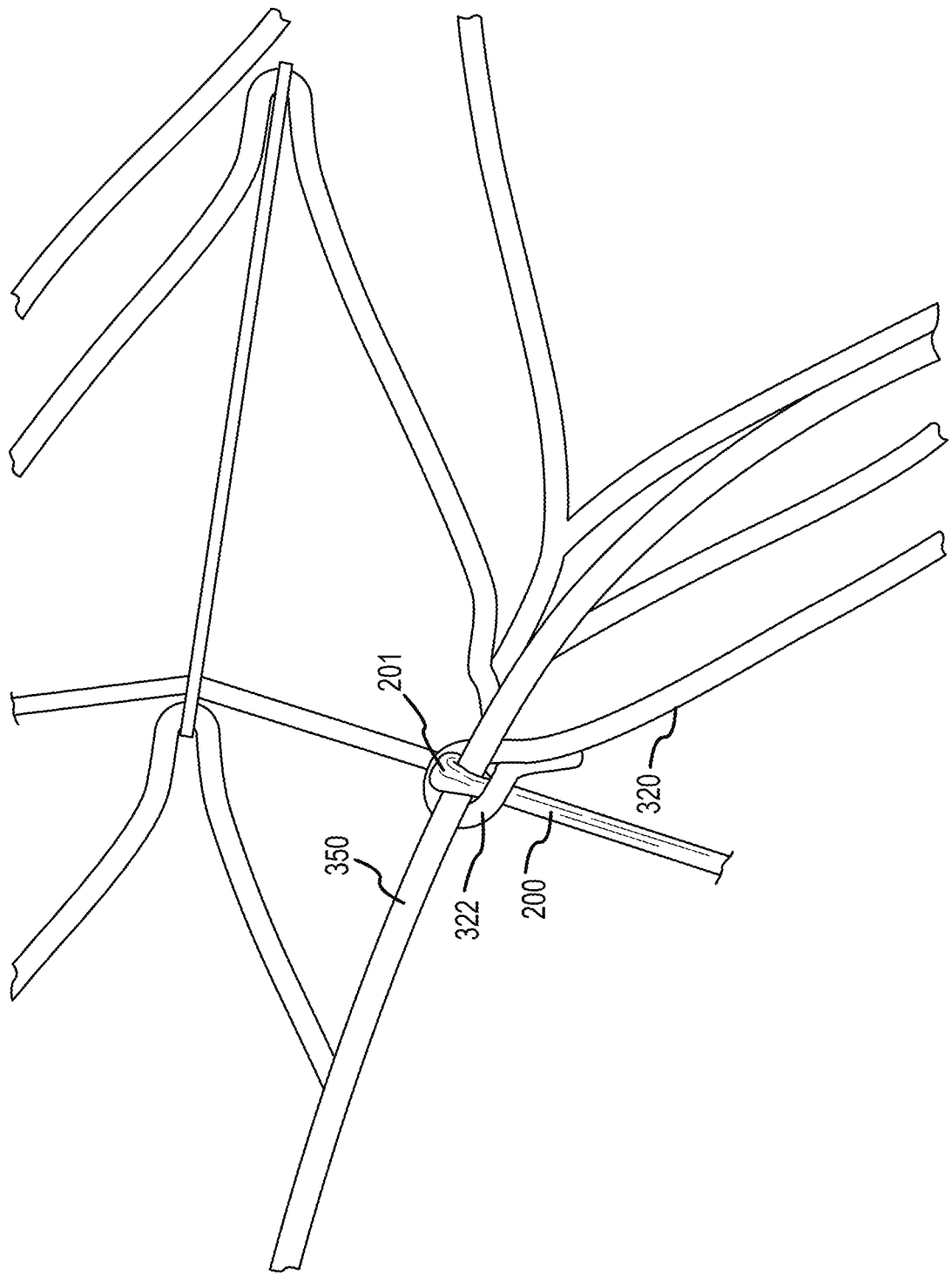
FIG. 17 is an illustration of a detailed view of a connection between the delivery tool and the tension control line of the implant and, more specifically connection between a tension control member of the delivery tool and the control line of the implant using a release line of the delivery tool.
Figure 18:
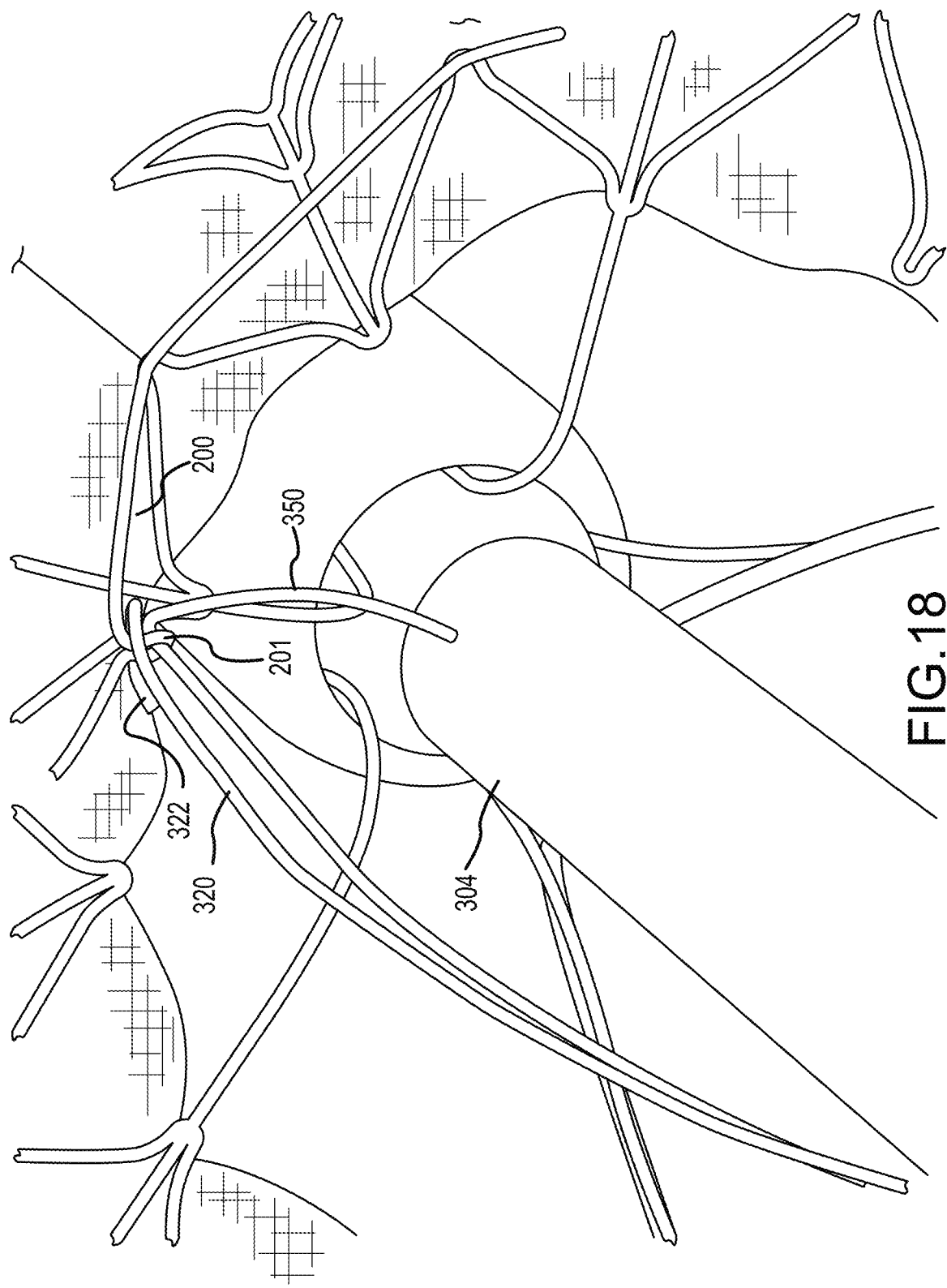
FIG. 18 is an illustration of a second detailed view of a connection between the delivery tool and the tension control line of the implant.

The implant 20 is generally coupled to the delivery tool 300 by coupling the implant 20 to the tension control members 320 using the release lines 350. FIG. 16 is an illustration of a proximal perspective view of the implant 20 coupled to the delivery tool 300 in an expanded state to illustrate such coupling. As illustrated in Detail B of FIG. 16, a loop 201 of the tension control line 200 is pulled through the loop 322 of the tension control member 320. The release line 350 is then passed through the loop 201 of the tension control line 200 and across the loop 322 of the tension control member 320, thereby retaining the loop 201 of the tension control line 200 through the loop 322 of the tension control member 320. To release the coupling between the control line 200 and the tension control member 320, the release line 350 is slid out of the loop 201, thereby enabling the loop 201 to pass through the loop 322 of the tension control member 320 and decoupling the tension control member 320 from the control line 200. Detailed illustrations of the loop 201 of the tension control line 200 coupled to the loop 322 of the tension control member 320 are provided in FIGS. 17 and 18.

Referring back to FIG. 15, routing of the release lines 350 generally includes routing the release lines 350 (shown in dashed lines for clarity and distinction over other illustrated elements) through the catheter body 352 to an exterior thereof, such as by passing the release lines 350 through the distal holes 362 of the catheter body 352. The release lines 350 may then be routed proximally to join the control line 200 to the tension control members 320, as noted above and as illustrated in FIGS. 16-18. The release lines 350 may then be routed proximally and back into the catheter body 352 through the proximal holes 360 where the release lines 350 may be retained, e.g., by friction, until the implant 20 is to be released.

As shown in FIG. 15, in at least certain implementations, the occluder 50 of the implant 20 may include a proximally extending annular protrusion 51 defining each of a proximally open annulus 53 and laterally extending holes 57 in communication with the annulus 53. In such implementations, the annular protrusion 51 may be disposed within the distal opening 357 (shown in FIG. 14) of the release catheter 304 during insertion and delivery to an implantation location and the release lines 350 may be further routed into the annulus 53 and through the holes 57 before being passed through the distal holes 362 of the catheter body 352.

Figure 20:
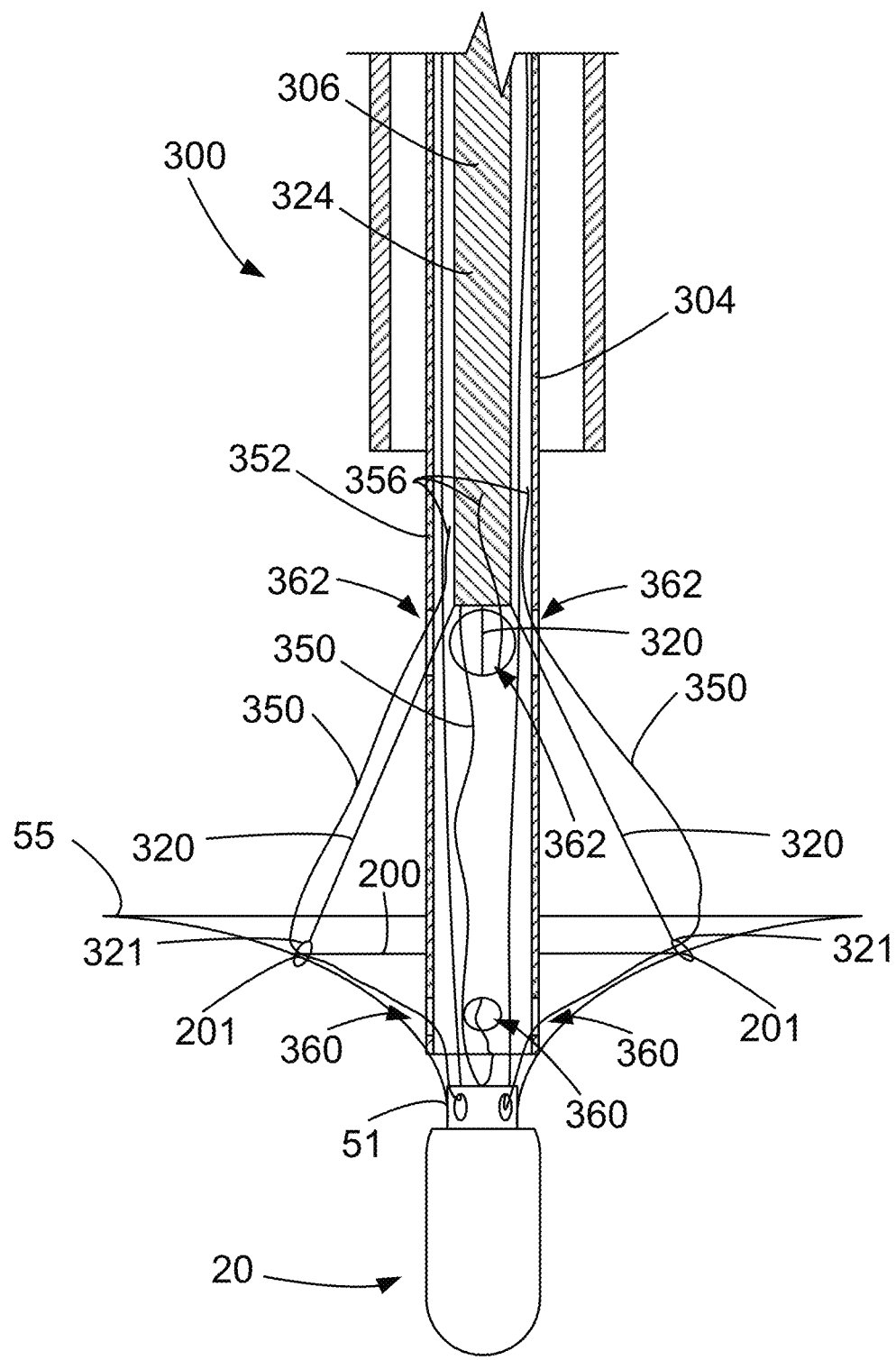
FIG. 20 is a side cross-sectional view of the delivery tool coupled to the implant with the implant in an expanded configuration.
Figure 21:
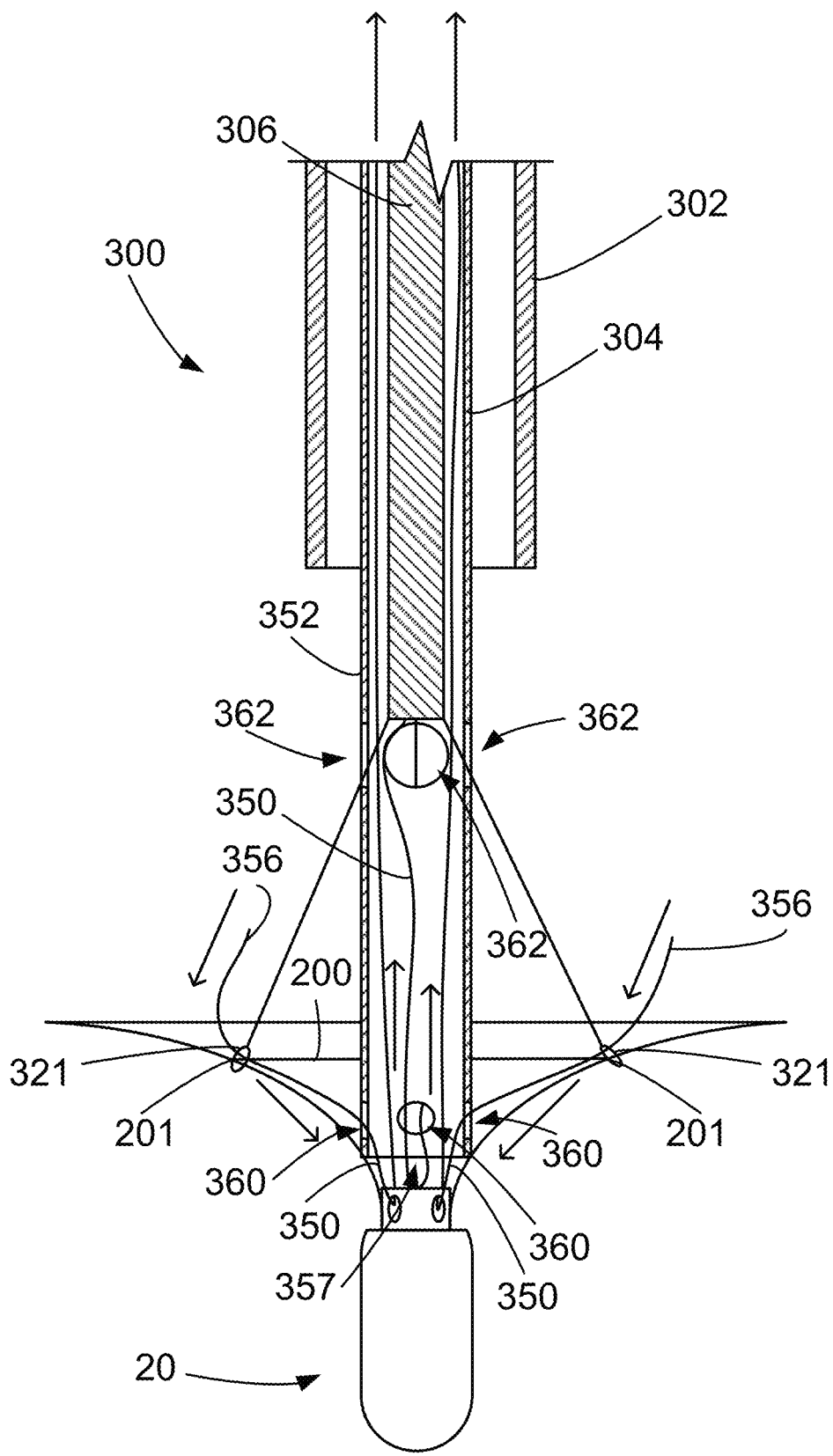
FIG. 21 is a side cross-sectional view of the delivery tool and the implant during release of the implant from the delivery tool.
Figure 22:
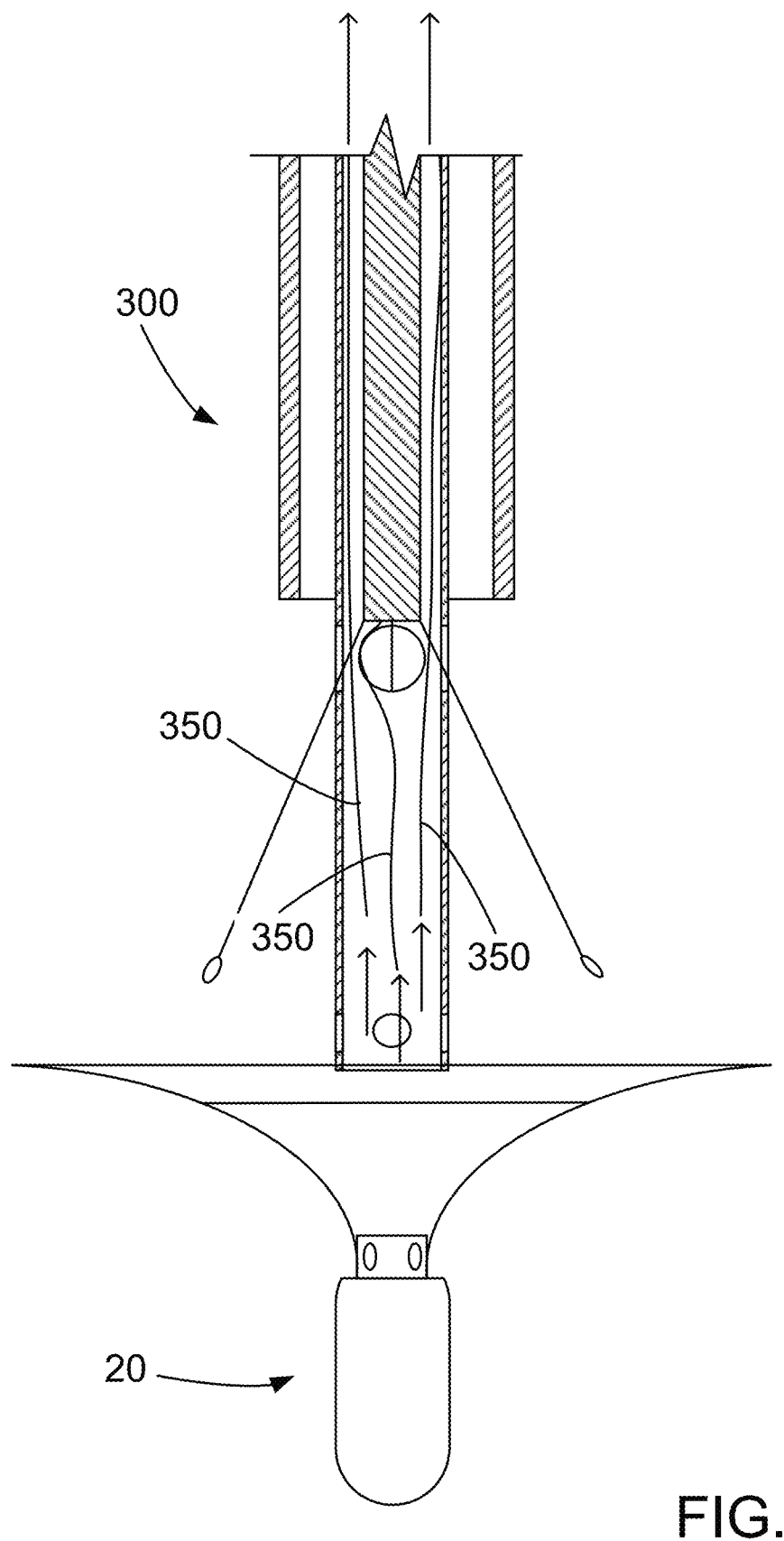
FIG. 22 is a side cross-sectional view of the delivery tool and the implant following release of the implant from the delivery tool.

FIGS. 20-22 illustrate the general process of releasing the implant 20 from the delivery tool 300. Referring first to FIG. 20, the delivery tool 300 and implant 20 are shown with the frame 55 of the implant 20 in an expanded configuration but still coupled to the delivery tool 300. More specifically, the implant 20 is coupled to the delivery tool 300 by virtue of the release lines 350 of the release catheter 304, each of which is routed, in order, through the catheter body 352, through the annular protrusion 51 of the implant 20, through one of the distal holes 362 of the catheter body 352, through one of the loops 201 of the tension control line 200 extending through a loop 321 of one of the tension control members 320, and back into the catheter body 352 through one of the proximal holes 360. As previously noted, in at least certain implementations, the ends 356 of the release lines 350 may be retained within the catheter body 352 by friction.

In the state illustrated in FIG. 20, the tension control shaft 324 of the tension control assembly 306 may be actuated (e.g., by translating and/or rotating the shaft or a handle assembly coupled to the shaft) to vary the tension applied to the frame 55 of the implant 20. By doing so, the frame 55 may be expanded and/or collapsed to facilitate placement of the implant 20 prior to release of the implant 20 from the delivery tool 300.

Referring next to FIG. 21, the delivery tool 300 and implant 20 are illustrated part way through release of the implant 20 from the delivery tool 300. In general, release of the implant 20 from the delivery tool 300 is performed by pulling the release lines 350 proximally through the catheter body 352. As illustrated and for each release line 350 and as indicated by the open arrows, such pulling causes the end 356 of the release line 350 to exit the catheter body 352 through one of the proximal holes 360, pass through one of the loops 201 of the tension control line 200 to release the loop 201 from a corresponding control member 320, pass through one of the distal holes 362 of the catheter body 352 and the annular protrusion 51 of the implant 20, and reenter the catheter body 352 through the distal opening 357 of the catheter body 352. As a result, pulling the release lines 350 decouples the implant from the delivery tool and allows removal of the delivery tool 300 with the implant 20 remaining in place, as shown in FIG. 22. Following release of the implant 20, each of the release catheter 304 and the tension control assembly 306 may be proximally retracted and/or proximally removed from the sheath 302.

Notably, the process of releasing the implant 20 from the delivery tool 300 by pulling the release lines 350 applies a net force on the implant 20 that expands the frame 55 and/or resists collapse of the frame 55. More specifically, as the release lines 350 are pulled to release the implant 20, the release lines 350 apply a net distal force on the implant 20, thereby pressing the implant 20 into its current implantation location. Moreover, because such distal force is applied at the connection between the control line 200 and the tension control member 320 it acts to further expand or otherwise provide additional counterforce against collapse of the frame 55. In contrast, if a net proximal force were to be applied, the implant 20 may be pulled out of place and/or the frame 55 may undergo a partial collapse, each potentially leading to the implant 20 becoming dislodged or losing its orientation. Accordingly, by routing the release lines 350 as noted above, proper placement of the implant 20 is more easily controlled and more likely to be maintained following release of the implant 20.

VI. Multi-Part Occluder

Figure 23:
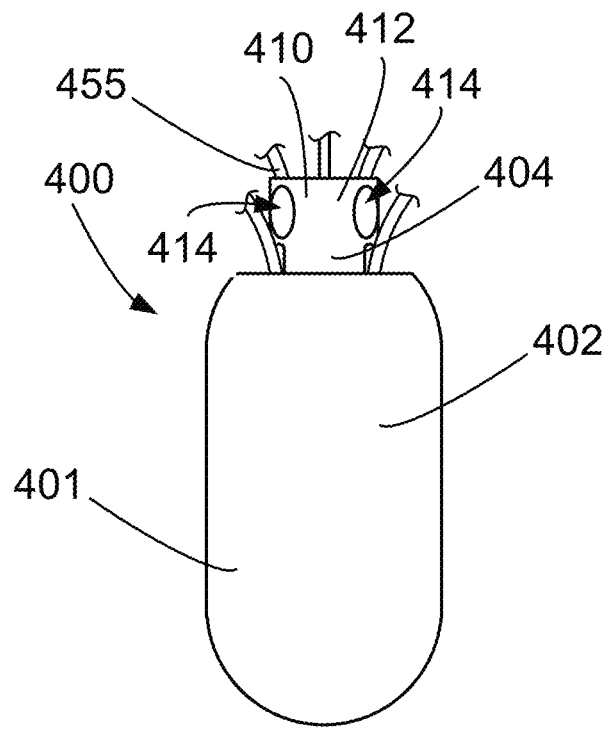
FIG. 23 is a side elevation view of a distal portion of an implant.
Figure 24:
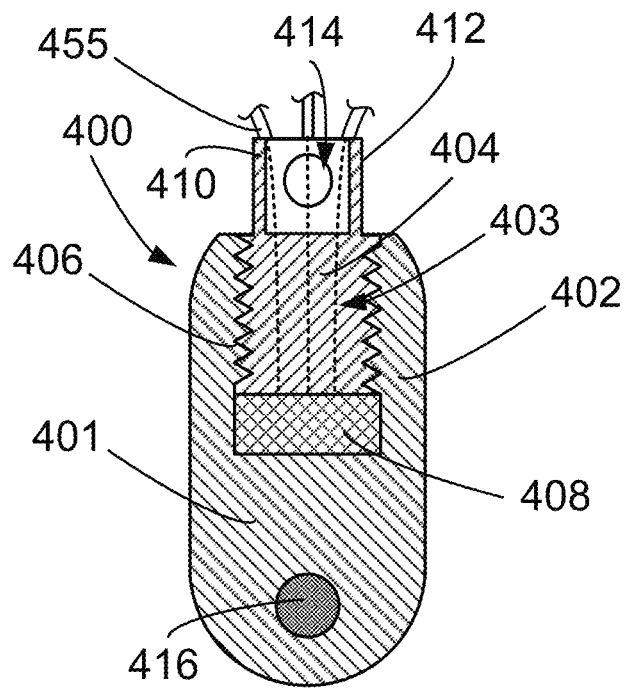
FIG. 24 is a side cross-sectional view of the distal portion of the implant of FIG. 23.

FIGS. 23 and 24 illustrate a distal portion of an example implant 400 that may be used in implementations of the present disclosure. More specifically, FIG. 23 is a side elevation view of the distal portion of the implant 400 while FIG. 24 is a cross-sectional view of the implant 400, each of which emphasize an occluder 401 of the implant 400.

As illustrated, the occluder 401 includes an occluder body 402 defining a cavity 403 within which an insert 404 is disposed. The insert 404 is coupled to the occluder body 402. In the specific implementation illustrated in FIGS. 23 and 24, the insert 404 is coupled to the occluder body 402 by a threaded connection 406; however, any suitable connection (e.g., adhesive, welding, etc.) may be used instead of a threaded connection.

The occluder 401 further includes a frame base 408 disposed within the cavity 403 of the occluder body 402 and distal the insert 404. The frame base 408 is coupled to a frame 455 of the implant 400 (shown in part and which may be substantially similar to other frames disclosed herein) which extends from the frame base 408 and exits proximally from the occluder body 402. The frame base 408 may be coupled to the occluder body 402 and/or may be maintained in place by the insert 404.

The insert 404 further includes a proximally extending annular protrusion 410. The annular protrusion 410 includes a sidewall 412 through which one or more laterally extending holes 414 may be defined. As previously discussed in the context of FIGS. 15 and 20-22, during use of systems disclosed herein, release lines of a delivery tool may be routed through the holes 414 to secure the implant 400 to a delivery tool and, more specifically, to a release catheter of a delivery tool.

The occluder 401 further includes a marker 416 disposed within the occluder body 402. In certain implementations, the marker 416 may be a radiopaque marker to facilitate fluoroscopic observation of the implant 400 during delivery and implantation. As shown, the marker 416 may be embedded within the occluder body 402, such as by molding the occluder body 402 about the marker 416. In other implementations, the cavity 403 may be shaped to receive the marker 416 in addition to the insert 404 and the frame base 408. In still other implementations, the marker 416 may be disposed on an exterior surface of the occluder body 402. Although illustrated as a spherical bead in FIG. 24, the marker 416 may be have any suitable shape. Similarly, any suitable number of markers may be incorporated into the occluder body 402. In other implementations, the occluder body 402 may be formed from a material with radiopaque additives. In still other implementations, either or both of the frame base 408 and the insert 404 may be formed of radiopaque material or include one or more radiopaque markers.

VII. Skirted and Sheet-Based Occlusive Assemblies

As noted above, implementations of implants according to the present disclosure may include an occlusive body supported by a frame with a thin sheet supported by and extending around a proximal portion of the frame. When the implant is deployed within the heart to support function of a heart valve, the frame is supported by an annulus of the valve or by the walls of the atrium such that the occlusive body is disposed to interact with and seal against leaflets of the valve. In certain implementations, the thin sheet may be formed from a material that allows for tissue ingrowth such that, over time, the implant is retained more robustly within the heart. In addition to this structural function, the thin sheet may be configured to at least partially overlap one or more commissures of the valve leaflets to correct or reduce commissural regurgitation.

In addition to the outer thin sheet discussed above, implementations of this disclosure may alternatively or additionally include an inner sheet. For example, implants of the present disclosure may include an occlusive assembly that includes an occlusive body (such as the bullnose-style occluder or other occluders discussed above) and a sheet of material (generally referred to as a "skirt" or "inner sheet" herein) that extends from and circumferentially around the occlusive body. In such implementations, the inner sheet may be coupled to the occlusive body and/or portions of the implant frame extending from the occlusive body. In other implementations, the occlusive assembly may omit an occlusive body such that the inner sheet forms a cap-like structure on a distal end of the implant supported by and coupled to a distal portion of the frame. In such implants, the inner sheet may provide a sealing surface for the valve leaflets similar to that provided by the occlusive body. Like the outer sheet, the inner sheet may be formed of a material that promotes or allows tissue ingrowth to create a smooth layer of biological cells. The layer of biological cells may provide a barrier between the inner sheet and native valve leaflets to prevents wearing effects between the inner sheet and native valve leaflets. Alternatively, the inner sheet may be formed from a low friction material (such as PTFE or ePTFE) that resists cell in-growth to provide a smooth surface that prevents wearing effects between the inner sheet and native valve leaflets.

In certain implementations, either of the outer and inner sheets may have a multi-layered construction in which an internal pocket is defined between layers of sheet material. The pocket may contain an additional layer of fabric to serve as padding (e.g., a layer of PET, ePTFE, or other fabric). The pocket may also or alternatively contain a water-absorbing material, such as a hydrogel (e.g., sodium polyacrylate or polyvinyl alcohol) that expands following implantation. In any of the foregoing cases, the filling may form a pad. In implementations in which the inner sheet is formed to include an absorbing/expanding pocket, such pockets may generally pad or otherwise increase the distance between the occluding surface/sheet and the underlying frame of the implant, thereby preventing and padding contact between valve leaflets and the frame.

The foregoing aspects of this disclosure and related concepts are now discussed in further detail with reference to the figures.

Figure 25:
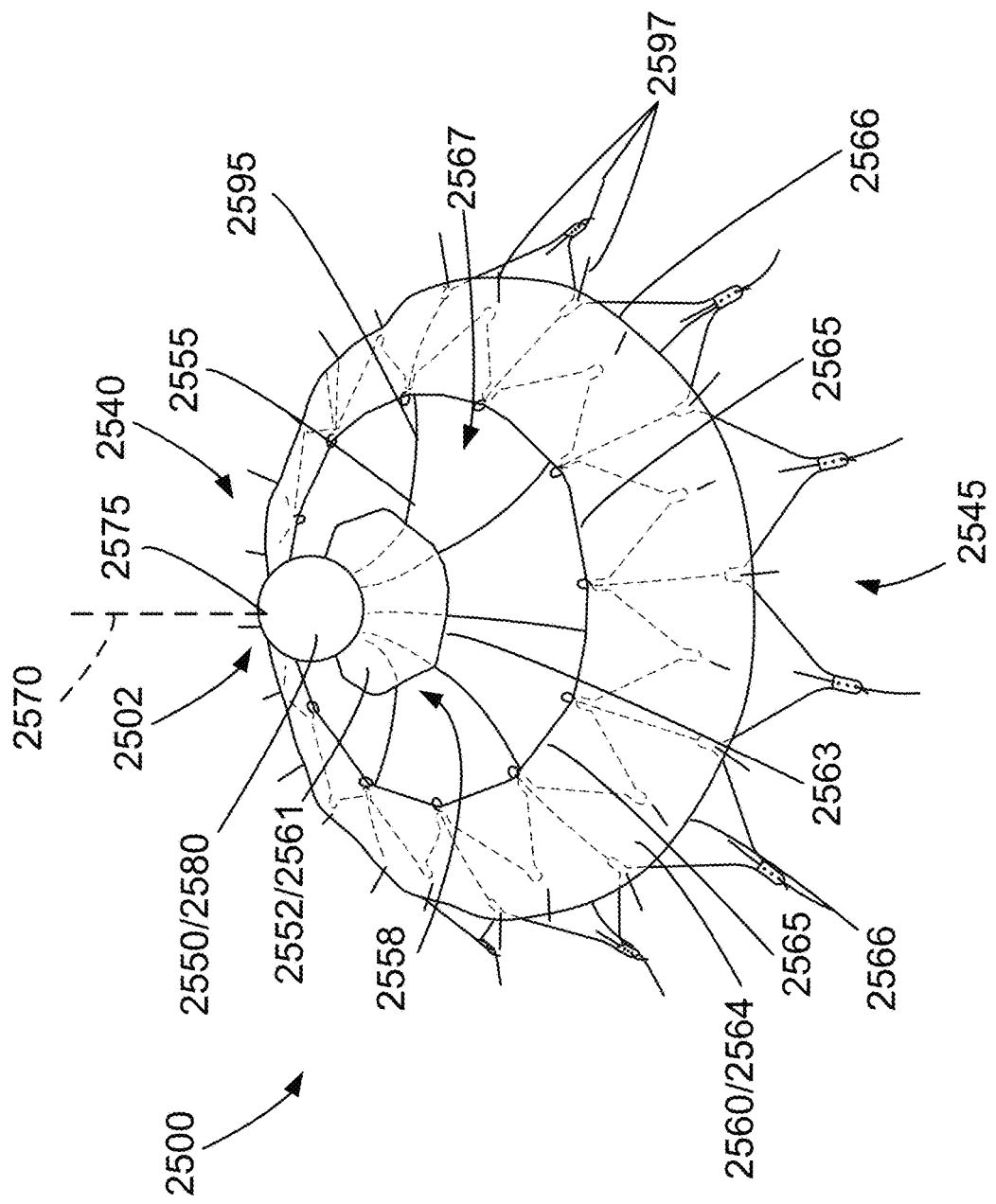
FIG. 25 is a perspective distal-end view of an implant including an occlusive assembly having an inner sheet.
Figure 26:
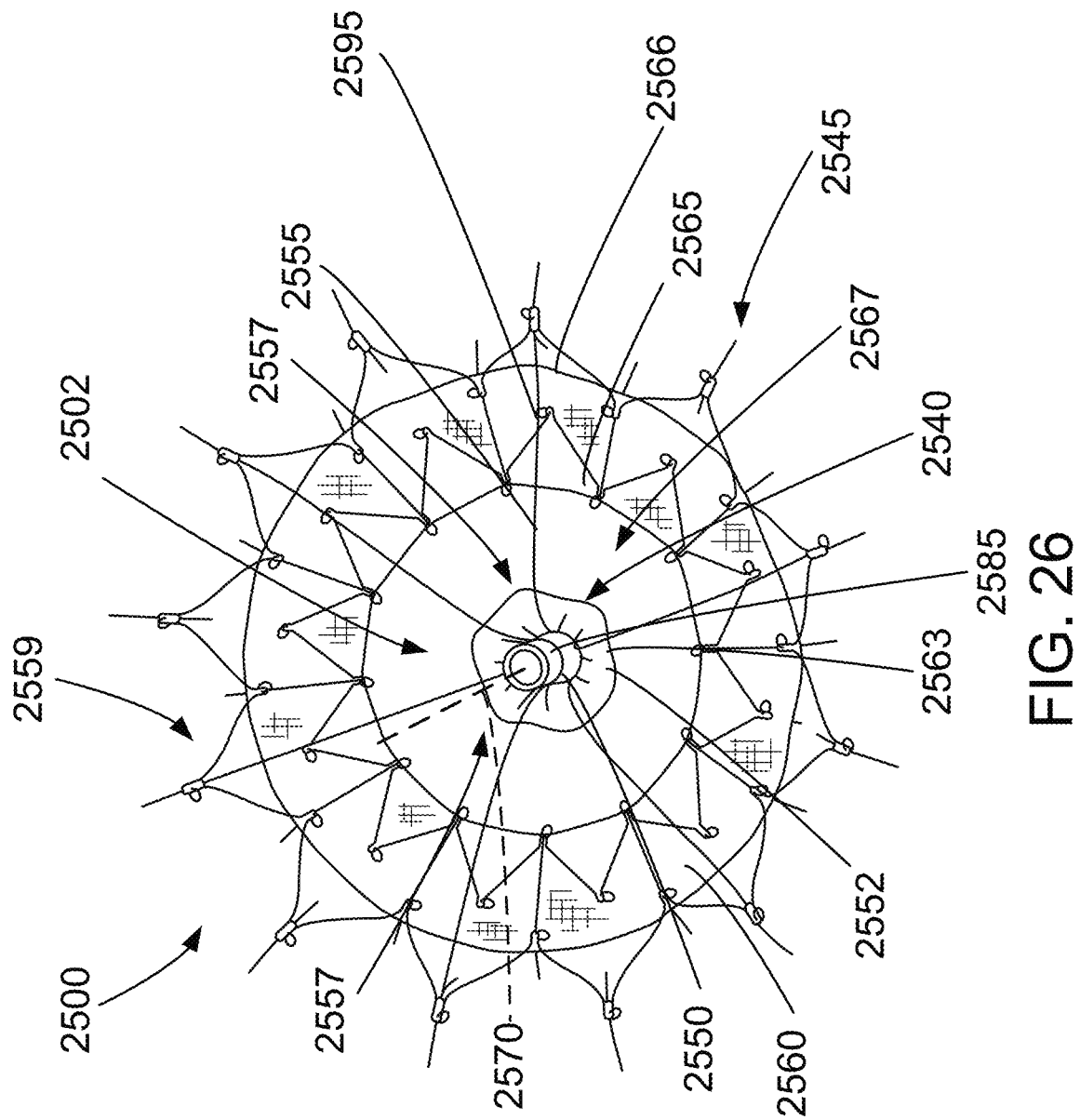
FIG. 26 is perspective proximal-end view of the implant of FIG. 25.

FIGS. 25 and 26 illustrate an example of an implant 2500 including a skirted occlusive assembly. Specifically, FIG. 25 is a perspective distal-side view of implant 2500 while FIG. 26 is a perspective proximal-side view of implant 2500. FIGS. 25 and 26 illustrate implant 2500 when implant 2500 is in an expanded state, such as exists when implant 2500 is implanted in a cardiac valve to be repaired. As illustrated in FIG. 25, implant 2500 includes a distal end 2540 and a proximal end 2545. Distal end 2540 serves as the leading end of implant 2500 during implantation.

Implant 2500 includes an occlusive assembly 2502 that includes a central occlusive body 2550 and an inner sheet 2552 extending about central occlusive body 2550. Implant 2500 further includes a frame 2555 and an outer sheet 2560 supported on frame 2555. In the implementation of FIGS. 25 and 26, frame 2555 extends proximally from central occlusive body 2550. When in the expanded state, the frame 2555 radiates laterally outwardly relative to a central longitudinal axis 2570 of implant 2500. In the expanded state, inner sheet 2552 forms a first annular surface 2561 and outer sheet 2560 forms a second annular surface 2564, each of which is supported on frame 2555.

First annular surface 2561 has a proximal radially outward edge 2563. Similarly, second annular surface 2564 has a distal radially inward edge 2565 and a proximal radially outward edge 2566. Proximal radially outward edge 2563 of first annular surface 2561 and distal radially inward edge 2565 of second annular surface 2564 define a central opening 2567 between inner sheet 2552 and outer sheet 2560. Proximal radially outward edge 2566 of outer sheet 2560 may form the extreme proximal radially outward boundary of the implant when in the expanded state; however, as shown in FIGS. 25 and 26, at least a portion of frame 2555 may extend beyond proximal radially outward edge 2566 of outer sheet 2560. Central longitudinal axis 2570 passes through the extreme distal tip 2575 of central occlusive body 2550. Considering the foregoing and in at least certain embodiments, frame 2555 is generally designed to sit on the floor of the atrium, to induce annular reduction, and to produce a neo-annulus.

In addition to being annular, either of first annular surface 2561 and second annular surface 2564 may also be conical, or relatively so (e.g., parabolic).

When implant 2500 is in the collapsed state, e.g., during delivery of implant 2500 to the target site via a corresponding tool (e.g., the tool 15 of FIG. 1A), frame 2555, inner sheet 2552, and outer sheet 2560 collapse symmetrically about the central longitudinal axis 2570. Thus, like implant 20 of FIGS. 2-6, implant 2500 can transition from the collapsed state to the expanded state like an umbrella. For example and as previously discussed herein in the context of implant 20, implant 2500 may be maintained in a collapsed state (similar to that illustrated in FIG. 7 for implant 20) by the tool 15 so as to allow implant 2500 to be negotiated through the patient vascular system and into an atrial chamber of the heart for implantation of the implant within a target cardiac valve. For example, with implant 2500 maintained in the collapsed state by virtue of being confined within a tubular sheath 76 of the delivery tool 15, implant 2500 may be delivered and deployed at the target site via an antegrade percutaneous route (e.g., an antegrade trans-femoral or trans-jugular route) with the patient consciously sedated during the procedure. Upon being properly positioned in the target cardiac valve for repair, the physician may actuate tool 15 such that tool 15 no longer maintains implant 2500 in the collapsed. Since frame 2555 of implant 2500 is biased to self-expand, implant 2500 self-expands into the expanded state to anchor itself within the target cardiac valve and reduce regurgitation.

Central occlusive body 2550 may take on various forms and shapes. For example, as previously discussed in the context of implant 20, central occlusive body 2550 may have a bullet or conical shape. Additional details regarding such shapes are provided above. Another alternative shape for central occlusive body 2550 is a bulb and is illustrated in FIGS. 25 and 26. In such implementations, central occlusive body 2550 may include a distal bulb 2580 (shown in FIG. 25) with a cylindrical side 2585 (shown in FIG. 26) extending proximally therefrom. In certain implementations, distal bulb 2580 may have a spherical shape; but may alternatively have an ovoid or oblong shape. More generally, distal bulb 2580 may have a shape selected to be atraumatic during delivery and implantation purposes and that facilitates sealing of distal bulb 2580 against the cardiac valve leaflets to reduce or even eliminate central regurgitation past the cardiac valve leaflets.

In general, characteristics of central occlusive body 2550 may be similar to those of central occluder 50 of implant 20. For example, central occlusive body 2550 may be formed various materials, including angio- and/or echolucent materials, may be filled or fillable (e.g., with saline) and may have properties and dimensional characteristics like those of central occluder 50 discussed above.

Like thin sheet 60 of implant 20 being supported by frame 55, each of inner sheet 2552 and outer sheet 2560 is supported on frame 2555 and secured thereto. For example, and without limitation, inner sheet 2552 and/or outer sheet 2560 may be secured to frame 2555 by suturing the respective sheet against an inner surface and/or an outer surface of frame 2555. In other implementations, inner sheet 2552 or outer sheet 2560 may include a cuff or similar folded structure that is folded over an end of frame 2555. For example, as illustrated in FIG. 26, inner sheet 2552 is folded over and sutured against a distal frame portion 2558. More specifically, distal frame portion 2558 includes a circumferential arrangement of arcuate petal portions (e.g., arcuate petal portion 2557) extending distally from central occlusive body 2550. Inner sheet 2552 is then wrapped around a distal surface of distal frame portion 2558, folded over each arcuate petal portion 2557 and sutured in place such that inner sheet 2552 is secured to distal frame portion 2558.

Alternatively, each of inner sheet 2552 and outer sheet 2560 may be secured to frame 2555 by sewing, welding, gluing/adhering, stapling, or any other suitable securement method or combination of securement methods. Inner sheet 2552 and/or outer sheet 2560 may be on the distal side of frame 2555, the proximal side of frame 2555, or both such that the frame extends through and along inner sheet 2552 and/or outer sheet 2560. In at least one specific implementation, each of inner sheet 2552 and outer sheet 2560 are supported on a distal side of frame 2555 such that, when implanted, outer sheet 2560 contacts the tissue of the atrial floor while inner sheet 2552 is positioned to interact with and seal against the valve leaflets.

Depending on the particular implementation, inner sheet 2552 and/or outer sheet 2560 may be formed of or include a woven or knit material or fabric that encourages tissue ingrowth. Fabric for inner sheet 2552 and/or outer sheet 2560 may generally have any of the properties or characteristics discussed above with respect to thin sheet 60 of implant 20. Regarding outer sheet 2560, the porosity of the fabric may assist in reducing commissural tricuspid regurgitation. Further reduction of commissural tricuspid regurgitation may be provided by the angulation of frame 2555, which provides close contact between outer sheet 2560 and the commissures in a circumferential manner. For example, with the implant 2500 implanted in the target cardiac valve, tissue in-growth into the fabric of outer sheet 2560 buttresses the myocardium, helping to keep the tissue from expanding further and reducing the potential of future regurgitation. Regarding inner sheet 2552, the porosity of the fabric may assist in reducing central regurgitation by providing an expanded surface relative to central occlusive body 2550 alone against which the valve leaflets may seal. In at least certain implementations, inner sheet 2552 may be formed from PTFE, ePTFE, or a similar low-friction polymer to provide a smooth surface for the native leaflets to abut against.

Frame 2555 may include spokes 2595 from which various arcuate petal portions extend. For example, as discussed above, a distal portion of frame 2555 may include distal or inner arcuate petal portions, such as arcuate petal portion 2557, that support inner sheet 2552. Frame 2555 may further include outer arcuate petal portions, such as arcuate petal portion 2559 configured to support outer sheet 2560. The outer arcuate petal portions may be similar to or otherwise share characteristics and variations of petal portions 100 of implant 20, which are described above in further detail.

Frame 2555 may be made from a variety of super-elastic and/or shape memory materials, including, for example, nickel-titanium alloys (e.g., Nitinol), which may be laser cut from a tube or in the form of drawn wire. The features defined in the shape memory materials may be defined therein via various cutting methods known in the art, include laser, water jet, electrical discharge machining (EDM), stamping, etching, milling, etc.

Like central occluder 50 and frame spokes or struts 95 of implant 20, occlusive assembly 2502 and spokes 2595 may be removable after implantation, leaving second annular surface 2564 formed by outer sheet 2560 in place. In such embodiments, a circumferential suture connection may exist between spokes 2595 and the rest of frame 2555 radially outward of spokes 2595. Thus, this circumferential suture connection may be cut and occlusive assembly 2502 and spokes 2595 may be removed through a catheter, leaving the annular portion of the implant, which then acts as an "annuloplasty" frame.

Like spokes 95 of implant 20, spokes 2595 may proximally extend from central occlusive body 2550 to the outer arcuate petal portions. In certain implementations, spokes 2595 may extend substantially parallel with, and extend along and near to, central longitudinal axis 2570 of implant 2500. When implant 2500 is in the expanded state, spokes 2595 proximally extend from central occlusive body 2550 and laterally radiate away from central longitudinal axis 2570 to the outer arcuate petal portions. In general, spokes 2595 may be configured similar to and have characteristics to spokes of other frame embodiments discussed herein. For example, the dimensional characteristics and variations provided above with respect to frame 55 (and elements thereof) of implant 20 may be similarly applicable to frame 2555 and its components.

Outer arcuate petal portions, such as arcuate petal portion 2559 may be similar to petal portions 100 of implant 20, discussed above. Inner arcuate petal portions, such as arcuate petal portion 2557, may be located between a pair of spokes 2595. When in the expanded state, the inner arcuate petal portions may be straight or curved in a laterally radiating direction. In certain implementations, when curved, the radius of curvature of the inner arcuate petal portions may be like that of spokes 2595 or may differ from that of spokes 2595. Although illustrated as including only singular arcuate members, each inner arcuate petal portion 2557 may instead include multiple arcuate members, such as the inner and outer arcuate members of petal portions 100.

In different implementations, frame 2555 may include different numbers of inner arcuate petal portions. For example, in certain example embodiments, frame 2555 may include between 6 and 8, between 4 and 10, or between 2 and 12 inner acuate petal portions. In the specific implementation illustrated in FIGS. 25 and 26, for example, frame 2555 includes 6 inner arcuate petal portions.

Like frame 55, frame 2555 may engage the atrial tissue via the protruding anchor members 2597, which may be in the form of small barbs. Anchor members 2597 are designed to securely engage the atrial tissue without penetrating through the tissue or to the coronary vessels. Depending on the embodiment, the protruding anchor members or barbs 2597 may be curved to slide before engaging tissue and there may be one or more rows of protruding anchor members 2597. As shown in FIG. 25, for example, frame 2555 includes three offset rows of protruding anchor members 2597 with a distal and intermediate row extending through outer sheet 2560 and a proximal row projecting from a distal end of frame 2555. Further details and alternative configurations provided above with respect to protruding anchor members 105 are similarly applicable to anchor members 2597, including implementations in which 2597 are directionally reversed such that they project distally and radially inward.

Figure 27:
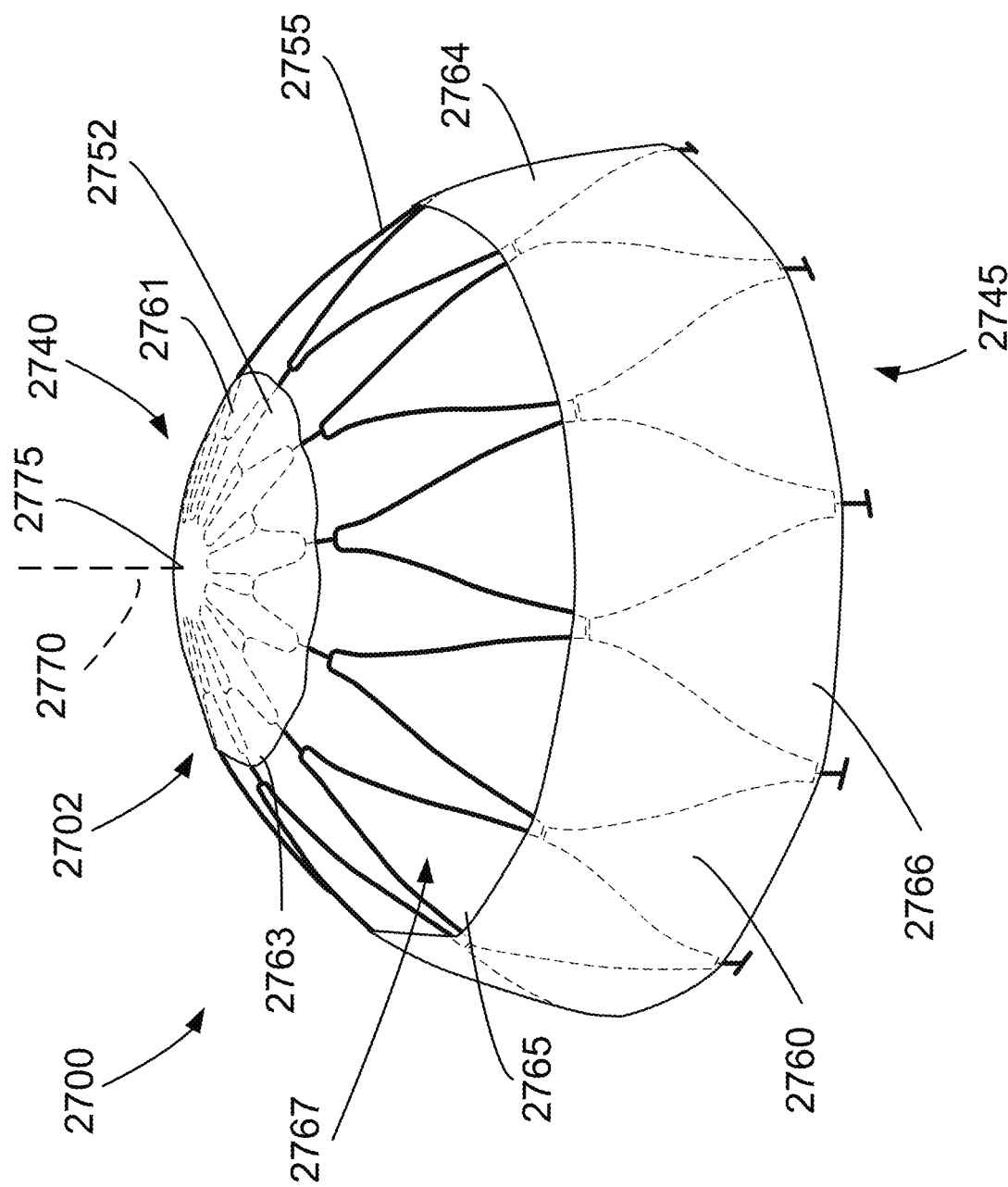
FIG. 27 is perspective distal-end view of a proximally concave implant.
Figure 28:
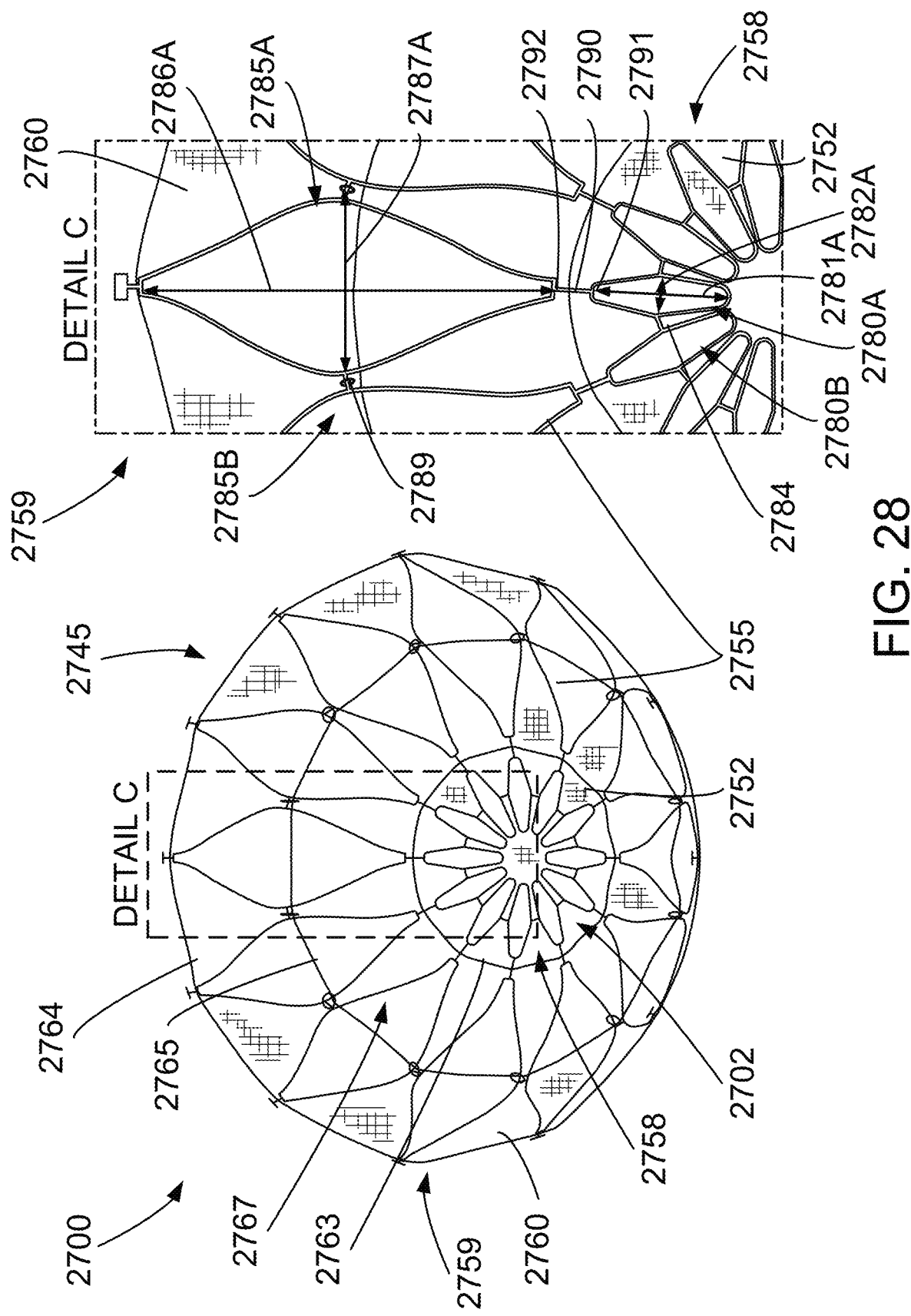
FIG. 28 is a perspective proximal-end view of the implant of FIG. 27.

FIGS. 27 and 28 illustrate another implant 2700 according to the present disclosure. Specifically, FIG. 27 is a perspective distal-side view of implant 2700 while FIG. 28 is a perspective proximal-side view of implant 2700. FIGS. 27 and 28 illustrate implant 2700 when implant 2700 is in an expanded state, such as exists when implant 2700 is implanted in a cardiac valve to be repaired. As illustrated in FIGS. 27 and 28, implant 2700 includes a distal end 2740 (indicated in FIG. 27) and a proximal end 2745. Distal end 2740 serves as the leading end of implant 2700 during implantation.

Implant 2700 includes an occlusive assembly 2702 disposed at distal end 2740. In contrast to occlusive assembly 2502 of implant 2500, occlusive assembly 2702 does not include an occlusive body. Rather, occlusion in occlusive assembly 2702 is provided entirely by an inner sheet 2752, which forms a cap-like structure disposed on distal end 2740. Like implant 2500, implant 2700 further includes a frame 2755 and an outer sheet 2760, with each of inner sheet 2752 and outer sheet 2760 supported on frame 2755. When in the expanded state, frame 2755 radiates laterally outwardly relative to a central longitudinal axis 2770 (indicated in FIG. 27) of implant 2500. In the expanded state, inner sheet 2752 forms a distal surface 2761 and outer sheet 2760 forms an annular surface 2764, each of which is supported on frame 2755.

Distal surface 2761 has a proximal radially outward edge 2763 while annular surface 2764 has a distal radially inward edge 2765 and a proximal radially outward edge 2766. Proximal radially outward edge 2763 of distal surface 2761 and distal radially inward edge 2765 of annular surface 2764 define a central opening 2767 between inner sheet 2752 and outer sheet 2760. Central longitudinal axis 2770 passes through an extreme distal tip 2775 of inner sheet 2752. Given the parabolic shape of frame 2755, implant 2700 may be configured to traverse at least partially up the atrial walls. However, in other implementations, frame 2755 may be configured such that implant 2700 is generally designed to sit on the floor of the atrium. In either case, implant 2700 may generally induce annular reduction and produce a neo-annulus.

Like implant 2500, implant 2700 may be transitioned into a collapsed state, such as during delivery of implant 2700 to the target site. When collapsed, frame 2755, inner sheet 2752, and outer sheet 2760 may collapse symmetrically about central longitudinal axis 2570. Thus, like implant 20 of FIGS. 2-6 and implant 2500, implant 2700 can transition from the collapsed state to the expanded state like an umbrella. Also, like frame 55 of implant 20 and central occlusive body 2550 of implant 2500, frame 2755 of implant 2700 may be biased to self-expand such that implant 2700 self-expands into the expanded state to anchor itself within the target cardiac valve.

Each of inner sheet 2752 and outer sheet 2760 is supported on frame 2755 and secured thereto using any suitable method. For example, and without limitation, inner sheet 2752 and/or outer sheet 2760 may be secured to frame 2755 by suturing, sewing, welding, gluing/adhering, stapling, or any other suitable securement method or combination of securement methods. In certain implementations, inner sheet 2752 or outer sheet 2760 may include a cuff or similar folded structure that is folded over a portion of 2755. In the specific implementation illustrated in FIG. 28, inner sheet 2752 is sutured or otherwise coupled to a distal frame portion 2758 of frame 2755 without such a cuff or fold.

Like sheets previously discussed herein, inner sheet 2752 and/or outer sheet 2760 may be on the distal side of frame 2755, the proximal side of frame 2755, or both such that the frame extends through and along inner sheet 2752 and/or outer sheet 2760. In at least one specific implementation, each of inner sheet 2752 and outer sheet 2760 are supported on a distal side of frame 2755 such that, when implanted, outer sheet 2760 contacts the tissue of the atrial floor and/or atrial wall while inner sheet 2752 is positioned to interact with and seal against the valve leaflets. Like previous embodiments discussed herein, inner sheet 2752 and/or outer sheet 2760 may be formed of or include a woven or knit material or fabric that encourages tissue ingrowth to provide the various advantageous discussed above.

Implementations of this disclosure are not limited to any sizes or dimensions and may be modified or customized to meet the needs of patients and specific applications. Nevertheless, in certain implementations, proximal radially outward edge 2763 of inner sheet 2752 may be from and including about 18 mm to and including about 28 mm. For example, in one specific implementation proximal radially outward edge 2763 may be 23 mm. Similarly, distal radially inward edge 2765 may be from and including about 35 mm to and including about 55 mm. For example, in one specific implementation, distal radially inward edge 2765 may be 44 mm. Finally, proximal radially outward edge 2766 may be from and including about 45 mm to and including about 65 mm. In one specific example, proximal radially outward edge 2766 may be 55 mm.

While implant 20 and implant 2500 each included respective frames that relied primarily on a spoke-based design, frame 2755 illustrates an example of a petal-based frame structure. Referring to FIG. 28, frame 2755 includes distal frame portion 2758, which supports inner sheet 2752, and a proximal frame portion 2759, which supports outer sheet 2760. In general, each of distal frame portion 2758 and proximal frame portion 2759 include a set of circumferentially distributed arcuate petal portions configured to collapse and expand as implant 2700 is similarly collapsed and expanded during delivery and implantation.

As shown in Detail C of FIG. 28, distal frame portion 2758 may include arcuate petal portions that may be ovate, diamond-shaped, or that have other elongate shape (e.g., generally diamond shaped albeit with rounded vertices or curved edges). Each such arcuate petal portion may be defined by respective major and minor axes. For example, as shown in Detail C, arcuate petal portion 2780A may have a major axis 2781A that extends in a substantially longitudinal direction and a minor axis 2782A that extends in a circumferential direction. In certain implementations, adjacent arcuate petal portions may be joined at or near the vertices along the minor axis, which are generally referred to as co-vertices. For example, and as indicated in FIG. 28, arcuate petal portion 2780A and arcuate petal portion 2780B are joined at a junction 2784 disposed distal the co-vertices of arcuate petal portion 2780A and arcuate petal portion 2780B.

Proximal frame portion 2759 may similarly include arcuate petal portions that may be ovate, diamond-shaped, or have another elongate shape. Each such arcuate petal portion may be defined by respective major and minor axes. For example, arcuate petal portion 2785A may have a major axis 2786A that extends in a substantially longitudinal direction and a minor axis 2787A that extends in a circumferential direction. In certain implementations, adjacent arcuate petal portions of proximal frame portion 2759 may be joined at or near the vertices along the minor axis (i.e., the co-vertices of the arcuate petal portions). For example, arcuate petal portion 2785A and arcuate petal portion 2785B are joined at a junction 2789 disposed at the corresponding co-vertices of arcuate petal portion 2785A and arcuate petal portion 2785B.

As further illustrated in FIG. 28, arcuate petal portions of distal frame portion 2758 may be joined to respective arcuate petal portions of proximal frame portion 2759. For example, arcuate petal portion 2780A is coupled to arcuate petal portion 2785A by a longitudinal member 2790 extending between a proximal vertex 2791 of arcuate petal portion 2780A and a distal vertex 2792 of arcuate petal portion 2785A.

Like previous frames discussed herein, frame 2755 may be made from a variety of super-elastic and/or shape memory materials, including, for example, nickel-titanium alloys (e.g., Nitinol), which may be laser cut from a tube or in the form of drawn wire. The features defined in the shape memory materials may be defined therein via various cutting methods known in the art, include laser, water jet, electrical discharge machining (EDM), stamping, etching, milling, etc.

Depending on the embodiment, frame 2755 may include different numbers of inner and/or outer arcuate petal portions. For example, in certain example embodiments, frame 2755 may include between 10 and 14, between 8 and 16, or between 6 and 18 inner and outer arcuate petal portions. In the specific implementation illustrated in FIGS. 27 and 28, for example, frame 2755 includes 12 each of inner and outer arcuate petal portions with each inner arcuate petal portion joined to a respective outer arcuate petal portion. In other implementations, the number of inner arcuate petal portions may differ from the number of outer arcuate petal portions. For example, frame 2755 may include twice as many inner arcuate petal portions as outer petal portions. Moreover, not every inner arcuate petal portion may be joined to a corresponding outer arcuate petal portion or vice versa regardless of whether the number of inner and outer arcuate petal portions matches. So, for example, in one implementation, an implant may include twice then number of inner arcuate petal portions as outer arcuate petal portions and every other inner arcuate petal portion may be joined to an outer arcuate petal portion. In another implementation, the number of inner and outer arcuate petal portions may be the same; however, joining may still only be between every other inner and outer arcuate petal portion.

As shown in FIGS. 27 and 28, each inner arcuate petal portion is uniform as is each outer arcuate petal portion. In other implementations, the inner and outer arcuate petal portions may vary in any direction. For example, the inner arcuate petal portions may alternate between arcuate petal portions having a first major axis dimension and arcuate petal portions have a second major axis dimension different than the first major axis dimension.

Other examples of alternative frame configurations are discussed below in the context of FIGS. 31-33.

Although not illustrated in FIGS. 27 and 28, frame 2755 may engage atrial tissue via protruding anchor members, like protruding anchor members 105 of implant 20 or protruding anchor members 2597 or implant 2500, discussed above.

VIII. Alternative Implant Frame Shapes

The overall shape of implants according to the present disclosure when in the expanded state may vary across implementations to address various needs of a patient. Among other things, implant shape may be varied to accommodate variations in patient anatomy and pathology. For example, in cases where a patient may have weakened valves or valves exhibiting reduced travel, an implant configuration in which an occlusive assembly is positioned deeper into the ventricle may be advantageous such that contact and sealing between the occlusive assembly and leaflet occurs earlier in the leaflet's travel. In contrast, a more planar or flat implant structure in which the sheets of the implant cover a greater proportion of the tricuspid valve structure may be more advantageous when commissural regurgitation is present despite substantially normal leaflet function. These and other considerations are described below in further detail.

Figure 29A:
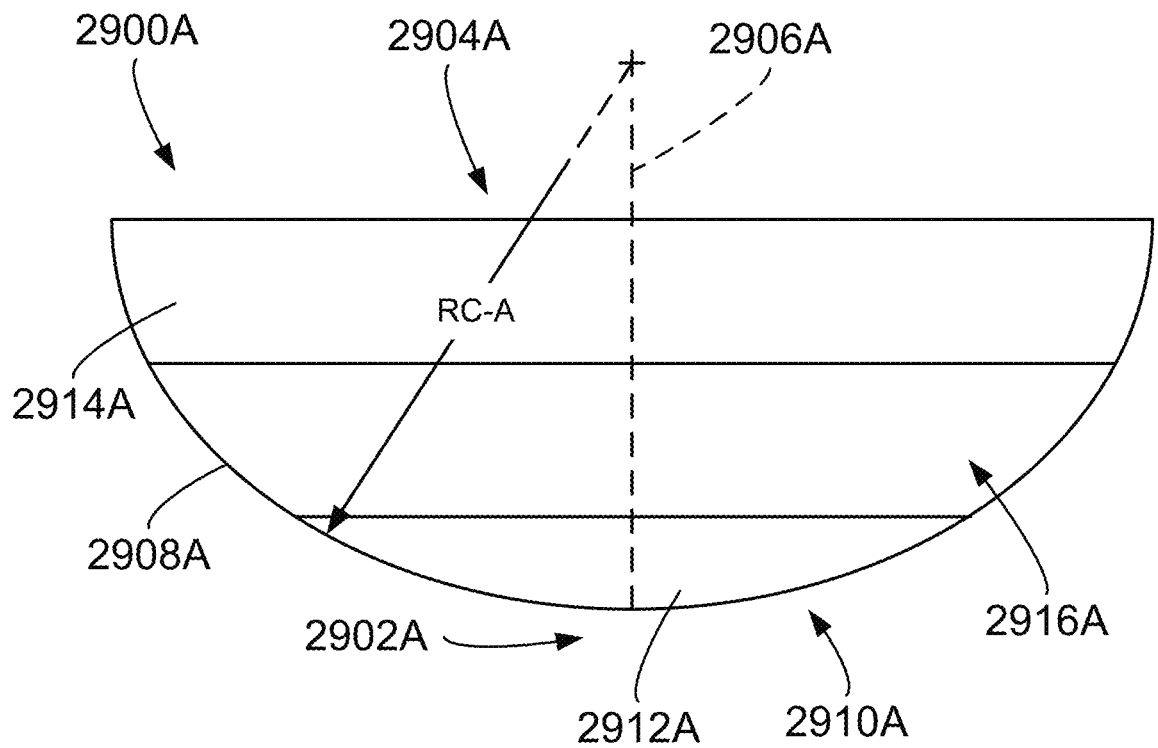
FIG. 29A is a simplified elevation view of a proximally concave implant.
Figure 29B:
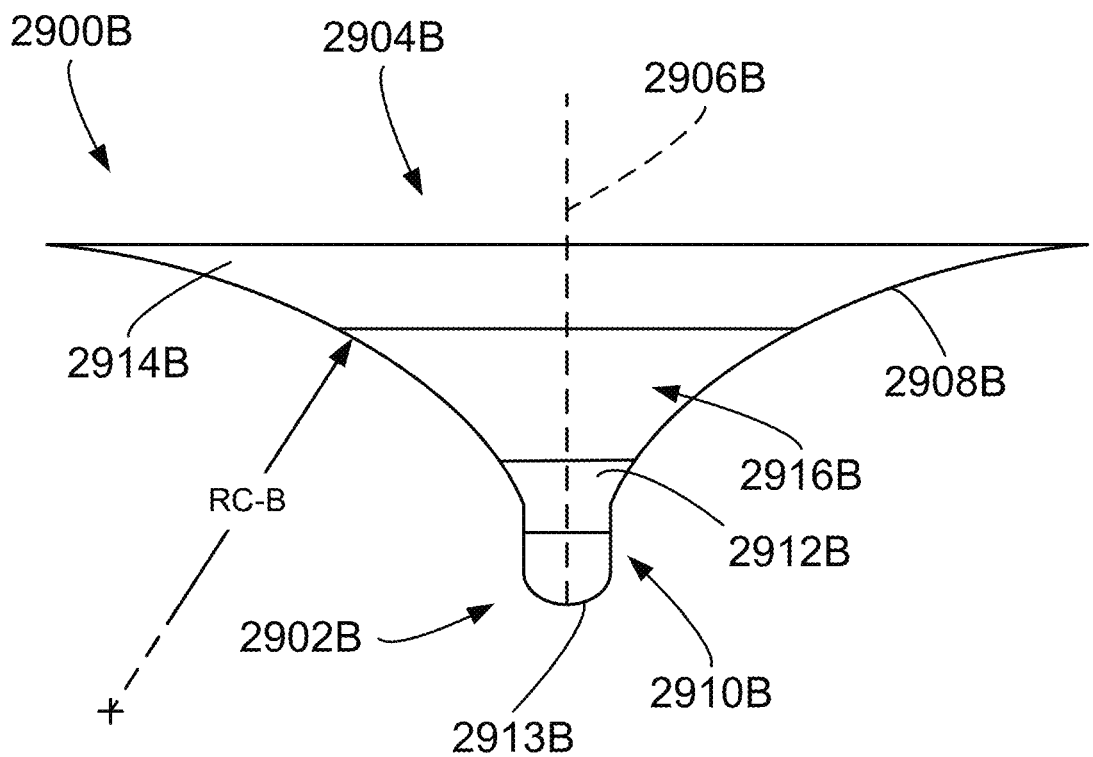
FIG. 29B is a simplified elevation view of a distally concave implant.
Figure 29C:
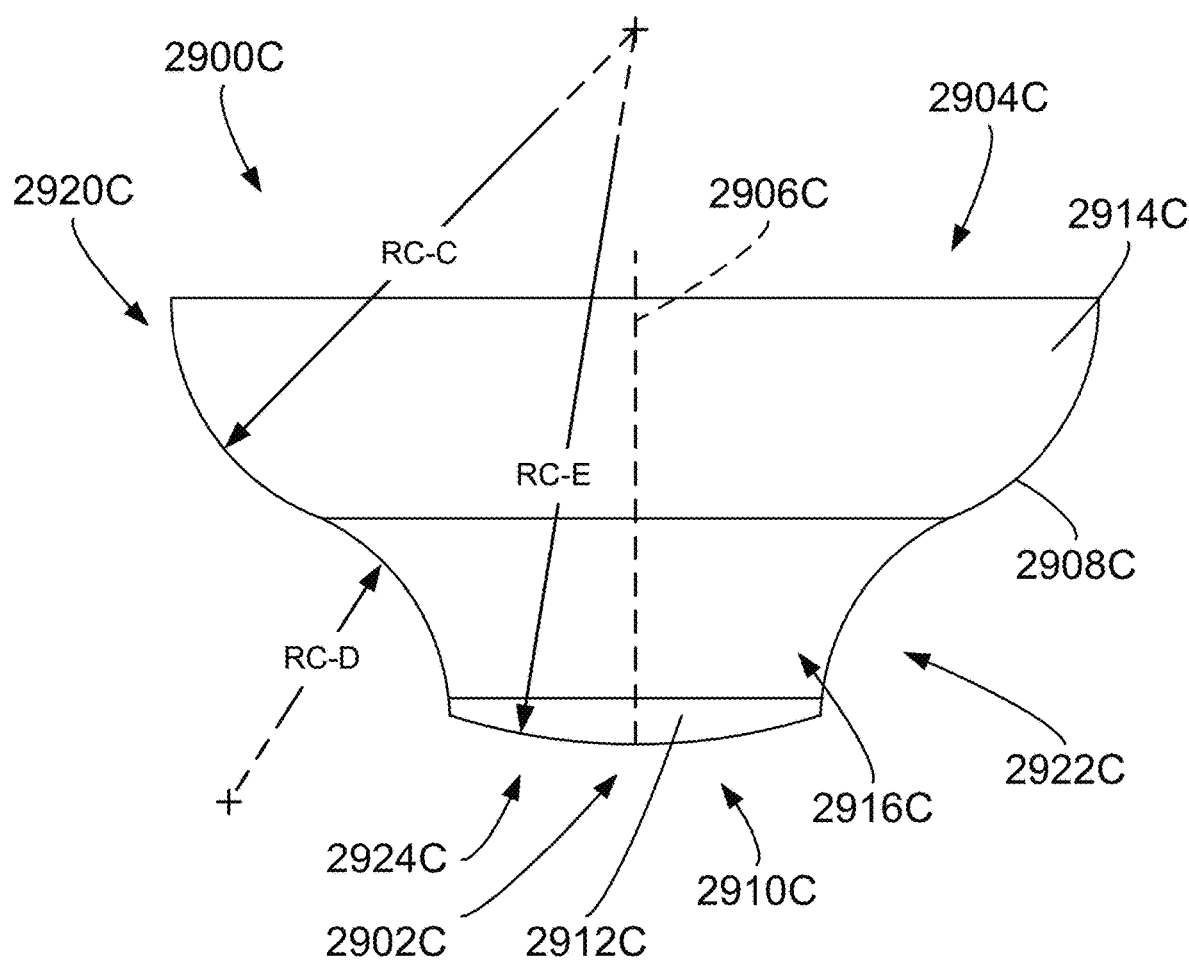
FIG. 29C is a simplified elevation view of an implant including a proximal portion having a proximally concave shape and a distal portion having a distally concave shape.

In one aspect, implants according to the present disclosure may vary in curvature when in the expanded state. Examples of varying curvature are provided in FIGS. 29A-29C. More specifically, FIG. 29A is an elevation view of an implant 2900A that has a proximally concave shape when deployed/expanded, FIG. 29B is an elevation view of an implant 2900B that has a distally concave shape when deployed/expanded, FIG. 29C is an elevation view of an implant 2900C including a proximally concave proximal portion and a distally concave distal portion. For clarity and simplicity, each of implant 2900A-2900C are shown in a simplified view in which overall shape is emphasized and certain elements of each implant are omitted. Accordingly, and unless stated otherwise, implants 2900A-2900C may generally include elements of and be in accordance with any other implementation discussed herein. For example, FIGS. 29A-29C generally omit details regarding the frames of the corresponding implants; however, it should be understood that such frames may be in accordance with any frame style disclosed herein.

Referring first to FIG. 29A, implant 2900A includes a distal end 2902A and a proximal end 2904A such that a longitudinal axis 2906A of implant 2900A extends between distal end 2902A and proximal end 2904A. Implant 2900A includes a frame 2908A that supports an occlusive assembly 2910A at distal end 2902A. As shown, occlusive assembly 2910A includes an inner sheet 2912A; however, in other implementations, occlusive assembly 2910A may include an occlusive body instead of or in addition to inner sheet 2912A. For example, occlusive assembly 2910A may include a bulb- or bullnose-shaped occluder about which inner sheet 2912A extends. Implant 2900A further includes an outer sheet 2914A supported on frame 2908A at proximal end 2904A such that an annular opening 2916A is defined between inner sheet 2912A and outer sheet 2914A.

FIG. 29A shows implant 2900 in the expanded state (e.g., following deployment). As shown, implant 2900A has a proximally concave shape defined by a radius of curvature (RC-A) such that implant 2900A has an overall bowl-like shape. Implant 2700 of FIGS. 27 and 28 is an example of a proximally concave implant according to this disclosure and is discussed above in further detail. Notably, while illustrated as being hemispherical, implant 2900A may alternatively have an ovoid or similar rounded but non-spherical shape.

RC-A may differ in implementations of this disclosure depending on the specific application and needs of the patient. For example, when the overall diameter of proximal end 2904A is held constant, RC-A generally controls the position of distal end 2902A and occlusive assembly 2910A relative to proximal end 2904A. More specifically, as RC-A increases, implant 2900A takes on a shallower geometry when in the expanded shape such that distal end 2902A is closer to the valve annulus following deployment. Conversely, as RC-A decreases, implant 2900A takes on a deeper shape such that distal end 2902A and occlusive assembly 2910A deploy further within the ventricle. As noted above, placement of occlusive assembly 2910A relative to the valve annulus determines how and when the valve leaflets contact and seal against occlusive assembly 2910A and, as a result, RC-A may be chosen to account for various needs and idiosyncrasies of a particular patient.

For example, the proximally concave/distally convex shape illustrated in FIG. 29A generally includes larger and more accessible gaps as compared to the distally concave/proximally convex design illustrated in FIG. 29B and discussed below in further detail. As a result, proximally concave implants according to the present disclosure may allow for easier and more accurate placement of other cardiac devices, such as pacemaker leads, though the implant. Proximally concave implants according to this disclosure may also be readily inverted. Such invertibility can facilitate removal of the implant at a later date as the implant can be funneled and pulled back into a retrieval catheter.

Regardless of concavity, implants according to this disclosure having frames formed of metal or other radiopaque materials may further facilitate placement of a pacemaker lead by being visible on fluoroscopy and providing a target for delivering the pacemaker lead. The frame of the implant may also provide constraints for the pacemaker lead to reduce movement of the lead following delivery and implantation. Among other things, such reinforcement of the lead may prevent or reduce the likelihood that the pacemaker lead may obstruct or otherwise interfere with movement of the valve leaflets.

Referring next to FIG. 29B, implant 2900B includes a distal end 2902B and a proximal end 2904B such that a longitudinal axis 2906B of implant 2900B extends between distal end 2902B and proximal end 2904B. FIG. 29B shows implant 2900B in the expanded state about longitudinal axis 2906B. Implant 2900B includes a frame 2908B that supports an occlusive assembly 2910B at distal end 2902B and that is shown including an inner sheet 2912B as well as an occlusive body 2913B. In other implementations, occlusive assembly 2910B may instead include only one of inner sheet 2912B and occlusive body 2913B. Implant 2900B further includes an outer sheet 2914B supported on frame 2908B at proximal end 2904B such that an annular opening 2916B is defined between inner sheet 2912B and outer sheet 2914B. When in the expanded state (e.g., following deployment) implant 2900B has a distally concave shape defined by a radius of curvature (RC-B) such that implant 2900B has an overall funnel-like shape. Examples of implants with a similar shape include implant 20 and implant 2500, discussed above in further detail.

Like RC-A of implant 2900A, RC-B of implant 2900B may differ in implementations of this disclosure depending on the specific application and needs of the patient. Among other things, the distally concave design of implant 2900B ensures that initial contact between the valve leaflets and implant 2900B is with occlusive assembly 2910B as opposed to a portion of frame 2908B, as may occur in the distally concave design of implant 2900A. More generally, the distally concave shape reduces the overall size of the implant portion within the ventricle, reducing the likelihood that the implant may obstruct or otherwise interfere with cardiac structures and their respective functions. For example, the distally concave shape reduces contact between the valve leaflets and the implant, thereby reducing the likelihood that the implant will interfere with or otherwise impede travel of the leaflets. As another example, the distally convex shape may reduce the likelihood that the implant will interfere with or obstruct the coronary sinus or similar vessels of the heart.

Implant 2900C includes a distal end 2902C and a proximal end 2904C such that a longitudinal axis 2906C of implant 2900B extends between distal end 2902C and proximal end 2904C. FIG. 29C shows implant 2900C in the expanded state about longitudinal axis 2906C. Implant 2900C includes a frame 2908C that supports an occlusive assembly 2910C at distal end 2902C and that is shown including an inner sheet 2912C. In other implementations, occlusive assembly 2910C may further or alternatively include an occlusive body. Implant 2900C also includes an outer sheet 2914C supported on frame 2908C at proximal end 2904C such that an annular opening 2916C is defined between inner sheet 2912C and outer sheet 2914C.

Implant 2900C includes both proximally and distally concave portions. More specifically, 2900C includes proximal portion 2920C that has a proximally concave shape. Implant 2900C transitions into a distal portion 2922C that has a distally concave shape. In the implementation illustrated in FIG. 29, distal portion 2922C further transitions into a proximally concave cap portion 2924C that includes occlusive assembly 2910C and, more specifically, inner sheet 2912C. In other implementations, distal portion 2922C may instead terminate in an occlusive body, such as central occluder 50 of implant 20 or central occlusive body 2550 of implant 2500.

When in the expanded state (e.g., following deployment) the shape of implant 2900C may be defined by at least two radii of curvature. More specifically, the shape of implant 2900C may be defined by a radius of curvature (RC-C) corresponding to proximal portion 2920C (i.e., the proximally concave portion of implant 2900C) and a radius of curvature (RC-D) corresponding to the distal portion 2922C (i.e., the distally concave portion of implant 2900C). To the extent an implementation of this disclosure further includes proximally concave cap portion 2924C, implant 2900C may be further defined by a radius of curvature (RC-E) corresponding to proximally concave cap portion 2924C. In certain implementations, RC-E and RC-C may be the same; however RC-E and RC-C may also differ such that proximally concave cap portion 2924C may have a more or less pronounced curvature than proximal portion 2920C.

Figure 30A:
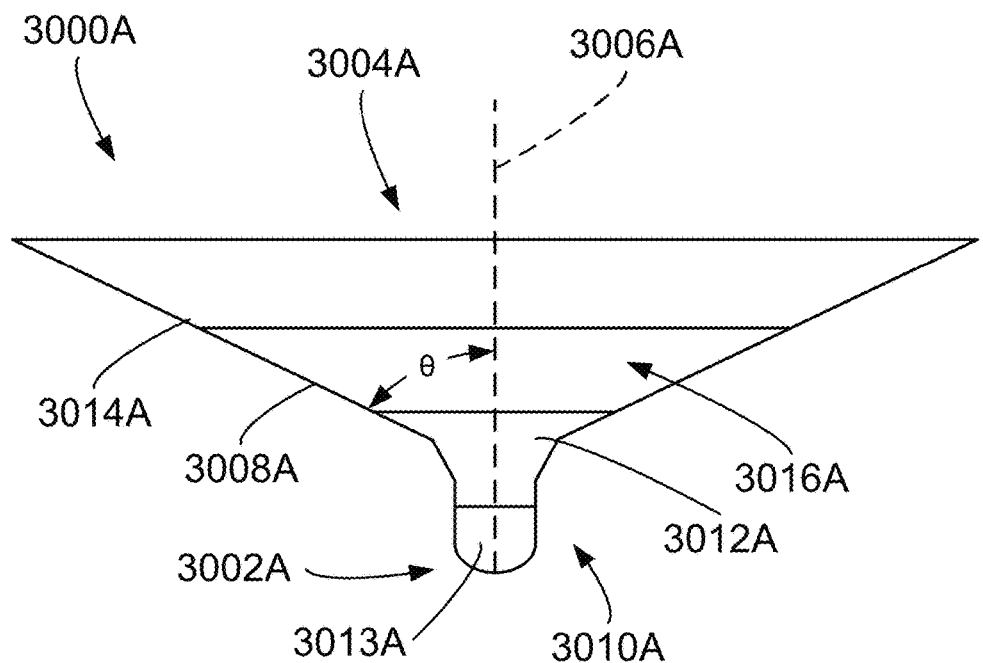
FIG. 30A is a simplified elevation view of a frustoconical implant.
Figure 30B:
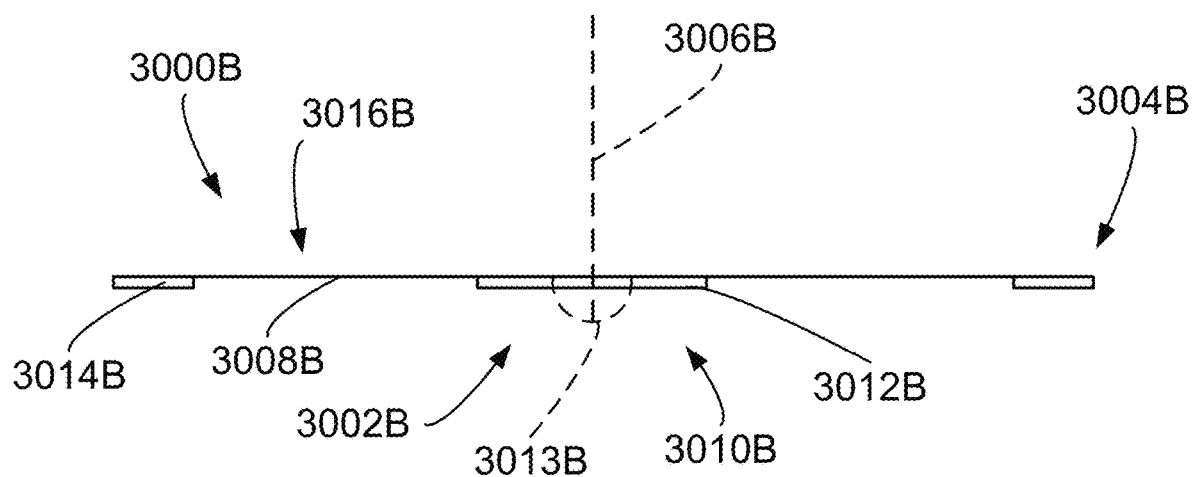
FIG. 30B is a simplified elevation view of a planar implant.

While each of implant 2900A, implant 2900B, and implant 2900C have an overall curved shape, implants according to this disclosure may also have non-curved shapes when deployed. Examples of such non-curved implants are provided in FIGS. 30A and 30B. More specifically, FIG. 30A is an elevation view of an implant 3000A having a conical shape when deployed while FIG. 30B is an elevation view of an implant 3000B having a flat or planar shape when deployed. Like FIGS. 29A and 29B, for clarity and simplicity, each of implant 3000A and implant 3000B are shown in a simplified view in which overall shape is emphasized and certain elements of each implant are omitted. Accordingly, and unless stated otherwise, implant 3000A and implant 3000B may generally include elements of and be in accordance with any other implementation discussed herein.

Referring to FIG. 30A, implant 3000A includes a distal end 3002A and a proximal end 3004A such that a longitudinal axis 3006A of implant 3000A extends between distal end 3002A and proximal end 3004A. Implant 3000A includes a frame 3008A that supports an occlusive assembly 3010A at distal end 3002A. As shown, occlusive assembly 3010A includes an inner sheet 3012A and an occlusive body 3013A. In other implementations, occlusive assembly 3010A may instead include only one of inner sheet 3012A and occlusive body 3013A. Implant 3000A further includes an outer sheet 3014A supported on a proximal portion of frame 3008A such that an annular opening 3016A is defined between inner sheet 3012A and outer sheet 3014A.

FIG. 30A shows implant 3000 in the expanded state (e.g., following deployment). As shown and in contrast to the curved funnel shape of implant 2900B, implant 3000A has a straight-sided funnel shape. Stated differently, when deployed, implant 3000A has a distally expanding conical or frustoconical shape.

Like implant 2900A and implant 2900B, implant 3000A may be modified to vary the degree to which occlusive assembly 3010A enters the ventricle when implant 3000A is deployed within the heart. For example, the general shape of implant 3000B may be determined by an angle θ, which may be defined as the angle between the sides of frame 3008A and longitudinal axis 3006A of implant 3000A when implant 3000A is in the expanded/deployed state. Assuming other dimensions of implant 3000A (e.g., maximum diameter at proximal end 3004A) remain substantially constant, varying θ changes overall length of implant 3000A when expanded and, as a result, the depth of occlusive assembly 3010A within the ventricle. More specifically, reducing θ increases the overall length of implant 3000A and the depth of occlusive assembly 3010A within the ventricle when implant 3000A is deployed. Conversely, increasing θ reduces the overall length of implant 3000A when deployed (e.g., results in implant 3000A being more planar in the expanded state) and the depth of occlusive assembly 3010A within the ventricle.

Referring next to FIG. 30B, implant 3000B expands into a flat or planar shape when deployed. Implant 3000B includes a radially inward portion 3002B and a radially outward portion 3004B relative to a longitudinal axis 3006B. When in the collapsed state (e.g., when implant 3000B is collapsed about longitudinal axis 3006B during delivery), radially inward portion 3002B forms a distal or leading end of implant 3000B while radially outward portion 3004B forms a proximal end of implant 3000B. Like other implants disclosed herein, implant 3000B includes a frame 3008B that supports an occlusive assembly 3010B at radially inward portion 3002B. As shown, occlusive assembly 3010B includes an inner sheet 3012B. In other implementations, occlusive assembly 3010B may further or alternatively include an occlusive body 3013B, which FIG. 30B shows in dashed lines. Implant 3000B further includes an outer sheet 3014B supported on a proximal portion of frame 3008B such that an annular opening 3016B is defined between inner sheet 3012A and outer sheet 3014B.

Planar implants, such as implant 3000B, may be particularly advantageous in cases where regurgitation results despite substantially normal valve leaflet travel. When deployed, implant 3000B may be positioned along the floor of the atrium across the valve annulus with occlusive assembly 3010B centrally located or approximately centrally located. In implementations in which occlusive assembly 3010B includes occlusive body 3013B, occlusive body 3013B may project into the valve annulus or across the valve annulus into the ventricle, depending on its size and shape. When the valve is in the closed position and with implant 3000B properly positioned, the valve leaflets contact and seal against occlusive assembly 3010B. In this position, portions of occlusive assembly 3010B, such as inner sheet 3012B, may extend over the leaflets and, in particular, the commissures between the leaflets. By doing so, inner sheet 3012B provides an additional and expanded sealing surface for the leaflets and may cover at least a portion of commissural gaps that may be present, thereby reducing regurgitation. In addition to inner sheet 3012B, additional regurgitation reduction may be provided by outer sheet 3014B, which may similarly seal against the leaflets and cover commissural gaps that may be present toward the outward edge of the valve annulus.

IX. Alternative Frame Configurations

As previously discussed, implants according to the present disclosure include a frame configured to support a distal occlusive assembly. The frame may further support or otherwise be coupled to one or more thin sheets or similar structures. In certain implementations such sheets may include a proximal or outer sheet configured to contact the atrial floor and/or a distal or inner sheet included in the occlusive assembly (e.g., as a "skirt" extending circumferentially around an occlusive body of the occlusive assembly).

In addition to providing structural integrity, frames of implants according to this disclosure are configured to be expandable about a longitudinal axis of the implant. More specifically, frames of implants according to the present disclosure are configured to transition between a collapsed state and an expanded state. The collapsed state may correspond, for example, to a state of the implant during delivery using a delivery tool, such as tool 15 (shown in FIG. 1A), tool 1115 (shown in FIGS. 11A-11B), or delivery tool 300 (shown in FIG. 13), each of which is discussed above in detail. In contrast, the expanded state may correspond to a state of the implant following delivery and deployment within a patient heart. Implant frames according to this disclosure may be biased into the expanded state such that the implant transitions into the expanded state absent resistance provided by a delivery tool. For example, and with reference to FIG. 16, tension control members 320 of the delivery tool may be coupled to a tension control line 200 of the implant such that by applying tension to the tension control members 320, a user may resist expansion of the implant. In certain implementations, a user may apply sufficient tension to collapse the implant (e.g., to transition the implant from the expanded state to the collapsed state).

This disclosure previously described various example frame styles. For example, FIGS. 2-8 and 12 include a first style of frame for a distally concave implant in which radially extending spokes support arcuate petal portions circumferentially distributed about a central occluder. FIGS. 25 and 26 illustrate a similar frame style albeit with the further inclusion of inner arcuate petal portions configured to support an inner sheet. FIGS. 27 and 28 introduce the concept of a proximally concave frame formed by joining an inner/distal set of circumferentially distributed arcuate petals to an outer/proximal set of circumferentially distributed arcuate petals. FIGS. 29A-30B expand on these general frame styles by providing additional examples of overall frame shapes and configurations.

Figure 31:
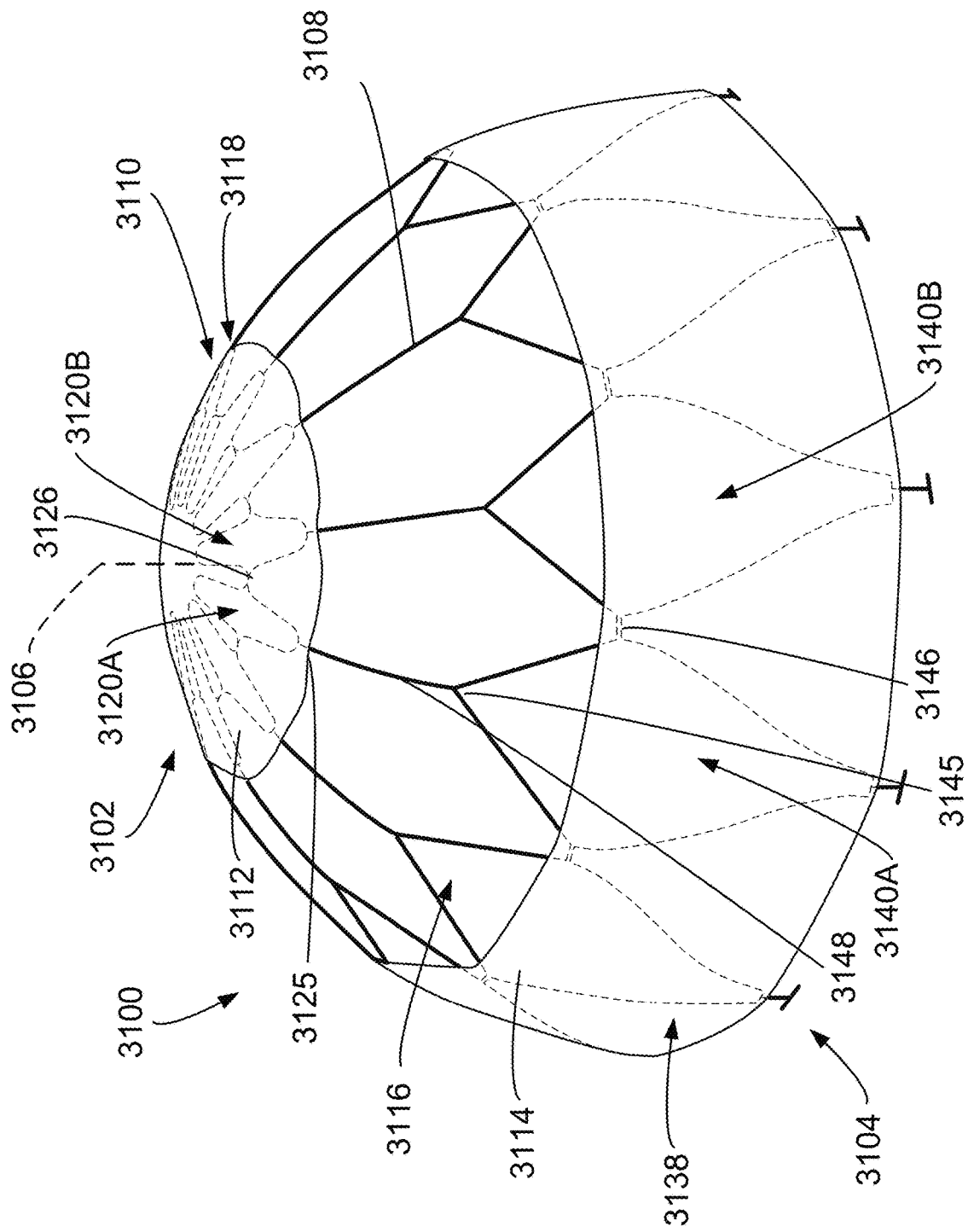
FIG. 31 is a perspective distal-end view of an implant having a frame including arcuate petal portions connected by elongate longitudinal members.
Figure 32:
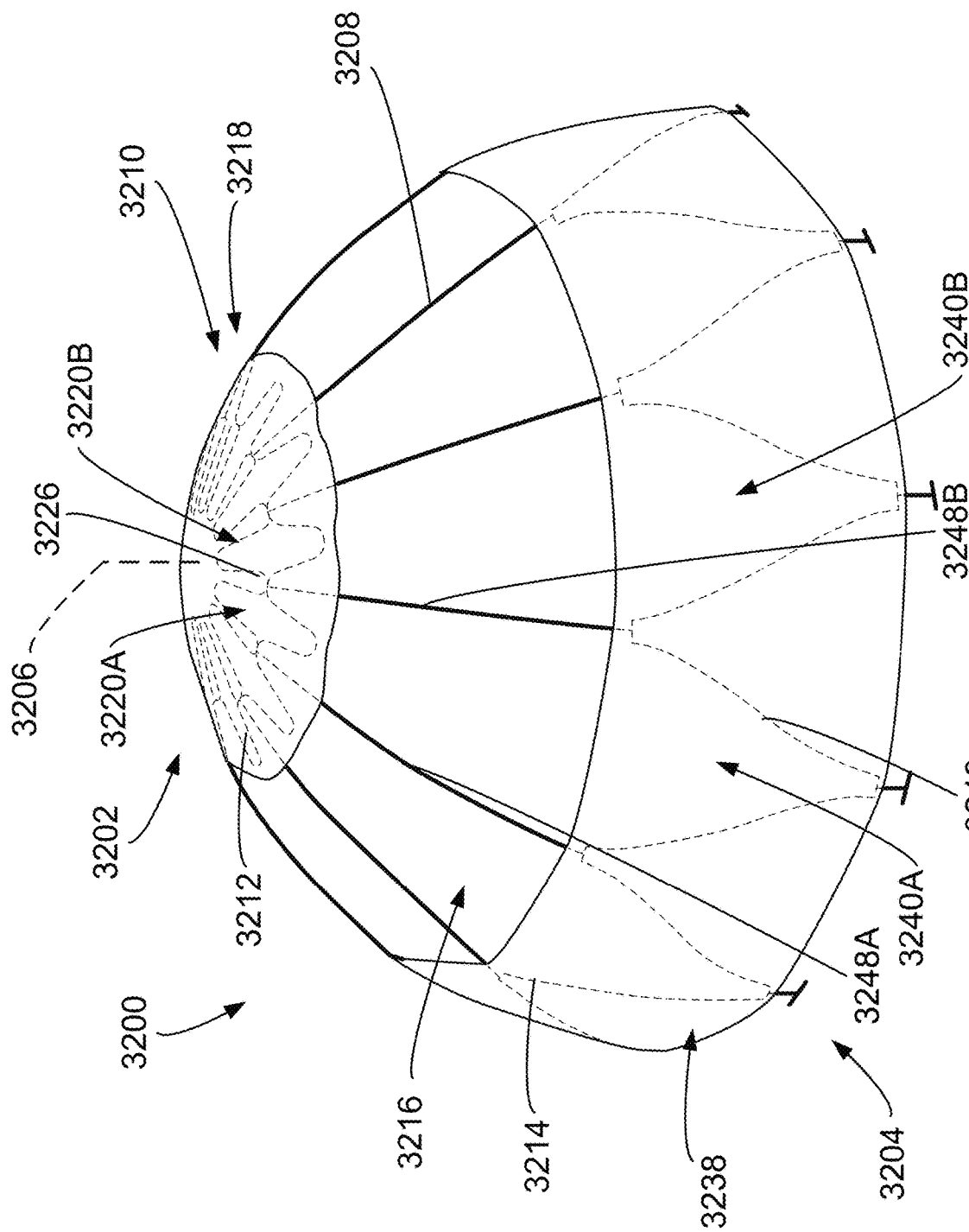
FIG. 32 is a perspective distal-end view of an implant having a frame including distally open arcuate petal portions.
Figure 33:
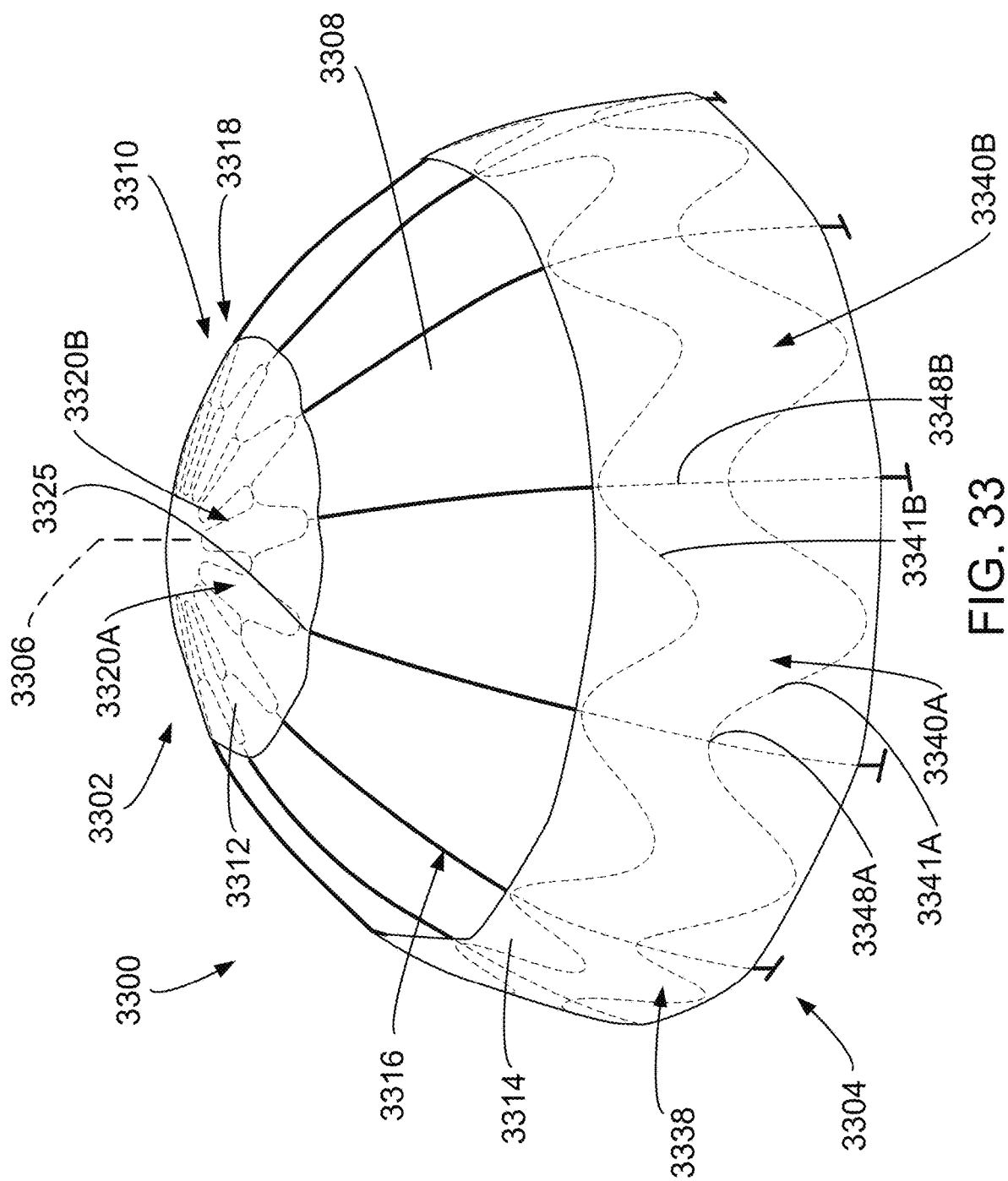
FIG. 33 is a perspective distal-end view of an implant having arcuate petal portions formed by arcuate members extending between longitudinal members.

To further illustrate the scope of frames contemplated by this disclosure, FIGS. 31-33 provide additional examples of frame styles that may be used in implants according to the present disclosure. Notably, while each of FIGS. 31-33 describe the alternative frame styles as applied to a proximally concave implant (similar to implant 2700 of FIGS. 27 and 28), the concepts and structures illustrated in FIGS. 31-33 may be applied to implants having distally concave, frustoconical, planar, or other overall shapes. Notably, FIGS. 31-33 omit certain features of the illustrated implants for purposes of clarity. For example, each of FIGS. 31-33 omit a backside of the depicted implants (relative to the illustrated perspective) to more clearly illustrate the structure and configuration of the frames of the implants.

FIG. 31 illustrates an implant 3100 having a first alternative frame configuration. Implant 3100 includes a distal end 3102 and a proximal end 3104 such that a longitudinal axis 3106 of implant 3100 extends between distal end 3102 and proximal end 3104. Implant 3100 includes a frame 3108 that supports an occlusive assembly 3110 at distal end 3102. As shown, occlusive assembly 3110 includes an inner sheet 3112; however, in other implementations, occlusive assembly 3110 may include an occlusive body instead of or in addition to inner sheet 3112. Implant 3100 further includes an outer sheet 3114 supported on a proximal portion of frame 3108 such that an annular opening 3116 is defined between inner sheet 3112 and outer sheet 3114.

Similar to frame 2755 of implant 2700, frame 3108 of implant 3100 includes a distal frame portion 3118 including a first set of circumferentially distributed arcuate petal portions, such as arcuate petal portion 3120A and arcuate petal portion 3120B, and a proximal frame portion 3138 including a second set of circumferentially distributed arcuate petal portions, such as arcuate petal portion 3140A and arcuate petal portion 3140B. As described in the context of FIGS. 27 and 28, above, arcuate petals portions according to this disclosure may be ovate, diamond-shaped, or have any similar elongate shape (e.g., generally diamond shaped albeit with rounded vertices or curved edges). More generally, arcuate petal portions according to this disclosure may have any suitable shape that enables collapsing and expanding of the frame and other functionality described herein (e.g., support of fabric sheets, such as inner sheet 3112 and outer sheet 3114).

As shown in FIG. 31, adjacent arcuate petal portions of distal frame portion 3118 may be joined at or near their respective co-vertices. For example, arcuate petal portion 3120A and arcuate petal portion 3120B are joined at a junction 3126 disposed at the corresponding co-vertices of arcuate petal portion 3120A and arcuate petal portion 3120B. Adjacent arcuate petal portions of proximal frame portion 3138 likewise may be joined at or near their respective co-vertices. For example, arcuate petal portion 3140A and arcuate petal portion 3140B are joined at a junction 3146 disposed at the corresponding co-vertices of arcuate petal portion 3140A and arcuate petal portion 3140B

Arcuate petal portions of distal frame portion 3118 may be joined to respective arcuate petal portions of proximal frame portion 3138. For example, arcuate petal portion 3120A is coupled to arcuate petal portion 3140A by a longitudinal member 3148 extending between a proximal vertex 3125 of arcuate petal portion 3120A and a distal vertex 3145 of arcuate petal portion 3140A.

As illustrated in FIG. 31, longitudinal member 3148 extending between arcuate petal portion 3120A and arcuate petal portion 3140A is substantially longer than longitudinal member 2790 extending between arcuate petal portion 2780A and arcuate petal portion 2785A of implant 2700 (shown in FIG. 28).

Although FIG. 31 illustrates longitudinal members (e.g., longitudinal member 3148) as extending between the proximal vertices of the first set of arcuate petal portions and the distal vertices of the second set of arcuate petal portions, in other implementations, longitudinal members may extend between other locations of frame 3108. For example, in certain implementations, longitudinal members may be offset from the arcuate petal portions such that the longitudinal members extend between the circumferential junctions of the arcuate petal portions. So, for example and with reference to FIG. 31, longitudinal members may extend between the junctions of the first set of arcuate petal portions (e.g., junction 3126) and the junctions of the second set of arcuate petal portions (e.g., junction 3146). In other implementations, the first set of arcuate petal portions can be rotationally offset from the second set of arcuate petal portions such that the junctions of one set align with the vertices of the other set. In such implementations, longitudinal members may extend between the junctions of one set and the vertices of the other. So, for example, longitudinal members may extend between junctions of the first set of arcuate petal portions (e.g., junction 3126) and the distal vertices of the second set of arcuate petal portions (e.g., distal vertex 3145). Alternatively, longitudinal members may extend between the proximal vertices of the first set of arcuate petal portions (e.g., proximal vertex 3125) and the junctions of the second set of arcuate petal portions (e.g., junction 3146).

In implementations of the present disclosure, either of the inner sheet or the outer sheet may define one or more internal pockets. For example, in certain implementations, the sheet may include two or more layers stitched or otherwise coupled together to form internal pockets between adjacent layers. In one implementation, the adjacent layers may include a first layer disposed on a proximal or inner surface of the implant frame and a second layer disposed on a distal or outer surface of the implant frame such that the frame also extends between the layers. In other implementations, the layers forming the internal pockets may be disposed entirely on the proximal/inner surface of the frame or the distal/outer surface of the frame. Pockets formed in this way may be filled, such as with additional layers of fabric, batting, or a water-absorbing material, such as a hydrogel. In such cases, the filling generally forms a pad that may increase the distance between the occluding surface/ sheet and the underlying frame of the implant, thereby preventing and padding contact between valve leaflets and the frame.

FIG. 32 illustrates an implant 3200 with another alternative frame configuration. Implant 3200 includes a distal end 3202 and a proximal end 3204 such that a longitudinal axis 3206 of implant 3200 extends between distal end 3202 and proximal end 3204. Implant 3200 includes a frame 3208 that supports an occlusive assembly 3210 at distal end 3202. As shown, occlusive assembly 3210 includes an inner sheet 3212; however, in other implementations, occlusive assembly 3210 may include an occlusive body instead of or in addition to inner sheet 3212. Implant 3200 further includes an outer sheet 3214 supported on a proximal portion of frame 3208 such that an annular opening 3216 is defined between inner sheet 3212 and outer sheet 3214.

Frame 3208 of implant 3200 includes a distal frame portion 3218 including a first set of circumferentially distributed arcuate petal portions, such as arcuate petal portion 3220A and arcuate petal portion 3220B, and a proximal frame portion 3238 including a second set of circumferentially distributed arcuate petal portions, such as arcuate petal portion 3240A and arcuate petal portion 3240B.

The first or inner set of arcuate petal portions of implant 3200 are shown as being substantially similar to those of implant 3100. The second set arcuate petal portions of implant 3200, on the other hand, have a distally open shape in contrast to the ovate shape of implant 3100. More specifically, each arcuate petal portion of the second set of arcuate petal portions is formed by a pair of longitudinal members and an arcuate frame portion. For example, arcuate petal portion 3240A is formed by a longitudinal member 3248A, a longitudinal member 3248B, and an arcuate frame portion 3249, which extends between longitudinal member 3248A and longitudinal member 3248B. As illustrated, each longitudinal member extends from a respective junction of the first set of arcuate petal portions. For example, longitudinal member 3248A extends from a junction 3226 between arcuate petal portion 3220A and arcuate petal portion 3220B. Like noted above with respect to implant 3100, the first and second set of arcuate petal portions of implant 3200 may be rotationally offset from the configuration illustrated in FIG. 32 such that the longitudinal members instead extend from proximal vertices (e.g., proximal vertex 3125) of the first set of arcuate petal portions.

FIG. 33 illustrates an implant 3300 having yet another alternative frame configuration. Implant 3300 includes a distal end 3302 and a proximal end 3304 such that a longitudinal axis 3306 of implant 3300 extends between distal end 3302 and proximal end 3304. Implant 3300 includes a frame 3308 that supports an occlusive assembly 3310 at distal end 3302. As shown, occlusive assembly 3310 includes an inner sheet 3312; however, in other implementations, occlusive assembly 3310 may include an occlusive body instead of or in addition to inner sheet 3312. Implant 3300 further includes an outer sheet 3314 supported on a proximal portion of frame 3308 such that an annular opening 3316 is defined between inner sheet 3312 and outer sheet 3314.

Frame 3308 of implant 3300 includes a distal frame portion 3318 including a set of circumferentially distributed arcuate petal portions, such as arcuate petal portion 3320A and arcuate petal portion 3320B. Frame 3308 further includes a proximal frame portion 3338 including a second set of circumferentially distributed arcuate petal portions, such as arcuate petal portion 3340A and arcuate petal portion 3340B.

As shown in FIG. 33, the first or inner set of arcuate petal portions of implant 3300 are shown as being substantially like those of implant 3100. However, in contrast to implant 3100, each arcuate petal portion of the second set of arcuate petal portions of implant 3300 is formed by arcuate frame members extending between longitudinal members. For example, arcuate petal portion 3340A is formed by arcuate frame member 3341A and arcuate frame member 3341B, which extend between longitudinal member 3348A and longitudinal member 3348B.

As shown in FIG. 33, longitudinal member 3348A and longitudinal member 3348B extend from respective junctions of the first set of arcuate petal portions. For example, longitudinal member 3348A extends from junction 3326 formed between arcuate petal portion 3320A and arcuate petal portion 3320B. Like noted above with respect to implant 3100, the first and second set of arcuate petal portions of implant 3300 may be rotationally offset from the configuration illustrated in FIG. 33 such that the longitudinal members instead extend from proximal vertices (e.g., proximal vertex 3325) of the first set of arcuate petal portions.

In the implementation shown, arcuate frame member 3341A is proximal and arcuate frame member 3341B and each of arcuate frame member 3341A and arcuate frame member 3341B are distally concave. In other implementations, one or both of arcuate frame member 3341A and arcuate frame member 3341B may be proximally concave. Also, in other implementations, the combination of arcuate frame member 3341A and arcuate frame member 3341B may be replaced with a single arcuate frame member or supplemented with any suitable number of additional arcuate frame members. Moreover, the number of arcuate frame members may vary between arcuate petal portions. So, for example, certain arcuate petal portions may include no or only a single arcuate frame member while others may include two or more.

As previously discussed herein, implants according to this disclosure are capable of transitioning between an expanded state (e.g., when implanted) and a collapsed state (e.g., during delivery). The transition from collapsed state into the expanded state causes a proximal portion of the frame of the implant to travel radially outward away from the central longitudinal axis of the implant. The transition into the expanded state may also include a longitudinal shift of the proximal portion of the frame. As a result, as the implant expands, it extends radially outward but reduces in length along the longitudinal axis.

The presence, size, and quantity of arcuate petal portions contributes to the overall length of the implant when in the collapsed state. When an arcuate petal portion is collapsed (e.g., when the implant is in the collapsed state), the arcuate petal portion undergoes each of circumferential compression and longitudinal elongation. As a result, a first implant with more and/or larger arcuate petal portions than a second implant will typically have a longer collapsed length than the second implant even when the first and second implants have the same overall dimensions when in their respective expanded states.

The relationship between collapsed length and arcuate petal portion characteristics may be leveraged to design implants for specific applications. For example, if a surgeon anticipates that delivery and implantation may be challenging, a first implant having a frame with more and/or longer longitudinal members may be selected over a second implant having a frame with more and/or larger arcuate petal portions due to the first implant having a shorter and more maneuverable length when in the collapsed state (i.e., during delivery). In contrast, if additional devices (e.g., pacemaker leads) are to be subsequently implanted in the patient, the surgeon may opt for the second implant due to the size, shape, and positioning of the openings defined by the arcuate petal portions providing additional options and flexibility for delivery and support of the additional devices.

As another example, designs with a higher proportion of longitudinal members tend to exert less radial force when transitioning between from the collapsed state to the expanded state and may generally exhibit lower radial rigidity. Accordingly, an implant frame with a higher proportion of longitudinal members and a lower proportion of arcuate petal portions (or similar expanding structures) may be selected in implementations in which cardiac tissue may be damaged by higher radial forces or that may require the implant to conform to more complex geometry within the heart.

Figure 34:
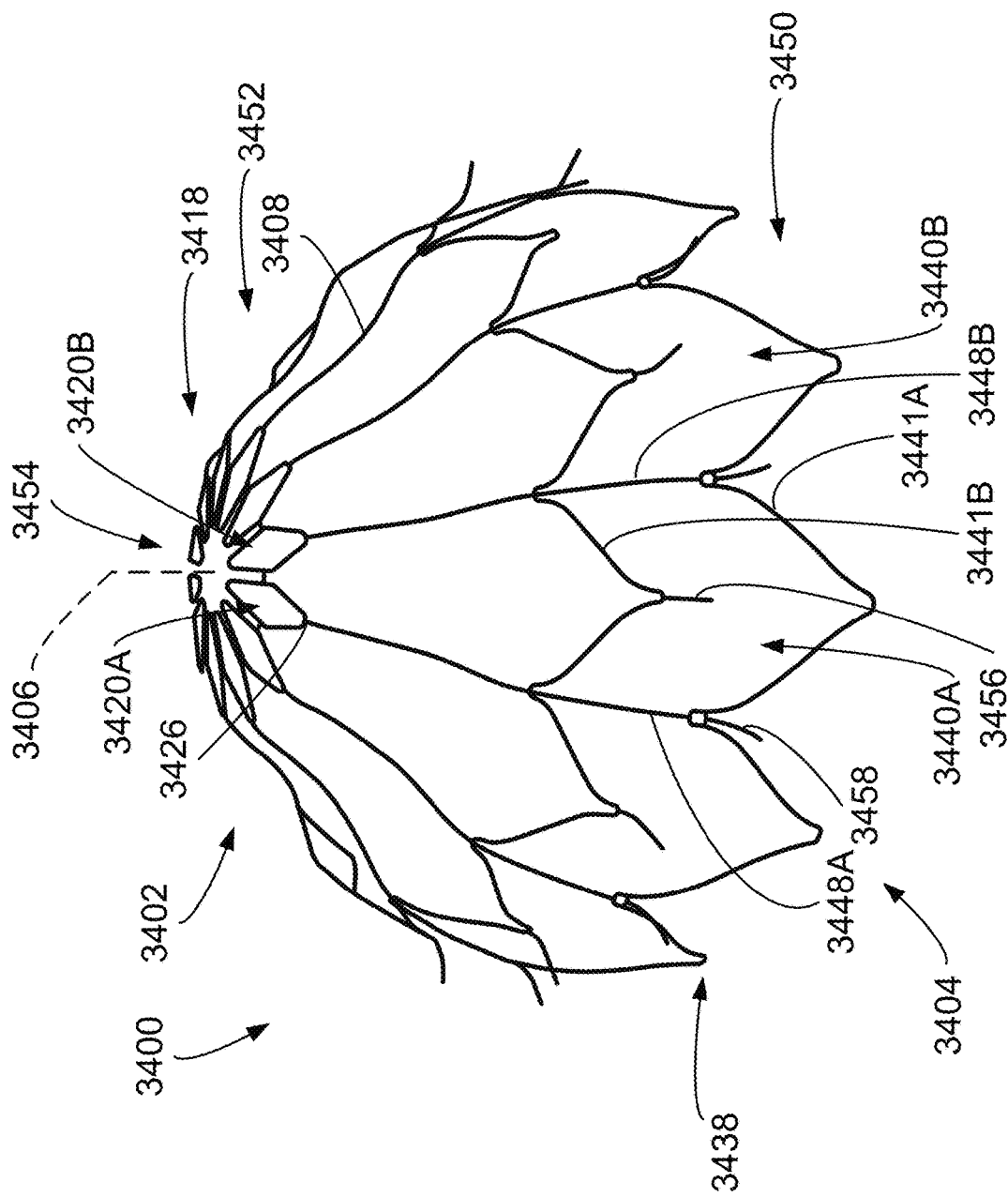
FIG. 34 is a perspective distal-end view of an implant having arcuate petal portions formed by arcuate members extending between longitudinal members and having an overall shape that includes a proximal portion having a proximally concave shape and a distal portion having a distally concave shape.

FIGS. 31-33 illustrate alternative frame configurations according to this disclosure and are limited to proximally concave designs. The frame configuration may nevertheless be readily adapted to other implant shapes including, but not limited to, implants having overall shapes that are distally concave, frustoconical, planar, or include combinations of different concavities. FIGS. 34-35B, for example, illustrate certain frame alternatives implemented in implants having a combination of a proximally concave distally concave distal portions.

FIG. 34 illustrates an implant 3400 having a frame configuration similar to that of implant 3300 of FIG. 33. Implant 3400 includes a distal end 3402 and a proximal end 3404 such that a longitudinal axis 3406 of implant 3400 extends between distal end 3402 and proximal end 3404. Implant 3400 includes a frame 3408 that may support an occlusive assembly at distal end 3302. FIG. 34 omits the occlusive assembly to show the various features and configuration of frame 3408 more clearly. Like other implementations discussed herein, when included, the occlusive assembly may include an occlusive body and/or an inner sheet. Implant 3400 may also include an outer sheet (not shown in FIG. 34) supported on a proximal portion of frame 3408 such that an annular opening is defined between the inner sheet/occlusive assembly and the outer sheet.

Frame 3408 of implant 3400 includes a distal frame portion 3418 including a set of circumferentially distributed arcuate petal portions, such as arcuate petal portion 3420A and arcuate petal portion 3420B. Frame 3408 further includes a proximal frame portion 3438 including a second set of circumferentially distributed arcuate petal portions, such as arcuate petal portion 3440A and arcuate petal portion 3440B. Each arcuate petal portion of the second set of arcuate petal portions of implant 3400 is formed by arcuate frame members extending between longitudinal members. For example, arcuate petal portion 3440A is formed by arcuate frame member 3441A and arcuate frame member 3441B, which extend between longitudinal member 3448A and longitudinal member 3448B. Longitudinal member 3348A and longitudinal member 3348B extend from respective proximal tips of arcuate petal portions of the first set of arcuate petal portions, e.g., longitudinal member 3448A extends from a proximal tip 3426 of arcuate petal portion 3420A.

In contrast to implant 3300 of FIG. 33, which has a proximally concave shape, implant 3400 of FIG. 34 has varying concavity, like implant 2900C of FIG. 29C. More specifically, implant 3400 includes each of a proximal portion 3450 that is proximally concave, a distal portion 3452 that is distally concave, and a cap portion 3454 that is proximally concave.

Implant 3400 further includes circumferentially distributed anchor members, such as anchor member 3456 and anchor member 3458. Anchor member 3456 is part of a first set of anchor members that extend radially outward from a proximal tip of a respective arcuate frame member. Specifically, each anchor member of the first set of anchor members extends from a proximal tip of the distal frame member of each arcuate petal portion. So, for example, anchor member 3456 extends from the proximal tip of arcuate frame member 3441B. Anchor member 3458, on the other hand, is part of a second set of anchor members that extend radially outward from junctions between arcuate tip members and longitudinal members. Specifically, each anchor member of the second set of anchor members extends from a respective junction between the proximal frame member of each arcuate petal portion and each longitudinal member. So, for example, anchor member 3458 extends from the junction between arcuate frame member 3441A and longitudinal member 3348A. In other implementations, anchor members may alternatively or additional be disposed at other locations of the frame including, but not limited, to the proximal tip of the proximal arcuate frame member (e.g., arcuate frame member 3441A) and the junctions formed between the distal arcuate frame members and the longitudinal members.

Figure 35A:
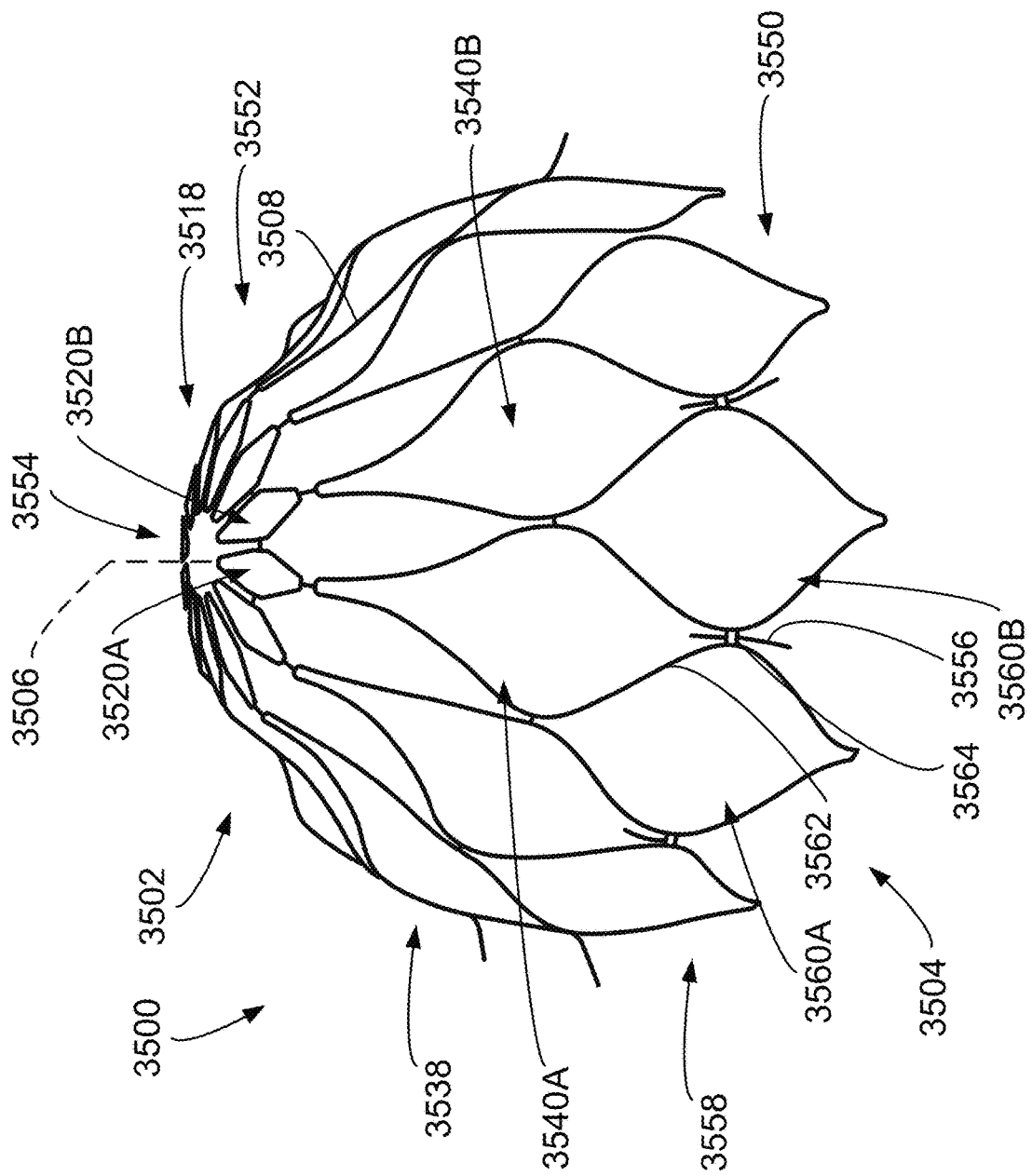
FIG. 35A is a first perspective distal-end view of an implant having arcuate petal portions formed by arcuate members extending between longitudinal members and having an overall shape that includes a proximal portion having a proximally concave shape and a distal portion having a distally concave shape.
Figure 35B:
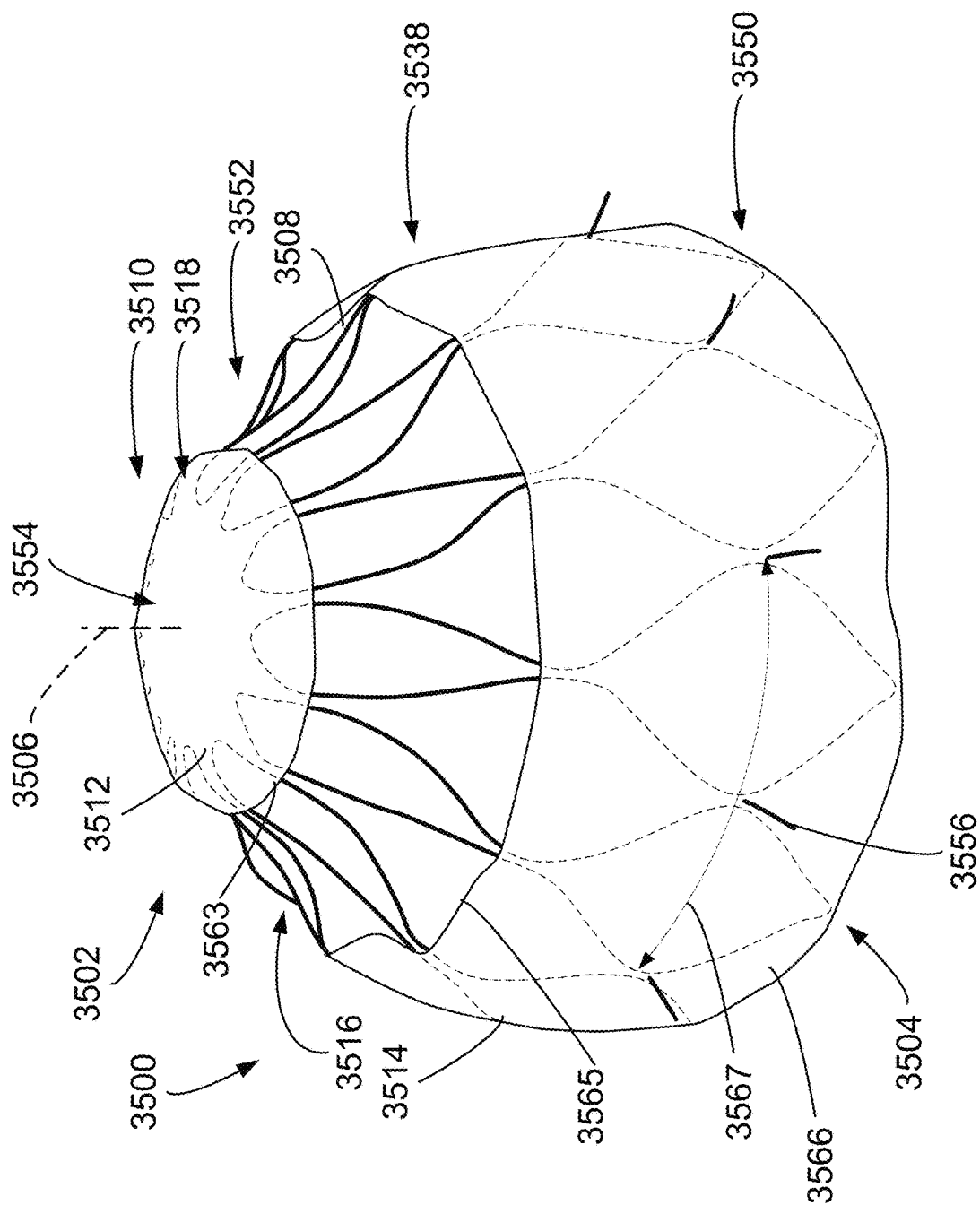
FIG. 35B is a second perspective distal-end view of the implant of FIG. 35A including each of inner and outer sheets.

FIGS. 35A and 35B illustrate another implant 3500 having an overall shape with varying concavities. Implant 3500 includes a distal end 3502 and a proximal end 3504 such that a longitudinal axis 3506 of implant 3500 extends between distal end 3502 and proximal end 3504. Implant 3500 includes a frame 3508 that may support an occlusive assembly 3510 at distal end 3302. FIG. 35A omits the occlusive assembly to show the various features and configuration of frame 3508 more clearly while; however, FIG. 35B includes occlusive assembly 3510. Like other implementations discussed herein, occlusive assembly 3510 includes an inner sheet 3512 but may alternatively or additionally include an occlusive body. Implant 3500 may also include an outer sheet 3514 (also shown in FIG. 35B), which is supported on a proximal portion of frame 3508 such that an annular opening 3516 is defined between inner sheet 3512 and outer sheet 3514.

Frame 3508 of implant 3500 includes a distal frame portion 3518 including a set of circumferentially distributed arcuate petal portions, such as arcuate petal portion 3520A and arcuate petal portion 3520B (each labelled in FIG. 35A). Frame 3508 further includes an intermediate frame portion 3538 including a second set of circumferentially distributed arcuate petal portions, such as arcuate petal portion 3540A and arcuate petal portion 3540B (each labelled in FIG. 35A) and a proximal frame portion 3558 including a third set of circumferentially distributed arcuate petal portions, such as arcuate petal portion 3560A and arcuate petal portion 3560B (each labelled in FIG. 35A). As most clearly seen in FIG. 35A, the first and second set of arcuate petal portions are aligned to facilitate joining of each arcuate petal portion of the first set of arcuate petal portions to a respective arcuate petal portion of the second set of petal portions. For example, a proximal tip of arcuate petal portion 3520A is joined to a distal tip of arcuate petal portion 3540A. In contrast, the second and third sets of arcuate petal portions are rotationally offset and longitudinally overlap each other. For example, arcuate petal portion 3540A is rotationally offset from and longitudinally overlaps arcuate petal portion 3560A. Adjacent arcuate petal portions of the second set and the third set may also share common frame elements. For example, arcuate petal portion arcuate petal portion 3540A and arcuate petal portion 3560A each include frame element 3562.

Like implant 3400 of FIG. 34 and implant 2900C of FIG. 29C, implant 3500 of FIG. 35 has varying concavity. More specifically, implant 3500 includes each of a proximal portion 3550 that is proximally concave, a distal portion 3552 that is distally concave, and a cap portion 3554 that is proximally concave.

Also, like implant 3400, implant 3500 includes circumferentially distributed anchor members, such as anchor member 3556. Anchor member 3556 is part of a set of anchor members that extend radially outward from each junction between adjacent arcuate petal portions of the third set of arcuate petal portions. So, for example, anchor member 3556 extends from a junction 3564 between arcuate petal portion 3560A and arcuate petal portion 3560B. In other implementations, anchor members may alternatively or additional be disposed at other locations of the frame including, but not limited, junctions between adjacent arcuate petal portions of the second set of arcuate petal portions and the proximal tips of the arcuate petal portions of the third set of arcuate petal portions.

Implementations of this disclosure corresponding to implant 3500 are not limited to any sizes or dimensions and may be modified or customized to meet the needs of patients and specific applications. Nevertheless, in certain implementations, a proximal radially outward edge 3563 of inner sheet 3512 may be from and including about 16 mm to and including about 30 mm. For example, in one specific implementation proximal radially outward edge 3563 may be 24 mm. Similarly, a distal radially inward edge 3565 of outer sheet 3514 may be from and including about 35 mm to and including about 55 mm. For example, in one specific implementation, proximal radially outward edge 3563 may be 42 mm. A proximal radially outward edge 3566 of implant 3500 may be from and including about 42 mm to and including about 68 mm. In one specific example, proximal radially outward edge 3566 may be 56 mm. In implementations in which implant 3500 includes anchor members, such as anchor member 3556, at least a portion of the anchor members may be distributed around a common circumference 3567 of implant 3500. Although the diameter of common circumference 3567 may vary, in at least certain implementations, common circumference 3567 may have a diameter from and including about 42 mm to and including about 68 mm. For example, common circumference 3567 may have a diameter of 54 mm. As a final example, the overall height of implant 3500 in the expanded state may vary; however, in at least certain implementations, the overall height of implant 3500 may be from and including about 26 mm to and including about 48 mm and, in one specific implementation, may be 36 mm.

While only a select few implementations of this disclosure are shown or described as including anchor members (e.g., protruding anchor members 105 of frame 55), such anchor members may be added to or otherwise included in any implant design discussed herein. Similarly, while this disclosure discusses control of implant expansion by a tension control line in the context of FIGS. 12-22, such functionality may be adapted to and included in any other implant discussed herein.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

X. Illustrative Examples

Illustrative examples of the disclosure include:

Aspect 1: A cardiac valve repair implant comprising: an occlusive assembly disposed along a central longitudinal axis of the cardiac valve repair implant; a frame coupled to the occlusive assembly and configured to transition from a collapsed state to an expanded state about the central longitudinal axis, wherein transitioning from the collapsed state to the expanded state causes a proximal end of the frame to expand radially outward from the central longitudinal axis; and an outer sheet supported on a proximal portion of the frame, wherein the occlusive assembly is supported on a distal portion of the frame such that an annular opening is defined between the outer sheet and the occlusive assembly when the frame is in the expanded state.

Aspect 2: The cardiac valve repair implant of Aspect 1 further comprising a tension control line extending about the frame, wherein transition of the frame between the collapsed state and the expanded state is controllable by selectively applying tension to the tension control line.

Aspect 3: The cardiac valve repair implant of Aspect 2 wherein the tension control line is coupled to a distal side of the frame.

Aspect 4: The cardiac valve repair implant of Aspect 2 wherein the tension control line is further coupled to the frame by a radially extending link.

Aspect 5: The cardiac valve repair implant of Aspect 1, wherein the occlusive assembly includes an occluder, and wherein the occluder includes an occluder body defining a cavity and an insert disposed within the cavity.

Aspect 6: The cardiac valve repair implant of Aspect 5, wherein the insert is coupled to the occluder body by a threaded connection.

Aspect 7: The cardiac valve repair implant of Aspect 5, wherein the occluder further includes a radiopaque marker.

Aspect 8: The cardiac valve repair implant of Aspect 1, wherein the frame comprises arcuate petal portions distributed circumferentially about the central longitudinal axis.

Aspect 9: The cardiac valve repair implant of Aspect 8, wherein the arcuate petal portions include a first set of arcuate petal portions and a second set of arcuate petal portions disposed radially inward of the first set of arcuate petal portions.

Aspect 10: The cardiac valve repair implant of Aspect 8, wherein the occlusive assembly is coupled to the arcuate petal portions by radially extending spokes extending from the occlusive assembly to the arcuate petal portions.

Aspect 11: The cardiac valve repair implant of Aspect 1, further comprising anchor members configured to protrude in a radially outward direction when the frame is in the expanded state.

Aspect 12: The cardiac valve repair implant of Aspect 11, wherein the anchor members are distributed circumferentially about the frame.

Aspect 13: The cardiac valve repair implant of Aspect 11, wherein the outer sheet is disposed on a distal side of the frame and the anchor members extending through the outer sheet.

Aspect 14: The cardiac valve repair implant of Aspect 11, wherein the frame comprises arcuate petal portions distributed circumferentially about the central longitudinal axis and the anchor members extend from at least one of tips of the arcuate petal portions and joints between adjacent arcuate petal portions.

Aspect 15: The cardiac valve repair implant of Aspect 1, wherein, when in the expanded state, the frame has a proximally concave shape.

Aspect 16: The cardiac valve repair implant of Aspect 1, wherein, when in the expanded state, the frame has a distally concave shape.

Aspect 17: The cardiac valve repair implant of Aspect 1, wherein, when in the expanded state, the frame has a proximally concave proximal portion and a distally concave distal portion.

Aspect 18: The cardiac valve repair implant of Aspect 17, wherein, when in the expanded state, the frame further has a proximally concave cap portion disposed on a distal end of the frame.

Aspect 19: The cardiac valve repair implant of Aspect 1, wherein, when in the expanded state, the frame has a frustoconical shape.

Aspect 20: The cardiac valve repair implant of Aspect 1, wherein, when in the expanded state, the frame has a planar shape.

Aspect 21: The cardiac valve repair implant of Aspect 1, wherein the frame includes distal arcuate petal portions, proximal arcuate petal portions, and longitudinal members extending between the distal arcuate petal portions and the proximal arcuate petal portions.

Aspect 22: The cardiac valve repair implant of Aspect 21, wherein each longitudinal member couples a proximal tip of a distal arcuate petal portion to a distal tip of a proximal arcuate petal portion.

Aspect 23: The cardiac valve repair implant of Aspect 21, wherein each longitudinal member couples a junction between adjacent distal arcuate petal portions to a distal tip of a proximal arcuate petal portion.

Aspect 24: The cardiac valve repair implant of Aspect 1, wherein the frame includes distal arcuate petal portions, longitudinal members extending proximal the distal arcuate petal portions and arcuate frame members extending between adjacent longitudinal members.

Aspect 25: The cardiac valve repair implant of Aspect 24, wherein a longitudinal member of the longitudinal members extends from a proximal tip of a respective distal arcuate petal portion.

Aspect 26: The cardiac valve repair implant of Aspect 24, wherein a longitudinal member of the longitudinal members extends from a junction between adjacent distal arcuate petal portions.

Aspect 27: The cardiac valve repair implant of Aspect 24, wherein the arcuate frame members include a first arcuate frame member and a second arcuate frame member extending between a pair of the longitudinal members, the second arcuate frame member disposed distal the first arcuate frame member.

Aspect 28: The cardiac valve repair implant of Aspect 1, wherein the frame includes distal arcuate petal portions, proximal arcuate frame members, and intermediate arcuate petal portions longitudinally disposed between the distal arcuate petal portions and the proximal arcuate petal portions.

Aspect 29: The cardiac valve repair implant of Aspect 28, wherein the frame further includes a longitudinal member extending between a distal arcuate petal portion of the arcuate petal portions and an intermediate arcuate petal portion of the intermediate arcuate petal portions.

Aspect 30: The cardiac valve repair implant of Aspect 29, wherein the longitudinal member couples a proximal tip of the distal arcuate petal portion to a proximal tip of the intermediate arcuate petal portion.

Aspect 31: The cardiac valve repair implant of Aspect 28, wherein the frame includes a frame element and the frame element partially defines each of a proximal arcuate petal portion of the proximal arcuate petal portions and an intermediate arcuate petal portion of the intermediate arcuate petal portions.

Aspect 32: The cardiac valve repair implant of Aspect 1, wherein the occlusive assembly further includes an inner sheet extending about the central longitudinal axis, wherein the inner sheet has a radially outward proximal edge, and wherein the radially outward proximal edge has a diameter from and including about 16 mm to and including about 30 mm.

Aspect 33: The cardiac valve repair implant of Aspect 32, wherein the radially outward proximal edge is about 24 mm.

Aspect 34: The cardiac valve repair implant of Aspect 1, wherein the outer sheet has a distal radially inward edge, and wherein the distal radially inward edge has a diameter from and including about 35 mm to and including about 55 mm.

Aspect 35: The cardiac valve repair implant of Aspect 34, wherein the distal radially inward edge has a diameter of about 42 mm.

Aspect 36: The cardiac valve repair implant of Aspect 1, wherein the implant has a proximal radially outward edge having a diameter from and including about 42 mm to and including about 68 mm.

Aspect 37: The cardiac valve repair implant of Aspect 36, wherein the proximal radially outward edge is about 56 mm.

Aspect 38: The cardiac valve repair implant of Aspect 1, wherein the frame includes anchor members that protrude distally from the frame when the frame is in the expanded state, wherein the anchor members are distributed circumferentially about the central longitudinal axis at an anchor diameter, and wherein the anchor diameter is from and including about 42 mm to and including about 68 mm.

Aspect 39: The cardiac valve repair implant of Aspect 38, wherein the anchor diameter is about 54 mm.

Aspect 40: The cardiac valve repair implant of Aspect 1, wherein, when in the expanded state, the cardiac valve repair implant has a length along the central longitudinal axis from and including about 26 mm to and including about 48 mm.

Aspect 41: A cardiac valve repair implant comprising: a central occluder; a frame extending proximally from the central occluder and defining a central longitudinal axis, the frame centered about and forming a circumference around the central longitudinal axis, the frame self-biasing from a collapsed state to an expanded state, wherein a proximal end of the frame projects proximally when the frame is in the collapsed state, and wherein the proximal end of the frame projects radially outward away from the central longitudinal axis of the central occluder when the frame is in the expanded state; and a thin sheet supported on a proximal portion of the frame, wherein when the frame is in the expanded state, the thin sheet forms an annular surface defining an inner circular opening centered about the central longitudinal axis of the central occluder.

Aspect 42: The cardiac valve repair implant of Aspect 82, wherein the frame includes anchor members on a distal side of the frame, the anchor members protruding distally from the frame when the frame is in the expanded state.

Aspect 43: The cardiac valve repair implant of Aspect 42, wherein the anchor members additionally protrude radially outward when the frame is in the expanded state.

Aspect 44: The cardiac valve repair implant of Aspect 42, wherein the anchor members additionally protrude radially inward when the frame is in the expanded state.

Aspect 45: The cardiac valve repair implant of Aspect 41, wherein the frame includes spokes that extend between a proximal end of the central occluder and the proximal portion of the frame that supports the thin sheet.

Aspect 46: The cardiac valve repair implant of Aspect 45, wherein the spokes are substantially straight and substantially parallel to the central longitudinal axis of the central occluder when the frame is in the collapsed state, and the spokes curve radially outward relative to the central longitudinal axis of the central occluder when the frame is in the expanded state.

Aspect 47: The cardiac valve repair implant of Aspect 45, wherein the proximal portion of the frame that supports the thin sheet includes arcuate petal portions extending from the spokes.

Aspect 48: The cardiac valve repair implant of Aspect 47, wherein each arcuate petal portion includes an outer arcuate member and an inner arcuate member radially inward of the outer arcuate member.

Aspect 49: The cardiac valve repair implant of Aspect 41, wherein the thin sheet is supported on a distal side of the frame.

Aspect 50: The cardiac valve repair implant of Aspect 41, wherein the thin sheet is supported on a proximal side of the frame.

Aspect 51: The cardiac valve repair implant of Aspect 41, wherein the central occluder includes a cylindrical side surface and a bullnose extending distally from the cylindrical side surface.

Aspect 52: The cardiac valve repair implant of Aspect 41, wherein the frame includes a shape-memory material that self-biases the frame from the collapsed state to the expanded state.

Aspect 53: The cardiac valve repair implant of Aspect 41, wherein the thin sheet includes a fabric material that allows for tissue ingrowth.

Aspect 54: A method of repairing a target cardiac valve, the method comprising: delivering an implant in a collapsed state into an atrium adjacent the target cardiac valve, the implant including a central occluder, a frame extending proximally from the central occluder, and a thin sheet supported on a proximal region of the frame, wherein when the implant is in the collapsed state, the frame and thin sheet are folded inward about a central longitudinal axis of the cardiac valve implant; approaching the target cardiac valve with the implant in an expanded state, wherein when the implant is in the expanded state, the frame and thin sheet are unfolded and form an annular structure defining an inner circular opening centered about the central longitudinal axis of the central occluder; and positioning the central occluder in an orifice of the target cardiac valve and a distal side of the annular structure against an annular region of cardiac tissue surrounding the target cardiac valve such that the inner circular opening opens over the orifice of the target cardiac valve.

Aspect 55: The method of Aspect 54, wherein the implant is delivered to the target valve via an antegrade percutaneous route.

Aspect 56: The method of Aspect 54, wherein the implant self-biases from the collapsed state to the expanded state.

Aspect 57: The method of Aspect 54, wherein a proximal end of the frame projects proximally when the frame is in the collapsed state, and wherein the proximal end of the frame projects radially outward away from the central longitudinal axis of the occluder when the frame is in the expanded state.

Aspect 58: The method of Aspect 54, wherein the frame includes anchor members on a distal side of the annular structure, and the anchor members protrude into the annular region of cardiac tissue surrounding the target cardiac valve.

Aspect 59: The method of claim Aspect 58, further comprising over expanding the implant to cause the anchor members to protrude into the annular region.

Aspect 60: The method of Aspect 58, further comprising pushing the implant distally against the annular region of cardiac tissue surrounding the target cardiac valve to cause the anchor members to protrude into the annular region.

Aspect 61: The method of Aspect 54, wherein the frame includes spokes that extend between a proximal end of the central occluder and the proximal portion of the frame that supports the thin sheet.

Aspect 62: The method of Aspect 54, wherein the frame includes a shape-memory material that self-biases the implant from the collapsed state to the expanded state.

Aspect 63: The method of Aspect 54, wherein the thin sheet includes a fabric material that allows for tissue ingrowth.

Aspect 64: The method of Aspect 54, wherein the central occluder is positioned in the orifice of the target cardiac valve such that the leaflets of the target cardiac valve abut against a cylindrical side of the central occluder.

Aspect 65: A delivery tool for cardiac valve repair implants, the delivery tool comprising: an outer sheath; a release catheter insertable into the outer sheath, wherein the release catheter defines a central lumen and includes a release line extending through the central lumen from a proximal end of the release catheter to a distal end of the release catheter, the release line to selectively couple a cardiac valve implant to a distal end of the delivery tool; and a tension control assembly insertable into the release catheter, wherein the tension control assembly includes a tension control member selectively coupleable to a tension control line of the cardiac valve implant by the release line, the tension control assembly manipulable to apply tension to the tension control line using the tension control member.

Aspect 66: The delivery tool of Aspect 65, wherein the release catheter defines a lateral opening and, wherein, when the tension control assembly is inserted into the release catheter, the tension member extends through the lateral opening.

Aspect 67: The delivery tool of Aspect 65, wherein the tension control member terminates in a loop.

Aspect 68: The delivery tool of Aspect 65, wherein the release catheter defines a lateral opening and, wherein, when coupled to the cardiac valve implant, the release line extends from a distal opening of the release catheter and is routed back through the lateral opening.

Aspect 69: A delivery tool for cardiac valve repair implants, the delivery tool comprising: an outer sheath defining a central lumen shaped to receive an expandable frame of a cardiac valve repair implant; a catheter insertable into the central lumen of the outer sheath, wherein, when inserted into the central lumen with the expandable frame within the central lumen, a distal catheter end abuts an occluder of the cardiac valve repair implant such that distal translation of the catheter distally translates the expandable frame from the central lumen; and a handle assembly coupled to a proximal end of the catheter and coupleable to the expandable frame by a plurality of sutures, wherein the handle assembly is manipulable to control tension on the plurality of sutures when the plurality of sutures are couples to the expandable frame, thereby controlling expansion of the expandable frame.

Aspect 70: The delivery tool of Aspect 69, wherein the handle assembly includes a handle that is longitudinally translatable relative to the catheter and wherein longitudinally translating the handle controls expansion of the expandable frame.

Aspect 71: The delivery tool of Aspect 69, wherein the handle assembly includes a handle that is rotatable relative to the catheter to control expansion of the expandable frame.

Aspect 72: The delivery tool of Aspect 69, wherein the handle assembly includes a handle that is both longitudinally translatable and rotatable relative to the catheter to control expansion of the expandable frame.

Aspect 73: The delivery tool of Aspect 72, wherein translating the handle changes expansion of the expandable frame at a first rate and rotating the handle changes expansion of the expandable frame at a second rate less than the first rate.

Aspect 74: The delivery tool of Aspect 69, wherein the catheter is steerable by sutures routed from a distal end of the catheter to the handle assembly.

Aspect 75: The delivery tool of Aspect 69, wherein the handle assembly further includes a steering control to steer the distal catheter end.

Aspect 76: The delivery tool of Aspect 75, wherein the steering tool includes a lateral member coupled to the distal catheter end by a pull wire, and wherein rotating the lateral member creates tension on the pull wire to steer the distal catheter end.

Aspect 77: The delivery tool of Aspect 75, wherein the steering tool includes a lateral member coupled to a first side of the distal catheter end by a first pull wire and a second side of the distal catheter end by a second pull wire, wherein rotating the lateral member in a first direction increases tension on the first pull wire to pull the distal catheter end toward the first side, and wherein rotating the lateral member in a second direction increases tension on the second pull wire to pull the distal catheter end toward the second side.

What is claimed is:

1. A cardiac valve repair implant comprising:
   an occlusive assembly including an inner sheet;
   a frame coupled to the occlusive assembly and configured to transition from a collapsed state to an expanded state about a central longitudinal axis of the cardiac valve repair implant, wherein transitioning from the collapsed state to the expanded state causes a proximal end of the frame to expand radially outward from the central longitudinal axis; and
   an outer sheet supported on a proximal portion of the frame,
   wherein the occlusive assembly is supported on a distal portion of the frame such that the inner sheet extends about the central longitudinal axis and an annular opening is defined between the outer sheet and the inner sheet when the frame is in the expanded state.

2. The cardiac valve repair implant of claim 1, wherein the occlusive assembly further includes an occlusive body supported at a distal end of the frame along the central longitudinal axis.

3. The cardiac valve repair implant of claim 1, wherein the occlusive assembly further includes an occlusive body supported at a distal end of the frame along the central longitudinal axis and the inner sheet is coupled to the occlusive body.

4. The cardiac valve repair implant of claim 1, wherein the frame is proximally concave when in the expanded state.

5. The cardiac valve repair implant of claim 1, wherein the frame is distally concave when in the expanded state.

6. The cardiac valve repair implant of claim 1, wherein the frame is planar when in the expanded state.

7. The cardiac valve repair implant of claim 1, wherein the frame is biased into the expanded state.

8. The cardiac valve repair implant of claim 1, wherein the inner sheet is supported on the distal portion of the frame.

9. The cardiac valve repair implant of claim 1, wherein the frame includes distal arcuate petal portions and the inner sheet is supported on the distal arcuate petal portions.

10. The cardiac valve repair implant of claim 1, wherein the proximal portion of the frame that supports the outer sheet includes arcuate petal portions.

11. The cardiac valve repair implant of claim 1, wherein, the frame includes anchor members that protrude distally from the frame when the frame is in the expanded state.

12. The cardiac valve repair implant of claim 1, wherein, the frame includes:
    a first set of anchor members; and
    a second set of anchor members,
    wherein, when the frame is in the expanded state, each of the first set of anchor members and the second set of anchor members extends in an at least partially distal direction when the frame is in the expanded state and wherein the first set of anchor members is disposed at a different radius from the central longitudinal axis than the second set of anchor members.

13. The cardiac valve repair implant of claim 1, wherein at least one of the outer sheet and the inner sheet includes fabric material that allows for tissue ingrowth.

14. A cardiac valve repair implant comprising:
    a central occluder;
    a frame extending from the central occluder and supporting the central occluder on a distal portion of the frame, wherein the frame is configured to transition from a collapsed state to an expanded state, wherein a proximal end of the frame projects proximally when the frame is in the collapsed state, and wherein the proximal end of the frame projects radially outward away from a central longitudinal axis of the cardiac valve repair implant when the frame is in the expanded state;

an outer sheet supported on a proximal portion of the frame; and an inner sheet about the central occluder, wherein when the frame is in the expanded state, the central occluder is disposed along the central longitudinal axis and an annular opening is defined between the outer sheet and the inner sheet, the annular opening centered about the central longitudinal axis.

15. The cardiac valve repair implant of claim 14, further comprising an inner frame extending from the central occluder, wherein the inner frame includes inner arcuate petal portions and the inner sheet is supported on the inner arcuate petal portions.

16. The cardiac valve repair implant of claim 14, wherein, the frame includes anchor members that protrude distally from the frame when the frame is in the expanded state.

17. The cardiac valve repair implant of claim 14, wherein the proximal portion of the frame that supports the outer sheet includes first arcuate petal portions and the distal portion of the frame that supports the inner sheet includes second arcuate petal portions.

18. The cardiac valve repair implant of claim 14, wherein the frame is one of proximally concave and distally concave when in the expanded state.

19. A method of repairing target cardiac valves, the method comprising:

delivering an implant in a collapsed state into an atrium adjacent a target cardiac valve, the implant having an occlusive assembly including an inner sheet, a frame coupled to the occlusive assembly, and an outer sheet supported on a proximal portion of the frame, wherein the inner sheet of the occlusive assembly is supported on a distal portion of the frame, and wherein, when the implant is in the collapsed state, the frame and the inner sheet are folded inward about a central longitudinal axis of the frame;

approaching the target cardiac valve with the implant in an expanded state, wherein when the implant is in the expanded state, the frame, the outer sheet, and the inner sheet are unfolded such that the inner sheet and the outer sheet form an annular structure defining an annular opening between the inner sheet and the outer sheet, the annular opening centered about the central longitudinal axis; and positioning the occlusive assembly in an orifice of the target cardiac valve and a distal side of the annular structure against an annular region of cardiac tissue surrounding the target cardiac valve such that the annular opening opens over the orifice of the target cardiac valve.

20. The method of claim 19, wherein:

the occlusive assembly further includes an occlusive body supported at a distal end of the frame along the central longitudinal axis, the inner sheet is coupled to and extends from the occlusive body, and positioning the occlusive assembly in the orifice of the target cardiac valve includes positioning the occlusive body to interact with leaflets of the target cardiac valve.

* * * * *